United States Patent [19]
Harding et al.

[11] Patent Number: 6,022,696
[45] Date of Patent: Feb. 8, 2000

[54] METHODS OF IDENTIFYING AGONISTS OR ANTAGONISTS OF ANGIOTENSIN IV

[75] Inventors: Joseph W. Harding; John W. Wright, both of Pullman, Wash.

[73] Assignee: Washington State University Research Foundation, Pullman, Wash.

[21] Appl. No.: 09/054,308

[22] Filed: Apr. 2, 1998

Related U.S. Application Data

[60] Division of application No. 08/360,784, filed as application No. PCT/US93/06038, Jun. 24, 1993, Pat. No. 5,854,388, which is a continuation-in-part of application No. 07/906,396, Jun. 24, 1992, abandoned.

[51] Int. Cl.⁷ ............................. G01N 33/567; C07K 7/14
[52] U.S. Cl. .......................... 435/7.21; 435/7.1; 435/7.2; 530/316; 530/329
[58] Field of Search ........................... 435/7.1, 7.2, 7.21; 530/316, 329

[56] References Cited

U.S. PATENT DOCUMENTS

| | | | |
|---|---|---|---|
| 3,920,627 | 11/1975 | Wissman et al. | 260/112.5 |
| 5,296,354 | 3/1994 | Simon et al. | 435/7.92 |
| 5,464,821 | 11/1995 | Stig et al. | 514/18 |
| 5,470,753 | 11/1995 | Sepetov et al. | 436/89 |

FOREIGN PATENT DOCUMENTS 0 445 606 A1   9/1991   European Pat. Off. .

OTHER PUBLICATIONS

Peach, M.J., "Renin–Angiotensin System: Biochemistry and Mechanisms of Action," *Physio. Rev.* 57:313–370 (1977).

Johnston, C.I., "Biochemistry and Pharmacology of the Renin–Angiotensin System," *Drugs* 39 (Suppl. 1):21–31 (1990).

Blair–West, J.R. et al., "Effect of the Heptapeptide (2–8) and Hexapeptide (3–8) Fragments Angiotensin II on Aldosterone Secretion," *J. Clin. Endocrinol. Metab.* 32:575–578 (1971).

Harding, J.W. et al., "Angiotensin–Sensitive Neurons in the Rat Paraventricular Nucleus: Relative Potencies of Angiotensin II and Angiogensin III," *Brain Res.* 410:130–134 (1987).

Regoli, D. et al., "The Enzymatic Degradation of Various Angiotensin II Derivatives By Serum, Plasma or Kidney Homogenate," *Biochem. Pharmacol.* 12:637–646 (1963).

Bumpus, F.M. et al., "The Relationship of Structure to Pressor and Oxytocic Actions of Isoleucine⁵ Angiotensin Octapeptide and Various Analogues," *Biochim. Biophys. Acta* 46:38–44 (1961).

Regoli, D. et al., "Pharmacology of Angiotensin," *Pharmacol. Reviews* 26:69–123 (1974).

Bennett, J.P. et al., "Angiotensin II Binding to Mammalian Brain Membranes," *J. Biol. Chem.* 251:7423–7430 (1976).

Glossman, H. et al., "Properties of Angiotensin II Receptors in the Bovine and Rat Adrenal Cortex," *J. Biol. Chem.* 249:825–834 (1974).

Fitzsimons, J.T., "The Effect on Drinking of Peptide Precursors and of Shorter Chain Peptide Fragments of Angiotensin II Injected into the Rat's Diencephalon," *J. Physiol. Lond.* 214:295 (1971).

Tonnaer, V.M., "Central Effects of Angiotensins on Drinking and Blood Pressure: Structure–Activity Relationships," *Brain Res.* 236:417 (1982).

Siemens, I.R. et al., "Solubilization and Partial Characterization of Angiotensin II Receptors from Rat Brain," *J. Neurochem* 57:690–700 (1991).

Kono, T. et al., "Biological Activity of Des–(Asp¹, Arg², Val³)–Angiotensin II in Man," *Life Sci.* 32:337–343 (1983).

Kono, T. et al., "Responses of Patients with Bartter's Syndrome to Angiotensin II and Angiotensin II–(3–8)–Hexapeptide," *Acta Endocr.* 109:249–253 (1985).

Haberl, R.L. et al., "Angiotensin Degradation Products Mediate Endothelium–Dependent Dilation of Rabbit Brain Arterioles," *Circ. Res.* 68:1621–1627 (1991).

Braszko, J.J. et al., "The 3–7 Fragment of Angiotensin II is Probably Responsible For its Psychoactive Properties," *Brain Res.*, 542:49–54 (1991).

Braszko, J.J. et al., "Angiotensin II–(3–8)–Hexapeptide Affects Motor Activity, Performance of Passive Avoidance and a Conditioned Avoidance Response in Rats," *Neurosci.* 27:777–783 (1988).

Barszko, J.J. et al., "Psychotropic Effects of Angiotensin II and III in Rats: Locomotor and Exploratory vs. Cognitive Behavior," *Behav. Brain. Res.* 25:195–203 (1987).

(List continued on next page.)

*Primary Examiner*—Prema Mertz
*Assistant Examiner*—Fozia Hamud
*Attorney, Agent, or Firm*—Christensen O'Connor Johnson & Kindness PLLC

[57] ABSTRACT

A unique and novel angiotensin AT4 receptor and AIV ligand system for binding a small N-terminal hexapeptide fragment of Angiotensin II (referred to as AIV, with amino acid sequence $Val_1$-$Tyr_2$-$Ile_3$-$His_4$-$Pro_5$-$Phe_6$; SEQ. ID. NO. 1) is disclosed. AIV ligand binds saturably, reversibly, specifically, and with high affinity to membrane AT4 receptors in a variety of tissues, including heart, lung, kidney, aorta, brain, liver, and uterus, from many animal species. The AT4 receptor is pharmacologically distinct from classic angiotensin receptors (AT1 or AT2). The system employs AIV or C-terminally truncated or extended AIV-like peptides (e.g., VYIHPFX; SEQ. ID. NO. 8) as the signaling agent, and the AT4 plasma membrane receptor as the detection mechanism. The angiotensin AT4 receptor and receptor fragments (including the receptor binding site domain) are capable of binding a VYIHPF (SEQ. ID. NO. 1) angiotensin AIV N-terminal peptide but not an angiotensin AII or AIII N-terminal peptide, i.e., DRVYIHPF (SEQ. ID. NO. 2) or RVYIHPF (SEQ. ID. NO. 3), respectively. Also disclosed are processes for isolating angiotensin AT4 receptor and AIV angioteninase, identifying angiotensin AIV agonists and antagonists, and constructing diagnostic assays to specifically measure AIV and AI-specific angiotensinase in biological fluids.

7 Claims, 16 Drawing Sheets

OTHER PUBLICATIONS

Semple, P.F. et al., "Angiotensin II and its Heptapeptide (2–8), Hexapeptide (3–8), and Pentapeptide (4–8) Metabolites in Arterial and Venous Blood of Man," *Circ. Res.* 39:671–678 (1976).

Blumberg, A.L. et al., "Angiotensin (A I, A II, A III) Receptor Characterization," *Circ. Res.* 41:154–158 (1977).

Bennett, J.P. et al., "Receptor Binding Interactions of the Angiotensin II Antagonist, $^{125}$I-[Sarcosine$^1$,Leucine$^8$] Angiotensin II, With Mammalian Brain and Peripheral Tissues," *Eur. J. Pharmacol.* 67:11–25 (1980).

Fernandez, L.A. et al., "Neovascularization Produced by Angiotensin II," *Lab. Clin. Med.* 105:141–145 (1985).

Patel, J.M. et al., "Angiotensin Receptors in Pulmonary Arterial and Aortic Endothelial Cells," *Am. J . Physiol.* 256:C987–C993 (1989).

Baker, K.M. et al., "Angiotensin II Stimulation of Protein Synthesis and Cell Growth in Chick Heart Cells," *Am. J. Physiol.* 259:H610–H618 (1990).

Baker, K.M. et al., "Renin–Angiotensin System Involvement in Pressure–Overload Cardiac Hypertrophy in Rats," *Am. J. Physiol.* 259:H324–H332 (1990).

Yamaguchi, T. et al., "Role of the Adrenal Renin–Angiotensin System on Adrenocorticotropic Hormone– and Potassium–Stimulated Aldosterone Production by Rat Adrenal Glomerulosa Cells in Monolayer Culture," *Hypertension* 16:635–641 (1990).

Carpenter, G. et al., "Rapid Enhancement of Protein Phosphorylation in A–431 Cell Membrane Preparations by Epidermal Growth Factor," *J. Biol. Chem.* 254:4884–4891 (1979).

Munson, P.J. et al., "Ligand: A Versatile Computerized Approach for Characterization of Ligand–Binding Systems," *Anal. Biochem.* 107:220–239 (1980).

Freissmuth, M. et al., "G Proteins Control Diverse Pathways of Transmembrane Signaling," *FASEB J.* 3:2125–2131 (1989).

Brown, A.M. et al., "Direct G Protein Gating of Ion Channels," *Am. J. Physiol.* 254:H401–410 (1988).

Schulz, S. et al., "The Guanylate Cyclase/Receptor Family of Proteins," *FASEB J.* 3:2026–2035 (1989).

Nishibe, S. et al., "Increase of the Catalytic Activity of Phospholipase Cγ1 by Tyrosine Phosphorylation," *Science* 250:1253–1256 (1990).

Pandiella, A. et al., "Transmembrane Signalling at the Epidermal Growth Factor Receptor," *TiPS* 10:411–414 (1989).

Cohen, S. et al., "Epidermal Growth Factor–Receptor–Protein Kinase Interactions," *J. Biol. Chem.* 255:4834–4842 (1980).

Pang, D.T. et al., Protein Tyrosine Phosphorylation in Synaptic Vesicles, *Proc. Nat. Acad. Sci. USA* 85:762–766 (1988).

Wright, J.W. et al., "Structure–Function Analyses of Brain Angiotensin Control of Pressor Action in Rats," *Am. J. Physiol.* 257:R1551–R1557 (1989).

Gill, G.N. et al., "Angiotensin Stimulation of Bovine Adrenocortical Cell Growth," *Proc. Nat. Acad. Sci. USA* 74:5569–5573 (1977).

Aceto, J.F. et al., "[Sar$^1$]Angiotensin II Receptor–Mediated Stimulation of Protein Synthesis in Chick Heart Cells," *Am. J. Physiol.* 258:H806–H813 (1990).

Mendelsohn, F.A.O. et al., "Autoradiographic Localization of Angiotensin II Receptors in Rat Brain," *Proc. Natl. Acad. Sci. USA* 81:1575–1579 (1984).

Harding, J.W. et al., "Angiotensin and Blood Pressure Regulation," *Acad. Press,* San Diego, CA. p. 1–34 (1988).

Paul, A.K. et al., "Coexistence of Guanylate Cyclase and Atrial Natriuretic Factor Receptor in 180–kD Protein," *Science* 235:1224–1226 (1987).

Abhold, R.H. et al., "Metabolism of Angiotensins II and III by Membrane–Bound Peptidases from Rat Brain," *J. Pharmacol Exp. Ther.* 245:171–177 (1988).

International Search Report, PCT/US93/06038.

Sardinia, M.F. et al., "$AT_4$ Receptor Binding Characteristics: D–Amino Acid– and Glycine–Substituted Peptides," *Peptides* 14:949–954 (1993).

Hanesworth, J.M. et al., "Elucidation of a Specific Binding Site for Angiotensin II(3–8), Angiotensin IV, in Mammalian Heart Membranes," *The Journal of Pharmacology and Experimental Therapeutics* 266(2):1036–1042 (1993).

Swanson, G.N. et al., "Discovery of a distinct binding site for angiotensin II(3–8), a putative angiotensin IV receptor," *Regulatory Peptides* 40(3):409–419 (1992).

METHODS OF IDENTIFYING AGONISTS OR ANTAGONISTS OF ANGIOTENSIN IV

This is a divisional of application Ser. No. 08/360,784 filed Dec. 22, 1994 now U.S. Pat. No. 5,854,388, which is the U.S. national phase of International application Serial No. PCT/US93/06038 filed Jun. 24, 1993, which is a continuation-in-part of application Ser. No. 07/906,396 filed Jun. 24, 1992, now abandoned.

FIELD OF THE INVENTION

This invention relates to the polypeptide ligand VYIHPF (SEQ. ID. NO. 1) (angiotensin IV or AIV) and to related peptide ligands and polyaminoacid ligands that bind to, activate and/or antagonize a novel angiotensin AT4 receptor. The ligands comprise at least three of the N-terminal amino acids of AIV, or AT4 receptor binding equivalents or analogs thereof. Engagement of the receptor by its ligand triggers acute physiological effects (e.g., vasodilation) and long-term effects in cells (e.g., hypertrophic growth).

BACKGROUND OF THE INVENTION

The renin-angiotensin system has wide-ranging actions on numerous tissues in the body affecting blood pressure (pressor activity) and cardiovascular and electrolyte homeostasis. It is currently believed that angiotensins AII and AIII are derived via enzymatic cleavage in the cascade depicted in FIG. 1, steps 1, 2, and 3 (1). (Numbering herein of the amino acid residues in AI, AII, AIII, and AIV is according to that appearing in FIG. 1.) The resin-angiotensin cascade is thought to begin with the action of renin or angiotensinogen to release angiotensin I (AI), a biologically inactive decapeptide. Angiotensin II (AII), the bioactive octapeptide, is thought to be formed by the action of angiotensin converting enzyme (ACE) on circulating AI (2). Des-AspAII (Angiotensin III; AIII) is derived from AII, and certain reports have suggested possible activities for AIII in the adrenal gland (3) and brain (4). It has been reported that AII and AIII are inactivated by enzymatic degradation through a series of smaller inactive fragments (5). Fragments smaller than AIII have been though, for the most part, to be biologically inactive and of little physiological significance (6). This assumption has been based on the lack of pressor and certain endocrine activities (i.e., aldosterone release) of small angiotensin fragments (7) and the finding that N-terminal deleted fragments, i.e., smaller than AIII, reportedly exhibit low binding affinity for angiotensin AI or AII receptors (known as AT1 and AT2, respectively) as determined in radiolabeled ligand studies (8).

Certain studies have used $AII_{(3-8)}$ as one of several controls in structure-activity studies of AT1 and AT2 receptors (9,10). An AII receptor having components with molecular weights of 60–64 kDa and 112–115 kDa has reportedly been cloned from adrenal cortical cells as well as rat smooth muscle (11).

In general, $AII_{(3-8)}$ has been found to be much less active than AII or AIII with regard to typical angiotensin-dependent pressor activity or stimulating water intake (9,10, 12). However, certain reports have suggested that $AII_{(3-8)}$, while having little pressor activity or ability to stimulate aldosterone release, may under certain circumstances inhibit renin release from kidney (12,13). Haberl et al. (14) reported a possible effect of $AII_{(3-8)}$ on endothelium-dependent dilation in rabbit brain. Braszko et al. (15,16) reported possible effects of $AII_{(3-8)}$ or $AII_{(3-7)}$ on motor activity, memory, and learning when administered intracerebroventricularly (icv) into rat brain and suggested that these effects should be considered "unspecific," i.e., not mediated by receptors (Braszko et al. (17), p. 195).

The angiotensin field has often been fraught with complexity and conflicting information, particularly with regard to the levels of different AII and AIII peptides required to elicit certain cellular responses, the concentrations predicted from receptor binding studies to be biologically active, and the levels of angiotensin peptides that may be measured in biological fluids. It has been reported that AII and AIII are removed from, or destroyed in, circulation by enzymatic hydrolysis. Biological half-lives of the different metabolic fragments are reportedly quite short. Semple and co-workers (18) reportedly detected AIII, $AII_{(3-8)}$, and $AII_{(4-8)}$ in arterial and venous blood in man with half-lives for AII, AIII, $AII_{(3-8)}$, and $AII_{(4-8)}$ of 4.4, 2.0, 1.9, and 2.4 minutes, respectively. Blumberg et al. (19) reported that during transit through the kidney 72–76% of AI and AII and 89% of AIII was metabolized.

Confusion has existed in the art as to how metabolic products of AII and AIII can exhibit certain biological activities (e.g., inhibition of renin release and enhancement of cognitive function), while failing to bind to AI or AII receptors. Fragments of AII smaller than AIII, e.g., $AII_{(3-8)}$ and other smaller fragments, have not been reported to have specific saturable binding sites in tissues, and receptors for these fragments have not been identified previously. The present invention provides partial explanation for certain previous confusing and contradictory findings, and provides novel AIV receptors (AT4), AIV ligands, peptides, analogs, agonists and antagonists that bind specifically to the AT4 receptor and not to AI (AT1) or AII (AT2) receptors. The AIV peptides and the AT4 receptor are labile and subject to proteolytic degradation. In other aspects, the invention provides a specific angioteninase enzyme that converts AII or AIII peptides to AIV peptides in a novel pathway.

SUMMARY OF THE INVENTION

The discovery, herein, of a unique and novel angiotensin AIV receptor (AT4) and AIV ligand system for binding a small N-terminal hexapeptide fragment of Angiotensin II (referred to herein as AIV, with amino acid sequence $Val_1$-$Tyr_2$-$Ile_3$-$His_4$-$Pro_5$-$Phe_6$) (SEQ. ID. NO. 1) provides partial explanation for confusion in the prior art. AIV binds saturably, reversibly, specifically, and with high affinity to membrane AT4 receptors in a variety of tissues and from many animal species. The AT4 receptor is pharmacologically distinct from classic angiotensin receptors (AT1 or AT2) in that the AT4 receptor displays no specificity for classic agonists (AII and AIII) and antagonists ($Sar_1,Ile_8$-AII). Thus, the disclosure details the pharmacological and biochemical characterization of a newly discovered branch of the renin-angiotensin system that employs an AIV ligand as the signaling agent, and the AT4 plasma membrane receptor as the detection mechanism.

Angiotensin AIV appears to specifically mobilize calcium in vascular endothelial cells where AIV binding is evident. Binding to the endothelial AT4 receptor appears to trigger cellular proliferation. Binding of AIV to AT4 receptors in kidney and brain increases blood flow. In addition, binding of AIV to AT4 receptors in the brain facilitates learning and memory retention. AIV has also been shown to block the hypertrophic action of AII on cardiocytes despite its inability to bind AT2 receptors. Since cardiocytes possess large numbers of AT4 receptors this action of AIV is most likely direct. Thus, in certain respects the action of AIV appears to neutralize, or act in apposition to the actions of AII and AIII.

The invention provides an angiotensin AT4 receptor and receptor fragments (including the receptor binding site domain) that are capable of binding a VYIHPF (SEQ. ID. NO. 1) angiotensin AIV N-terminal peptide, and related AIV ligands, but do not bind an angiotensin AII or AIII N-terminal peptide, i.e., DRVYIHPF (SEQ. ID. NO. 2) or RVYIHPF SEQ. ID. NO. 3), respectively. The AT4 receptor from adrenal cortical cells has a molecular size of about 140 kD to about 150 kD on SDS-PAGE following crosslinking, a $K_d$ of about 0.5 nM for AIV peptides, and is widely expressed on the surface of adrenal cortical and medullary tissues in many mammalian species. The receptor is expressed in all important organs and tissues including heart, lung, kidney, aorta, brain, liver, and uterus.

The invention further provides processes for identifying angiotensin AIV agonists and antagonists, and constructing diagnostic assays to specifically measure AIV and AT4 receptors.

BRIEF DESCRIPTION OF THE DRAWINGS

FIG. 5A shows changes in arterial blood pressure following administration of Lys$_1$AIV at 100 pmole/25 ml/min (open circles) or saline control (closed circles). FIG. 5B shows changes in renal blood flow following administration of Lys$_1$AIV at 100 pmole/25 µl/min (open circles) or saline control (closed circles).

FIG. 6A shows changes in arterial blood pressure following administration of Nro-LeuYIHPF (SEQ. ID. NO. 4) at 100 pmole/25 µl/min (open circles), 50 fmole/25 µl/min (open squares) or saline control (closed squares). FIG. 6B shows changes in renal blood flow following administration of NorLeuYIHPF (SEQ. ID. NO. 4) at 100 pmole/25 µl/min (open circles), 50 fmole/25 µl/min (open squares) or saline control (closed squares).

FIG. 7A shows the results of kinetic analyses measuring binding of AIV to coronary venule endothelial cells (CVEC) showing maximal equilibrium binding in about 60 minutes with an apparent Ka of about $9.3 \times 10^7$ M$^{-1}$. FIG. 7B shows the results of kinetic studies measuring the dissociation of AIV from CVEC endothelial cells with an apparent $K_d$ of about 0.3 nM. FIG. 7C shows the results of equilibrium binding of AIV to 2 separable types of AT4 receptor sites in coronary venule endothelial cells (CVEC). One type of site with a $K_d$ of about 1.4±0.2 nM and a second type of site with a $K_d$ of about 14.6±26.5 pM. FIG. 7D shows the results of equilibrium binding of AIV to 2 separable types of AT4 receptor sites in aortic endothelial cells: one type of site with a $K_d$ of about 4.4±0.8 nM and a second type of site with a $K_d$ of about 26.9±9 pM. FIG. 8 shows competition of $^{125}$ I-AIV binding to coronary venule endothelial cells (CVEC) by non-radiolabeled AIV analogs. FIG. 9 shows association of AT2 receptors with G-protein in vascular smooth muscle cells (RVSMC), but non-association of AIV with G-proteins in endothelial cells (BAEC), as evidenced by the inhibility of GTPγS to inhibit AIV binding.

DETAILED DESCRIPTION OF THE PREFERRED EMBODIMENT

Figure 1:
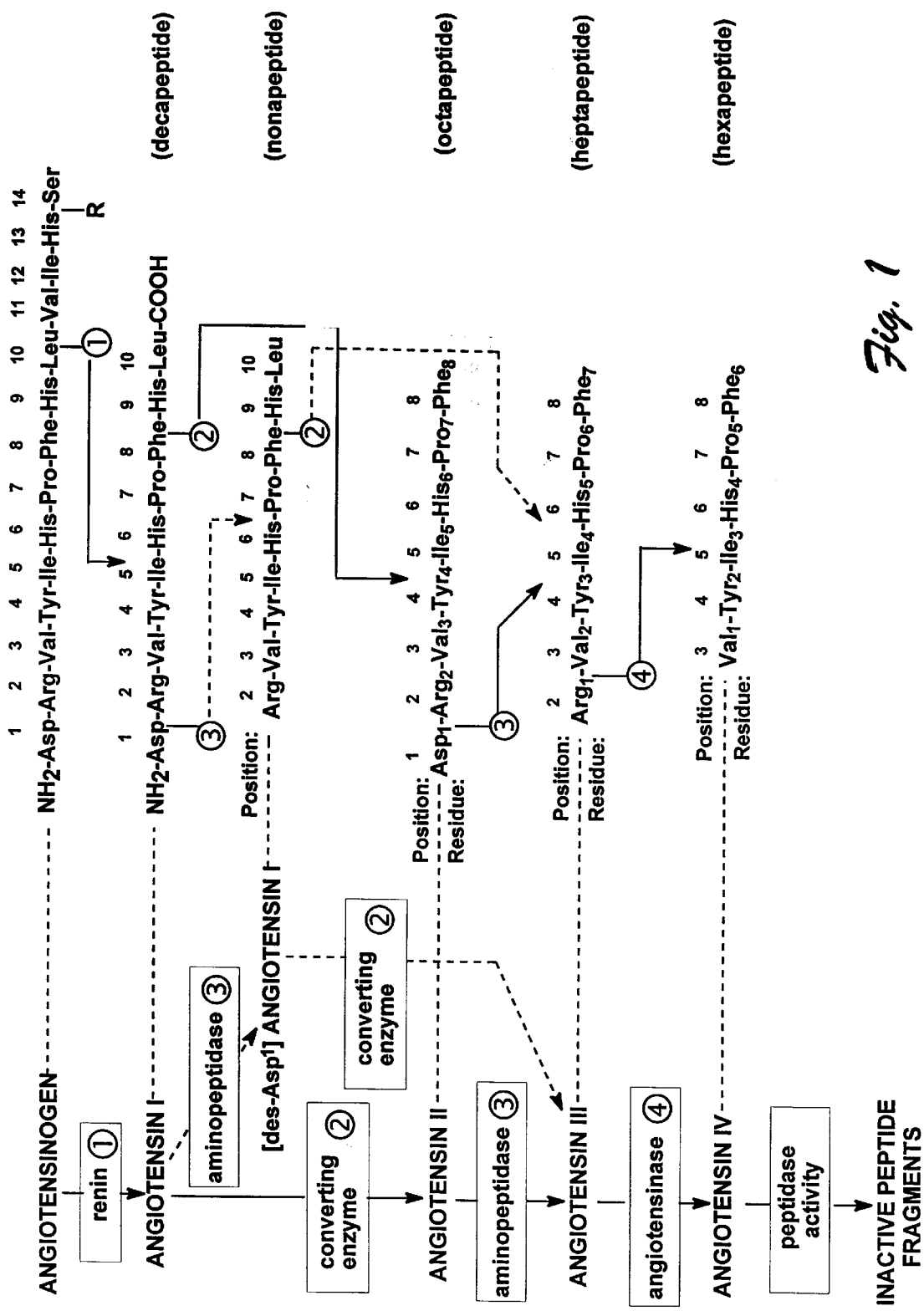
FIG. 1 is a schematic diagram depicting the amino acid sequence of angiotensinogen and its conversion by renin to AI, by angiotensin converting enzyme (ACE) to AII, by angiopeptidase to AIII, and by a novel AIV angioteninase, herein disclosed, to angiotensin AIV (AIV).

As used herein the following terms are intended to mean the following, namely:

"Angiotensinogen" is used herein to refer to a peptide having the sequence $Asp_1Arg_2Val_3Tyr_4Ile_5His_6Pro_7Phe_8His_9Leu_{10}Val_{11}Ile_{12}His_{13}Ser_{14}$,
abbreviated DRVYIHPFHLVIHS (SEQ. ID. NO. 5)

"AI" and "angiotensin I" are terms used to refer to the decapeptide fragment of angiotensin having the N-terminal sequence $Asp_1Arg_2Val_3Tyr_4Ile_5His_6Pro_7Phe_8His_9Leu_{10}$,
abbreviated DRVYIHPFHL (SEQ. ID. NO. 6).

"des-Asp AI", "d-Asp AI" and "Des-Asp angiotensin I" are terms used to refer to an angiotensin polypeptide having the N-terminal sequence $Arg_1Val_2Tyr_3Ile_4His_5Pro_6Phe_7His_8Leu_9$,
abbreviated RVYIHPFHL (SEQ. ID. NO. 7).

"AII" and "angiotensin II" are terms used to refer to an angiotensin, e.g., an octapeptide, having the N-terminal sequence $Asp_1Arg_2Val_3Tyr_4Ile_5His_6Pro_7Phe_8$,
abbreviated DRVYIHPF (SEQ. ID. NO. 2).

"AIII," "Angiotensin III," "Des-Asp AII," and "$AII_{(2-8)}$" are terms used to refer to the heptapeptide fragment of angiotensin having the N-terminal sequence $Arg_1Val_2Tyr_3Ile_4His_5Pro_6Phe_7$,
abbreviated RVYIHPF (SEQ. ID. NO. 3).

"AIV," "angiotensin IV," "$AII_{(3-8)}$," "$AIII_{(2-7)}$," or "Des-Arg AIII" are terms used to refer to the hexapeptide fragment of angiotensin having the N-terminal sequence $Val_1Tyr_2Ile_3His_4Pro_5Phe_6$, abbreviated VYIHPF (SEQ. ID. NO. 1). In the context of usage herein "AIV" refers to physiological angiotensin $II_{(3-8)}$ fragments formed in a variety of animal species. An "AIV peptide ligand" is a ligand capable of binding to an AT4 receptor. AIV is a representative example of an AIV peptide ligand, as are AIV analogs.

"Des-x," also abbreviated "d-x," is used to refer to an amino acid sequence that lacks the amino acid residue "x". Des-Asp AII is used to refer to an angiotensin II lacking the N-terminal Asparagine residue; d-$Val_{(1)}$AIV is used to refer to AIV lacking the valine residue (position 1) at the N-terminus of AIV.

"N-terminal" and "N-terminus" are used interchangeably to refer to the $NH_2$-amino terminus of a peptide. The N-terminal amino acid is the amino acid located at the $NH_2$ terminus of the peptide.

"Peptide" and "polypeptide" are used interchangeably to refer to a serial array of amino acids peptide bonded one to another of at least three amino acids in length to preferably six amino acids in length, but also up to many hundreds of amino acids in length.

"AIV ligand" as used herein refers to a compound that is capable of filling the three-dimensional space in a receptor binding site so that electrostatic repulsive forces are minimized, electrostatic attractive forces are maximized, and hydrophobic and hydrogen bonding forces are maximized. Representative ligands include "AIV peptides" and "AIV analogs". Ligands bind to their specific receptor in a specific saturable manner, e.g., specificity may determined by the ability of an AIV ligand to bind to an AT4 receptor in a manner that is not competitively inhibited in the presence of an excess (e.g., 1000-fold molar excess) of a competitor peptide (e.g., AI or AII).

"AIV peptide" is used interchangeably with "angiotensin IV peptide" to refer to an AIV ligand that is a peptide having, or corresponding to, at least three of the N-terminal ten amino acid residues (preferably three of the N-terminal eight amino acid residues, and most preferably three of the N-terminal six amino acid residues), comprising three amino acids selected from among V, Y, I, H, P, F, L, K, A, H, NVal, NLeu, or Orn; preferably from among V, Y, I, P, K, NVal or NLeu; and most preferably from among V, Y, K, NVal, or NLeu. Representative examples of AIV peptides have an amino acid sequence related to the AIV N-terminal sequence VYIHPFX (SEQ. ID. NO. 8), i.e., by conservative and nonconservative substitutions of amino acids, or by derivatization or covalent modification, (as described below), and wherein X is any non-interfering amino acid. Representative AIV peptides are polypeptides from 3 amino acids in length to many tens of amino acids in length. Other representative examples of "AIV peptides" include peptides that are capable of antagonizing binding of "AIV" to its receptor, i.e., "antagonists" (as defined below), and other "AIV ligands" are capable of binding to the AT4 receptor and exerting effects similar to "AIV", i.e., "agonists" (as defined below).

As used herein the term "AIV analog" is intended to mean a chemical compound that mimics or improves or the electronic, steric, hydrophobic, and 3-dimensional space-filling requirements of the constituent amino acid residues involved in binding of the AIV peptide to the AT4 receptor (e.g., a mimetic chemical AIV composition). AIV analogues may be polypeptides, i.e., having amino acids bonded by peptidic linkages, or may be non-peptides, i.e., having amino acids not bonded by peptidic linkages. Representative examples of AIV analogs include chemical mimetic compounds that are capable of antagonizing binding of AIV to its receptor, i.e., antagonists (as defined below), and other AIV ligands are capable of binding to the AT4 receptor and exerting effects similar to AIV, i.e., agonists (as defined below).

"Agonist" as used herein means an AIV peptide or AIV analog that is capable of spacially conforming to the molecular space filled by an AIV ligand and that is further capable of combining with AT4 receptors to initiate an action that is initiated by a physiological AIV molecule when it binds to its specific AT4 receptors on cells in vivo or in vitro. Representative examples of actions initiated by AIV are illustrated in the Examples. Agonists possess binding affinity for AT4 receptor(s) and intrinsic activity for inducing the activities that are induced following the binding of AIV to AT4 receptor. Representative examples of agonists include VYIHPFX (SEQ. ID. NO. 8), NvaYIHPFX (SEQ. ID. NO. 9), and OrnYIHPFX (SEQ. ID. NO. 10), wherein "X" is used to designate one or more non-interfering amino acids. Representative examples of processes for recognizing agonists are described in Example 4.

"Antagonist" as used herein means an agent that spacially conforms to the molecular space filled by an AIV ligand and that is further capable of combining with the subject AT4 receptor(s) to inhibit, neutralize, impede or reverse, at least in part, an action of physiological AIV when it binds to its specific AT4 receptors on cells. Representative examples of antagonists include KYIHPFX (SEQ. ID. NO. 11), and NLeuYIHPFX (SEQ. ID. NO. 12), wherein "X" is used to designate one or more non-interfering amino acids. Representative examples of processes for recognizing antagonists are described in Example 4.

"AII ligand" as used herein refers to a peptide having the N-terminal amino acid sequence DRVYIHPFX (SEQ. ID. NO. 13) and capable of binding to an AT1 or AT2 AII receptor, where X is any non-interfering amino acid.

"Non-interfering amino acid" as used herein means any amino acid that when introduced into the C-terminus of an AIV peptide ligand does not interfere with binding of the AIV peptide ligand to its specific AT4 receptor.

"AT1" and "AT1 receptor" and are terms used interchangeably to refer to a receptor subtype capable of binding AII.

"AT2" and "AT2 receptor" are terms used interchangeably to refer to a second receptor subtype capable of binding AII.

"AT4 receptor" is the term used to refer to a receptor capable of binding an AIV ligand but not an AI, AII, or AIII ligand.

"AT4 receptor fragments" is a term used herein to refer to portions of the AT4 receptor that are smaller in size than an AT4 receptor isolated from a natural source, e.g., tissues, biological fluids and the like, but remain capable of binding AIV. Fragments may be prepared from an AT4 receptor isolated from a tissue and then subjected to proteolytic degradation or treatment with a chemical such as cyanogen bromide. In the latter case the fragments of the receptor are conveniently purified before use, e.g., by reverse-phase HPLC or immune affinity chromatography. Alternatively, fragments of the AT4 receptor may be prepared by expression of a portion of a nucleotide sequence of a genomic or cDNA clone capable of expressing the AT4 receptor, e.g., a portion of the AT4 nucleotide sequence in an expression plasmid or vector introduced into a cell, wherein the cell manufactures the AT4 receptor fragment and the fragment can be purified (as above). For example, fragments of the AT4 receptor that contain the AIV ligand binding domain of the receptor may be soluble in biological fluids and aqueous solutions and may bind AIV ligand with a greater or less $K_d$ than AT4 receptor under these conditions. The binding affinity, expressed as the $K_d$, of the AT4 receptor fragment for an AIV ligand is about 30 nM to about 0.003 nM, preferably about 1 nM to about 0.01 nM, and most preferably the binding affinity is about 0.5 nM to about 0.01 nM.

"Triggering the AT4 receptor," "activating the AT4 receptor," or "activation of the AT4 receptor" are used interchangeably to refer to conformational and/or structural or activity changes resident in an AT4 receptor following binding of an AIV ligand; e.g., conformational changes may be evident by changes in the near UV spectra of the receptor or changes in the circular dichroism (CD) spectra; structural changes may be evident as covalent modification of the receptor, e.g., by phosphorylation; and, activity changes may be evident as an increase in enzyme activity, e.g., an innate tyrosine kinase activity. A receptor that has interacted with an AIV ligand and has undergone the process of "triggering" is also referred to herein as a "triggered AT4 receptor."

"Substantially purified" as used herein refers to a preparation that contains a peptide, ligand, or receptor that is enriched greater than about 10-fold from the natural source material, e.g., membrane preparations of a tissue, and that also contains less than 5% impurities detectable by one-dimensional SDS-PAGE. The substantially purified AT4 receptor approaches homogeneity at purification levels greater than about 1000×.

The term "AIV angiotensinase" as used herein refers to a dipeptidylpeptidase capable of catalyzing hydrolysis of an arginine-valine peptide bond in an angiotensin, e.g., AI, AII, or AIII, without catalyzing hydrolysis of any of the other peptide bonds in the angiotensin.

"Pressor activity" is used to refer to blood pressure changes induced by an agent, e.g., AII.

As discussed above, the angiotensin field has often been fraught with complexity and conflicting information. During attempts to purify the angiotensin II (AT2) receptor from bovine adrenal cortex, the curious observation was made that as purification proceeded the apparent specificity of the receptor changed. While isolated membranes bound stable AII analogs better than AIII, the solubilized receptor exhibited the opposite order of ligand specificity with AIII binding better than AII. Following purification it became apparent that the receptor had all but lost its ability to bind AII, and was slowly losing its ability to bind AIII, despite taking steps to inhibit proteases. Previously it had been reasoned that 10% hydrolysis of ligand was inconsequential; however, considering the strange behavior of the receptor during purification, the possibility was considered that a portion of the confounding data could be explained by metabolic conversion of the active AII and AIII ligands to previously undiscerned metabolite(s) and interaction of the metabolite (s) with a novel receptor(s). The N-terminus of both AII and AIII are reportedly labile to proteolytic hydrolysis, but previous studies did not satisfactorily control for such hydrolysis. Thus, the possibility was considered that previous studies may have been confounded by the conversion of one ligand (i.e., AI or AII) into another (i.e., AIII or AIV), e.g., mediated by renin, angiotensin converting enzyme (ACE), aminopeptidases, endopeptidases, and/or carboxypeptidases (e.g., through reactions such as those depicted in FIG. 1). Considering the previous studies in this light, physiological activities reportedly triggered by the AII or AIII peptides, on re-examination, seemed to require higher levels of peptides than would be predicted from the physical binding properties of the respective AT1 or AT2 receptors. However, if a previously unrecognized receptor existed it might be reasoned that the relatively high levels of AII or AIII are required to provide precursors for conversion to metabolites that would bind to the novel receptor. To approach this problem an improved assay system was developed. After an exhaustive search, a rapid spin chromatographic technique was developed to separate bound from free ligand, and an assay buffer was discovered that minimized N-terminal degradation of angiotensins. In addition, a stable N-substituted analog of AII was used as a control (i.e., $Sar_1$,$Ile_8$-AII), so that classic AII binding sites (20) could be identified. Under these conditions, the possible conversion of AII to AIII or other metabolites is eliminated, and AII binding sites are accurately identified. When assays were conducted under these conditions to determine what angiotensin fragments bound to bovine adrenal cells, it was surprisingly observed that the $^{125}$I-AII or $^{125}$I-AII radiolabel "specifically bound" to the cells was a hexapeptide fragment of AIII consisting of residues 3 through 8, i.e., $AII_{(3-8)}$. Further, it was discovered that the amount of binding in a given AII (or AIII) preparation was directly proportional to the amount of the hexapeptide in the preparation. The use of $^{125}$I-radiolabeled hexapeptide as the ligand in the receptor assay dramatically increased binding. A reevaluation of binding in purified membrane preparations demonstrated the presence of two different and distinct receptors, one for AII and a second for $AII_{(3-8)}$. Further, neither AII nor $AII_{(3-8)}$ ligand effectively displaced the other. The results, thus, strongly suggested the presence of two distinct receptors, one for AII and a second for $AII_{3-8)}$. Hereinafter $AII_{(3-8)}$ is referred to as AIV and the novel $AII_{(3-8)}$ receptor is referred to as the AT4 receptor. The notion of two separate and distinct receptors was confirmed by solubilizing, isolating, and substantially purifying the AT4 receptor under conditions that did not solubilize the AT2 receptor.

The experimental results described in the Examples, demonstrate for the first time the existence of a distinct high-affinity cellular receptor that specifically binds the hexapeptide fragment of angiotensin AII, i.e., $AII_{(3-8)}$, termed herein angiotensin IV, or simply AIV. The angiotensin AT4 receptor is characterized in the Examples, with respect to structural requirements for ligand binding, species and tissue distribution of the receptor, physiological role of the AIV ligand-AT4 receptor system, intracellular messenger signaling pathways activated by the receptor, conditions for isolation and purification, and molecular size of the receptor.

In one embodiment of the invention, compositions are provided which comprise substantially purified angiotensin AT4 receptor or fragments thereof, that are capable of binding an angiotensin AIV ligand but not an angiotensin AI or AII ligand. The AT4 receptor binds AIV ligands, and does not bind to a peptide having the AII N-terminal sequence, i.e., DRVYIHPF (SEQ. ID. NO. 2). AT4 receptors of the invention are specific for AIV and AIV ligands, and are more fully characterized by the following properties: a) AT4 receptor has a $K_d$ for AIV of about 30 nM to about 0.003 nM, preferably about 3 nM to about 0.01 nM, and most preferably about 1 nM to about 0.1 nM (representative examples of binding properties of AT4 receptors are summarized in Table 1); b) AT4 receptor binds to AIV ligands in a saturable and reversible manner; c) the binding of an AIV ligand to the AT4 receptor is competitively inhibited less than about 1% to about 10% by an angiotensin AII preparation (e.g., $Sar_1Ile_8$-AII) that contains less than 0.1% of an AIV ligand when the competition of AIV binding is measured in the presence of about a 1000-fold molar excess concentration of the competing ligand using the assay conditions described in Example 1.

In a representative embodiment, AT4 receptors having these properties may be isolated from bovine adrenal cortical membranes (e.g., described in Example 1). Isolated AT4 receptors from this source have the kinetic, equilibrium binding, and physical properties set forth below in Example 1. The AT4 receptor of the invention has a molecular size of about 120 kD to about 200 kD on SDS-PAGE, preferably about 140 kD to about 160 kD, and most preferably about 140 kD to about 150 kD. For example, an AT4 receptor of the invention is present in membrane preparations of adrenal glands of most mammalian species (e.g., cow, pig, horse, dog, cat, rabbit, and guinea pig), and, as purified from bovine adrenal membranes, the AT4 receptor has an apparent molecular size of about 146 kDa on SDS-PAGE. AT4 receptors are also expressed in guinea pig aorta, heart, kidney, liver, lung, vascular smooth muscle, pituitary, and uterus, as well as vascular endothelial cells and brain.

TABLE 1

Binding Properties of AIV Receptors

| Animal | Tissue | Preparation | $K_d$ (nM) | $B_{max}$[c] | Example # |
|---|---|---|---|---|---|
| Rabbit | Heart | Membranes | overall: 1.70 | 731 | #2 |
| Guinea pig | Heart | Membranes | site #1: 1.33 | 144 | #1 |
| Bovine | Adrenal Cortex | Membranes | 0.54 | 1030 | #1 |
| | | Sol. Receptor[d] | 0.51 | 87.9 | #1 |
| | Adrenal Medulla | Membranes | — | 397.3 | #2 |
| Bovine | Heart | Vasc. Endo.[e] | overall: 0.7 | 476 | #2 |
| | | | site #1: 26.5 | 6 | #7 |
| | | | site #2: 1.4 | 594 | #7 |
| Bovine | Heart | Aortic Endo.[f] | site #1: 26.9 | 10 | #7 |
| | | | site #2: 4.4 | 434 | #7 |
| Guinea Pig | Brain | Hippocampus g | 0.1 | 306 | #11 |
| | | HSTAh | 0.11 | 168 | #11 |
| | | Cerebellum | 0.2 | 232 | #11 |
| | | Brain Stem | 0.9 | 197 | #11 |
| Guinea Pig | Aorta | Membranes | — | 45.4 | #2 |
| | Heart | Membranes | — | 83.3 | #2 |
| | Kidney | Membranes | — | 22.7 | #2 |
| | Liver | Membranes | — | 28.9 | #2 |
| | Lung | Membranes | — | 56.1 | #2 |

TABLE 1-continued

Binding Properties of AIV Receptors

| Animal | Tissue | Preparation | $K_d$ (nM) | $B_{max}$[c] | Example # |
|---|---|---|---|---|---|
| | Uterus | Membranes | — | 87 | #2 |
| Pig | Adrenal | Membranes | — | 397.3 | #2 |
| Horse | Adrenal | Membranes | — | 70.8 | #2 |
| Dog | Adrenal | Membranes | — | 72.7 | #2 |
| Cat | Adrenal | Membranes | — | 199.6 | #2 |
| Rabbit | Adrenal | Membranes | — | 105.3 | #2 |
| Guinea Pig | Adrenal | Membranes | — | 101.2 | #2 |

[c] $B_{max}$ = maximal binding under equilibrium binding conditions, (fmol/mg protein);
[d] sol. receptor = solubilized receptor;
[e] vasc. endo. = vascular endothelial cells CVEC;
[f] aortic endo. = aortic endothelial cells BAEC;
[g] hippocampus = hippocampal solubilized receptor; and;
[h] HSTA = hypothalamus, thalamus, septum, antereoventral third ventricular area of brain.

The invention further provides AT4 receptor ligands that specifically bind to, activate and/or antagonize the AT4 receptor. The AIV ligands generally comprise at least 3 of the N-terminal amino acid residues of AIV, or analogues or AT4 receptor binding equivalents thereof. The amino acid residues of the ligands may be bonded by peptidic linkages, or may be bonded by non-peptidic linkages. The ligands generally have a $K_d$ for the AT4 receptor below about $3\times10^{-6}$ M.

Generally, the AIV ligands of the invention are based on the structure of AIV. The AIV ligands may be obtained by constructing AIV analogs that have one amino acid substituted for by another of like properties, i.e., a neutral polar amino acid for another neutral polar (e.g., G, A, V, I, L, F, P, or M), a neutral nonpolar amino acid for another neutral nonpolar (e.g., S, T, Y, W, N, Q, C), an acidic amino acid for another acidic (e.g., D or E), or a basic for a another basic (e.g., K, R, or H). The AIV ligands may alternatively be obtained by constructing an AIV analog that is covalently modified, e.g., wherein an amino acid residue is substituted by amidation, adenylation, methylation, acylation, phosphorylation, uridylation, fatty-acylation, glycosylation, and the like to form a "substituted amino acid residue". In addition, the AIV ligands of the invention may contain one or more stereoisomers of the constituent amino acids residues; i.e., may contain one or more substituted or unsubstituted amino acid residues in the D-configuration.

In other embodiments, the invention provides angiotensin AIV ligands and ligand compositions that include AIV analogs, AIV peptide derivatives, and covalently modified AIV peptides, all of which are capable of binding to an angiotensin AT4 receptor. AIV ligands of the invention are generally defined by the formula $$R_1—R_2—R_3—X$$

wherein $R_1$ is a substituted or unsubstituted amino acid residue having a neutral or positively charged aliphatic side chain $Z_1$, said amino acid being selected from among V, I, L, A, G, F, P, M, K, norvaline, norleucine, and ornithine;

$R_2$ is a substituted or unsubstituted neutral nonpolar amino acid selected from the group consisting of Y, W, N, Q, F, or C;

$R_3$ is a substituted or unsubstituted neutral polar amino acid selected from the group consisting of G, A, V, I, L, F, P, or M; and X is nothing, $R_4$, $R_4$—$R_5$, or $R_4$—$R_5$—$R_6$, wherein $R_4$ is a substituted or unsubstituted basic amino acid residue selected from the group consisting of K, R and H, $R_5$ is a substituted or unsubstituted neutral polar amino acid residue selected from the group consisting of G, A, V, I, L, F, P, and M, and $R_6$ is a substituted or unsubstituted neutral polar amino acid residue selected from the group consisting of G, A, V, I, L, F, P, M, and polyamino acid residues containing one or amino acid residues which do not prevent binding of the AIV ligand with the AT4 receptor.

Thus, the AIV ligands of the invention are generally amino acid chains that contain 3, 4, 5, or 6 amino acid residues corresponding to the N-terminal 3, 4, 5 or 6 amino acid residues of AIV (the polypeptide, VYIHPF (SEQ. ID. NO. 1), or may optionally extended at the C-terminal end with one or more amino acid residues that do not prevent binding, due to spatial, conformational, electrostatic or other considerations, to the AT4 receptor. The amino acid residues may be linked in the amino acid chain by peptidic linkages to form peptides, or the AIV ligands of the invention may contain one or more non-peptidic linkages, such as methylene or C—N linkages, to enhance metabolic stability or other properties of the AIV ligands, as is hereinafter further described. Representative AIV ligands of the invention include, but are not limited to C-terminal truncated forms of AIV, such as $AIV_{(1-5)}$, $AIV_{(1-4)}$, and $AIV_{(1-3)}$; stereoisomerically modified forms of AIV, such as D-$H_4$ AIV, D-$P_5$ AIV, and D-$F_6$ AIV; full or truncated forms of AIV with modified amino acid residues, such as $G_4$ AIV, $G_5$ AIV, $G_6$ AIV, $Nle_1$ AIV, $K_1$ AIV, F AIV, $I_1$ AIV, $P_1$ AIV, $Nva_1$ AIV, $Orn_1$ AIV, $Y_6$ AIV, $I_6$ AIV, NleYI, KYI, and NleYI, derivatives of AIV with one or more non-peptide linkages between amino acid residues, such as Nle $al^1$ AIV (wherein the designation $al^1$ refers to a methylene —$CH_2$— linkage between the amino acid residue in position 1 (Nle) and the amino acid residue in position 2 (Y)), Nle $al^1$ $Val^3$ AIV, $Kal^1$ $Val^3$ AIV, $Kal^1$ AIV, $Val^1$ AIV, $Val^3$ AIV, and $Val^1$ $Val^3$ AIV, and substituted AIV ligands, such as propanoyl-N $orn_1$ AIV, O-me $Y_2$ AIV, isobutyl-N $orn_1$ AIV, N-me $I_1$ AIV, NleYI amide, KYI amide, NleYNle amide, NleYNva amide, Nle al N-me YI amide, benzyl $C_1$ AIV and the like, The physical properties of the AT4 receptors that determine binding of the AIV ligands were mapped using synthetic peptides and analogs, as described below in detail in the examples. The structure of the N-terminus of AIV is most important for high affinity binding of an AIV peptide to an AT4 receptor. The AT4 receptor binding site is a coordinated multidomain binding site wherein binding in one subdomain may be excluded by high affinity binding at a second subdomain through an induced conformation change in the AT4 receptor binding site hydrophobic pocket subdomain. At least three binding site subdomains in the AT4 receptor were mapped using synthetic peptides and analogs. The binding site is stereospecific at a first subdomain for L-Valine in N-terminal amino acid position 1 ($Val_1$) of AIV; at a second subdomain for L-Tyrosine in position 2 ($Tyr_2$) of AIV; and at a third site for L-isoleucine ($Ile_3$) in position 3 in AIV. The results suggest that $Val_1$ in AIV may interact laterally with the walls of the groove of the receptor while $Tyr_2$ in AIV may interact with the receptor binding site through van der Waals forces and hydrogen bonding. AIV peptides having a weak hydrophobic amino acid at the N-terminus with an aliphatic side chain (e.g., KYIHPF (SEQ. ID. NO. 14), NleYIHPF (SEQ. ID. NO. 4), OrnYIHPF (SEQ. ID. NO. 15)) bind to the AT4 receptor with a higher binding affinity than AIV (binding of KYIHPF (SEQ. ID. NO. 4) is 50-fold higher than AIV, and NleYIHPF (SEQ. ID. NO. 4) has a $K_i$ of about $10^{-12}$ M). N-terminal extension of AIV is incompatible with binding, as is deletion of the N-terminal valine ($Val_1$) residue. Deletion of $Val_1$ reduced binding affinities 1000-fold; substitution of $Val_1$ with Sar decreased binding affinity; addition of D-arginine to the N-terminal $Val_1$ reduced affinity for the receptor by 100-fold. The receptor binding site domain of the AT4 receptor contains a hydrophobic pocket conforming closely to the space filled by norleucine (i.e., engaging the $Val_1$ residue of AIV) and in close apposition with a negatively charged residue (i.e., engaging the primary amine of the N-terminus of $Val_1$). Removal of the N-terminal amino group decreases by 1000-fold.

The C-terminus of the AIV peptide is relatively less important in the receptor binding and C-terminal extension of AIV ligands of the invention with "X" is allowed. However, removal of both the $Pro_5$ and $Phe_6$ residues from AIV reduced binding affinity by about 21-fold to a $K_i$ of 500 nM. The C-terminus of the AIV peptide may determine receptor subtype specificity of binding.

In addition, it has been found that AT4 receptors isolated from bovine adrenal cortical membranes do not effectively bind AIV peptides synthesized with an N-terminal extension with Sar or GABA. Nor do the illustrative AT4 receptors effectively bind peptides having the N-terminal L-Val replaced with D-Val or Sar. Also, removal of the N-terminal L-Val from AIV all but eliminates binding to the AT4 receptor. AT4 receptors of the invention have a receptor binding site that is stereospecific for L-Valine. In one illustrative example, D-$Val_1$YIHPF (SEQ. ID. NO. 16) has 1000-fold lower binding affinity for the AT4 receptor than L-$Val_1$YIHPF (SEQ. ID. NO. 1). The illustrative AT4 receptor isolated from bovine adrenal cortical membranes contains a binding site that prefers weak hydrophobic amino acids in the number 1 position (i.e., $R_1$) of the AIV ligand, i.e., increasing hydrophobicity by replacing $Val_1$ with Phe (i.e., $F_1$YIHPF; SEQ. ID. NO. 17) decreases binding affinity 4-fold, but replacement of $Val_1$ with another weak hydrophobic amino acid (i.e., $I_1$YIHPF; SEQ. ID. NO. 18) results in only a slight change (an increase) in binding affinity. For high affinity binding of an AIV peptide to an AT4 receptor the structure of the N-terminal neutral polar amino acid is most important. N-terminal extension is incompatible with binding, deletion of the terminal valine residue eliminates binding ($K_i > 10^{-6}$), substitution with Sar decreased binding affinity, substitution with Ile results in equivalent binding, substitution with Phe resulted in a 5–10-fold decrease in the affinity of binding, Pro-substituted AIV peptides bind with 100-fold lower affinity, Lys-substituted AIV peptides bind with 10-fold higher affinity, and AIV ligands having a norleucine in the number 1 position (also abbreviated herein Nle, NLe, NLeu, $NLeu_1$, or $Nle_1$) bound with 1000-fold higher affinity.

The interaction between the AT4 receptor binding site and AIV ligand may be dictated by requirements for an AIV ligand containing a flexible aliphatic carbon side chain, (i.e., as opposed to a relatively rigid aromatic ring), rather than by the degree of hydrophobicity of the side chain. In a representative example, substitution of $Val_1$ with $Asp_1$ (i.e., to form $A_1$YIHPF; SEQ. ID. NO. 19) results in an analog with no binding affinity for the AT4 receptor (i.e., has a $K_d > 10^{-6}$ M). Further, the AT4 receptor binding sites of the invention may prefer a flexible aliphatic carbon side chain having 4 carbon atoms that lack a positively charged residue. Heptanoyl$_1$ AIV with a 5 carbon side chain has reduced affinity as compared to $Nle_1$ AIV. In a representative example, Nle$_1$YIHPF (SEQ. ID. NO. 4) has higher binding affinity for an illustrative AT4 receptor than Lys$_1$YIHPF (SEQ. ID. NO. 14), which was higher than NVal$_1$YIHPF, which is in turn higher than Orn$_1$YIHPF (SEQ. ID. NO. 15). The AIV peptide ligands of the invention having norleucine substituted for Val$_1$ (i.e., Nle$_1$YIHPFX; SEQ. ID. NO. 12) are partial agonists of VYIHPFX (SEQ. ID. NO. 8) binding to the subject AT4 receptor and have an apparent K$_i$ of about $1\times10^{-12}$ M.

The AT4 receptor binding site interacts specifically with the N-terminal amino acid residue (i.e., R$_1$), and the latter interaction is specific with respect to both absolute space occupancy volume (i.e., of the receptor binding site) and charge (i.e., of the AIV ligand). In representative examples, methylation of isoleucine in Ile$_1$ of I$_1$YIHPF (SEQ. ID. NO. 18) (i.e., to form CH$_3$—I$_1$YIHPF; SEQ. ID. NO. 20) reduces affinity of the illustrative receptor for the peptide by 67-fold; substitution of the Val$_1$ primary amine (NH$_3$) with a secondary amine (—NH—; in this case by substituting Pro$_1$ for Val$_1$, to form PYIHPF; SEQ. ID. NO. 21) reduces the affinity of binding to the illustrative receptor by 8-fold; substitution of Val$_1$ with benzoic acid or 6-amino-hexanoic acid gives peptides with a K$_i$>1 mM; and, replacing Val$_1$ with GABA (gamma-amino butyric acid; to form GABA-YIHPF; SEQ. ID. NO. 2) decreases binding affinity by 250-fold for the illustrative receptor.

The AT4 receptor binding sites of the invention also appear to be stereospecific for Tyr$_2$ (i.e., Y) in the R$_2$ position of the subject AIV peptide ligands. In representative examples, substitution of D-Tyr$_2$ or Phe$_2$ (with a benzyl ring) for Tyr$_2$ (with a phenolic ring) results in analogs (i.e., V[D-Y$_2$]IHPF (SEQ. ID. NO. 23), or VF$_2$IHPF (SEQ. ID. NO. 24), respectively) with very low affinity for the illustrative adrenal cortical receptor. Phenolic side chains in the Tyr$_2$ residue may also interact with residues in the subject AT4 receptors through hydrophobic and/or hydrogen-bonding.

The AT4 receptor binding sites of the invention tolerate replacement of the V$_1$—Y$_2$ peptide bond with a non-carbonyl bond that has a similar bond length, but is non-planar and has a non-rigid carbon-nitrogen bond. The latter replacement bond may preferably be resistant to proteolytic hydrolysis thereby conferring additional stability on the AIV ligand and enhancing utility in therapeutic compositions for oral delivery. In a representative example, replacement of the V$_1$—Y$_2$ peptide bond with a methylene bond reduces receptor binding affinity by only 5-fold; and, replacement of both the V$_1$—Y$_2$ and I$_3$—H$_4$ peptide bonds with methylene bonds results in N—V$_1$—CH$_2$—NH—Y$_2$V$_3$—CH$_2$—NH—H$_4$P$_5$F$_6$—C (SEQ. ID. NO. 25) (also referred to herein as Val$_1$ Val$_3$ AIV or divalinal AIV) that has an affinity equal to or better than VYIHPF (SEQ. ID. NO. 1).

The binding site of the AT4 receptors of the invention is a coordinated, multidomain binding site wherein binding in one subdomain of the binding site may be enhanced or inhibited by binding at a distant second subdomain. In one representative example, substitution of Ile for Phe at the R$_6$ position of VYIHPF$_6$ (SEQ. ID. NO. 1) results in an analog (i.e., VYIHPI$_6$ (SEQ. ID. NO. 1)) that binds to AT4 receptor (i.e., through the V$_1$ subdomain sites) with a higher affinity than the parent VYIHPF (SEQ. ID. NO. 1) molecule. In a second representative example, substitution of Ile$_6$ for Phe$_6$ in KYIHPF$_6$ (SEQ. ID. NO. 14) results in an analog (i.e., KYIHPI$_6$; SEQ. ID. NO. 26) that binds to the receptor (i.e., through the V$_1$ subdomain site) with a lower affinity than the parent KYIHPF$_6$ (SEQ. ID. NO. 14) molecule. The C-terminus of the subject AIV peptide ligands appears to be relatively less important in receptor binding. In representative examples disclosed below, deletion of the C-terminal Phe$_6$ from VYIHPF (SEQ. ID. NO. 1) (i.e., to form V$_1$Y$_2$I$_3$H$_4$P$_5$; SEQ. ID. NO. 27) does not alter binding significantly; C-terminal extension with histidine does not alter binding (i.e., to form V$_1$Y$_2$I$_3$H$_4$P$_5$F$_6$H$_7$; SEQ. ID. NO. 28); and, addition of both his and leu reduces affinity only 2-fold (i.e., V$_1$Y$_2$I$_3$H$_4$P$_5$F$_6$H$_7$L$_8$; SEQ. ID. NO. 29). Truncation of the C-terminus, i.e., at the R$_5$ position decreases binding. In a representative example removal of Pro$_5$ from VYIHP (SEQ. ID. NO. 27) to give VYIH (SEQ. ID. NO. 30), decreases binding 21-fold, and given an analog with a K$_i$>500 nM. The binding site domains of the subject AT4 receptor of the invention recognize the N-terminus of the subject AIV peptide ligands with a high degree of specificity and while the receptor interacts less closely with the C-terminus this region of the subject AIV ligand may determine receptor subtype specificity.

In another embodiment of the invention, antagonists of AIV are provided that bind to the AT4 receptor. Presently particularly preferred antagonists of the invention include the non-peptide divalinal AIV and the C-terminal substituted tripeptide NleYi amide, as described in Example 4, although other antagonists will be readily apparent from the data and disclosure set forth herein.

Other aspects of the invention include processes for identifying AIV peptide ligands, i.e., by structural examination of the receptor binding requirements of test preparations (e.g., with respect to both blocking and/or promoting binding of the alternative peptide) to AT4 receptors such as those in heat-treated purified membrane preparation that are free of peptidase activity and devoid of other angiotensin receptors, i.e., AT1 or AT2 receptors. (Examples of such heat-treated membrane preparations and assay methods are provided in the examples, below.) Those skilled in the art will recognize that the binding activity of any AIV peptide can be tested, e.g., using the receptor binding assays described herein, and that analogs, AIV peptide derivatives, and covalently modified AIV peptide or non-peptide ligands may exhibit activity as antagonists, agonists, promoters, or enhancers of AIV binding to its AT4 receptor. Candidate AIV peptides may be prepared with substitution of other L-amino acids having different steric, electronic, and hydrophobic character for the L-Val in the natural AIV ligand. Skilled artisans will also recognize that a similar approach may be used to characterize further the role of C-terminal amino acid residues in binding of a peptide to the AT4 receptor, (i.e., other than the C-terminal P and F). Substitutions and modifications of internal amino acids (i.e., Y, I, or H) can also be examined by constructing the appropriate series of D-substituted, covalently modified, derivatized, or deleted peptides. The first or second messenger intracellular pathways triggered in cells by interaction of an AIV ligand with an AT4 receptor may be used to test a series of peptides, analogs, derivatives, or covalently modified AIV peptides for their ability to bind to the AT4 receptor and trigger the intracellular signal. For instance, activities such as tyrosine kinase, guanylate cyclase, Protein kinase C, Ca$^{++}$ flux changes, phospholipase C (PLC) activity, or prostaglandin or endocrine or exocrine hormone release from cells, may be monitored to determine whether the peptide triggered the AT4 receptor, and the receptor then signaled an increased or decreased activity in the cell.

In all cases, the AIV peptides, AIV analogs, agonists and antagonists, and derivatives and covalently modified forms of the AIV peptides of the invention are recognized by their ability to bind the AT4 receptor with an equilibrium dissociation constant ($K_d$) below $3\times10^{-6}$ M, more preferably below $3\times10^{-8}$ M and most preferably below $3\times10^{-9}$ M, and to a low binding affinity for AT1 and AT2 receptors with a $K_d$ greater than $1\times10^{-6}$ M.

In still other embodiments of the invention, processes are provided for identifying and characterizing a physiological effect of an angiotensin AIV peptide by assaying the effect(s) of the peptide on a selected in vitro cellular process. For instance, to identify and characterize the physiological effects of an AIV peptide on blood flow, it may be convenient to assay renal blood flow, or in vitro cellular processes of endothelial cells and/or vascular smooth muscle cells. To identify and characterize a physiological effect of an AIV peptide or cardiac ventricular hypertrophy, assays may examine the effects of an AIV peptide on growth of a cardiomyocytes in vitro. The processes disclosed herein are also useful in identifying how the in vitro activities of physiological AIV may be blocked or promoted by AIV peptides, AIV analogs, or derivatives or covalently modified forms of AIV peptides, as well as AT4 receptor fragments and the like. Representative examples of useful assays for identifying the subject AIV peptide ligands and AIV ligands are provided in the examples.

As used herein the term "cellular processes" is intended to mean biological activities that may be measured in vitro or in vivo by quantitative and/or qualitative assay. For example, cell growth or metabolism may be measured (e.g., radiolabeled amino acid synthesis into protein, glycolytic activity, oncogene expression, and the like); or, proliferation (e.g., $^3$H-thymidine synthesis into DNA); or, marker expression (e.g., mRNA by Northern, protein by Western blot, antigen by immunoassay, in vitro selectable drug-resistance marker by cell survival in toxic drug, and the like); or, electrical activity (e.g., in neural cells).

Other aspects of the invention provide compositions and methods for promoting or inhibiting cellular activity of neural cells, e.g., neural motor, cognitive or analgesic activity of neural cells in the brain. The effect of the AIV compounds on motor activity may be observed by examining alterations in activity as measured with open-field techniques. The cognitive activity may be observed by passive avoidance testing, Morris swimming maze performance, and various operant tasks. To assay the effects of an AIV composition on a cellular process it may be useful, for example, to measure cellular processes before and after addition of AIV peptides to make comparative observations in parallel cell cultures. In this manner antagonists, agonists, inhibitors, promoters, enhancers, and the like may be identified and characterized with respect to their physiological effects in vitro and possible effects in vivo.

When used for therapeutic purposes, the route of delivery of the AIV ligands, AT4 receptor, AT4 receptor fragments, and AIV monoclonal antibodies of the invention is determined by the disease and site where treatment is required. For example, the compounds or compositions of the invention may be applied topically, or by intravenous, intraperitoneal, intramuscular, subcutaneous, intranasal and intradermal injection, as well as by intrabronchial instillation (e.g., with a nebulizer), transdermal delivery (e.g., with a lipid-soluble carrier and skin patch), gastrointestinal delivery (e.g., with a capsule or tablet), intracerebroventricularly (icv) into brain, or intraspinally into cerebrospinal fluid (CSF).

The preferred therapeutic compositions will vary with the clinical indication. Some variation in dosage will necessarily occur depending on the condition of the patient being treated, and the physician will, in any event, determine the appropriate dose for the individual patient. The effective amount of AIV ligand per unit dose depends, among other things, on the particular ligand employed, on the body weight and the chosen inoculation regimen. A unit dose of ligand refers to the weight of ligand without the weight of carrier, when a carrier is used. An effective treatment will be achieved in the microenvironment of the cells at a tissue site as the concentration of AIV ligand approaches a concentration of $10^{-5}$ M to $10^{-11}$ M. Since the pharmacokinetics and pharmacodynamics of these agents will vary in different species and different patients, the most preferred method to achieve the therapeutic concentration is to gradually escalate the dosage and monitor both the biological effects and the concentration in the biological fluids (e.g., through the use of a diagnostic immunoassay, or radioisotopic or chemical label). The initial dose, for such an escalating dosage regimen of therapy, will depend upon the route of administration. For intravenous administration, for an agent with an approximate molecular weight of 10,000 daltons, an initial dosage of approximately 70 mg/kg body weight is administered and the dosage is escalated at 10-fold increases in concentration for each interval of the escalating dosage regimen. Therapeutic efficacy in this example is achieved at 0.7–70 mg/kg body weight of the theoretical 10,000 dalton peptide.

The compounds may be administered alone or in combination with pharmaceutically acceptable carriers, in either single or multiple doses. Suitable pharmaceutical carriers include inert solid diluents or fillers, sterile aqueous solutions, and various nontoxic organic solvents. The pharmaceutical compositions formed by combining the AIV ligands or receptor fragments with the pharmaceutically acceptable carrier are then readily administered in a variety of dosage forms such as tablets, lozenges, syrups, injectable solutions, and the like. These pharmaceutical carriers can, if desired, contain additional ingredients such as flavorings, binders, excipients, sweetening or flavoring agents, colored matter or dyes, emulsifying or suspending agents, and/or. For parenteral administration, solutions of the AIV ligand or receptor fragment in sesame or peanut oil or in aqueous propylene glycol may be employed.

The present invention further provides processes for isolating inhibitors of an AT4 receptor-AIV ligand interaction by: a) selecting a cell type that expresses the AT4 receptor; b) adding an AIV ligand to a control culture of said cells; c) adding the AIV ligand and a putative inhibitor to a second test culture of the cells; and d) measuring the level of binding of the AIV peptide to the cells in said second test and control cultures. In the case that an inhibitor is present in the preparation, the level of binding in the test culture is lower than that in the control culture. (An example of such a process is provided in Example 1). Those skilled in the art will recognize that this process may be used to identify an inhibitor of an AT4 receptor-AIV ligand interaction in chromatographic fractions and the like during solubilization, isolation, and purification of said inhibitors, and that the subject inhibitors may act as agonists or antagonists of the action of AIV induced when AIV binds to its specific AT4 receptor.

In other embodiments the invention provides an AIV angiontensinase enzyme capable of hydrolyzing a peptide bond between an arginine and a valine residue in an angiotensin polypeptide, e.g., a polypeptide with a DR\VYIHPF (SEQ. ID. NO. 2) N-terminal sequence, wherein "\" indicates the proteolytic cleavage site that gives rise to an AIV peptide, i.e., with an N-terminal sequence related (as described above) to the amino acid sequence VYIHPF (SEQ. ID. NO. 1). Isolation and substantial purification of AIV angiotensinase may be conveniently accomplished, for example, by preparing an affinity resin having a non-cleavable or slowly-cleavable AIV ligand covalently bound to the resin, e.g., chemically modified derivatives of a peptide in an amino acid sequence selected from among DRVYIHPF (SEQ. ID. NO. 2), DRVYIHP (SEQ. ID. NO. 2), DRVYIH (SEQ. ID. NO. 2), DRVYI (SEQ. ID. NO. 2), DRVY (SEQ. ID. NO. 2), DRV, RVY, or NRVYIHPF (SEQ. ID. NO. 31), NRVYIHP (SEQ. ID. NO. 31), NRVYIH (SEQ. ID. NO. 31), NRVYI (SEQ. ID. NO. 31), NRVY (SEQ. ID. NO. 31), NRV. Operationally, the peptide useful in this assay is selected based on its ability to bind the AIV angiotensinase and to be resistant to cleavage by the enzyme. A test preparation of a cellular or tissue extract (or a biological fluid sample) is next chromatographed through the affinity resin; the bound polypeptide(s) is eluted, e.g., at low pH and high salt (e.g., pH2–3, and 2–3 M NaCl, and the like), or the bound polypeptide is eluted by adding an excess of AIV ligand. The presence of the AIV angiotensinase in the eluate can be determined by assaying for the ability of the column eluate to catalyze hydrolysis of an Arginine-Valine peptide bond in an angiotensin peptide (e.g., AIII), and subsequently confirming that the sequence of the product of the reaction has a Valine residue at N-terminal amino acid and an AIV peptide sequence.

The novel of AIV ligand-AT4 receptor system of the invention is useful in a complementary or antagonistic role to AII in mediating long-term effects of angiotensins, and in modulating the effects of AI, AII, or AIII on cells. Although not being limited by any particular theory of action, it is believed that: 1) AIV is derived from AII (or AIII) directly (e.g., through the action of a specific AIV angiotensinase, and other peptidases); 2) AIV is very labile and will accumulate at physiologically significant concentrations only when high levels of AII are present at the target site; 3) the AT4 receptor is specific for AIV ligand (with accompanying low affinity for the parent peptide, AIII). Under certain conditions, AIV begins to accumulate at angiotensin target tissues as the AII levels rise. When AIV concentrations rise to near 0.5 nM (i.e., the $K_d$ of the receptor) auxiliary processes which modify the acute action of AII will be engaged. These actions will be mediated by an intracellular signaling system(s) different from that employed by AII. The activation of such an intracellular system may potentiate or antagonize the target cell's short-term response to AII. One physiological function of the AT4 receptor-ligand system may be to impart a longer-term response to high-level or chronic angiotensin stimulation in a tissue. Studies support the hypothesis that the AIV ligand-receptor system possesses the characteristics set forth above and is, therefore, in a position to serve a short- or long-term modulatory role on the activities of AII. Studies using bovine adrenal tissues have shown that the AT4 receptor is specific, with almost no affinity for AII. In addition, AIV is metabolized/hydrolyzed in bovine adrenal homogenates at 200 times the rate of AII and 4 times the rate of AIII. Data suggests that AIV may be derived directly from AII by action of a dipeptidylaminopeptidase, termed herein AIV angiotensinase.

The location of AT4 receptor sites in groups of cells in tissues allows a skilled artesian to predict likely functions for the AT4 receptor in different tissues. In addition, it will be recognized that many activities previously attributed to the action of AII (and/or AIII) may be triggered or regulated instead by the AT4 receptor-ligand interaction. For example, it is likely that AIV ligand acts as a negative-feedback agent thus enabling tighter control on the aldosterone release process. The AIV ligand-receptor system may also be associated with a previously inexplicable up-regulation of the angiotensin receptor seen following chronic AII exposure of cells in vitro. Still other functions attributed to AII that may be mediated instead by the AIV ligand-receptor system include altering the release of catecholamines from adrenal medullary cells or regulating adrenal blood flow. It is, therefore, likely the AIV ligand-receptor system modulates (i.e., increases or decreases) either the acute and/or the long-term synthesis and release of chromaffin catecholamines, e.g., by acting to stimulate intracellular expression of tyrosine hydroxylase (the rate limiting enzyme in the synthetic pathway).

Experiments described below demonstrate that the AT4 receptor-ligand system may have a role as a mediator of long-term angiotensin effects on endothelial cells (e.g., cell growth; Example 5). AIV ligand-receptor interactions also appear to activate processes in endothelial cells that are complementary or antagonistic to those activated by AII. For instance, some of the AIV ligands that are embodiments of the invention are useful for increasing blood flow (e.g., renal blood flow as demonstrated in the examples).

Because of the widespread distribution of AT4 receptors in many tissues (see examples, below) it is impossible within the scope of this specification to detail every one of AIV's actions in angiotensin-sensitive tissues. However, representative data is provided in the following examples (below), for the physical characteristics of AT4 receptors (see esp. Example 1), for AT4 receptor tissue distribution and species distribution (see esp. Example 2), for physiological functions of AIV peptide ligands and AT4 receptors in controlling renal blood flow, for the cellular biology of AIV ligand-AT4 receptor interactions (e.g., second messenger pathways, G-proteins, phosphorylation, intracellular $C^+$, phosphoinositide turnover, and guanylate cyclase activity), for vascular effects on venular and aortic endothelial cells and vascular smooth muscle cells and G-protein linkage of certain AIV-receptors, for endocrine effects on adrenocortical cell catacholamine release for effects on cardiac myocytes (i.e., cardiocytes), and for characterization of brain AT4 receptors (e.g., in hippocampal cells and in cerebellum, hippocampus, piriform cortex, Par ½, Fr ½, caudate putamen, HDB, thalamus, and inferior colluculus), as well as, neurological effects of intracerebroventricular injection of AIV (e.g., on learning and memory). The disclosures made herein for assays and processes relating to endothelial cells, adrenal cortical cells, cardiac myocytes (cardiocytes), and vascular smooth muscle cells are discussed briefly below.

As shown in the examples AIV is active in endothelial cells in enhancing cellular proliferation (as evidenced by thymidine incorporation) and stimulating production of endothelial cell relaxing factor (EDRF). These results also show the non-interaction of G-proteins with vascular AT4 receptors in bovine aortic or coronary venous endothelial cells. The results set forth in the Examples further identify a role for the AIV ligand-AT4 receptor interactions in triggering normal and/or hyperplastic growth of endothelial cells in sites of tumors or traumatic or wound injury, and angiogenesis, and a therapeutic use for AIV analogs, agonists, antagonists, and derivatives and covalently modified AIV peptide ligands that are capable of inhibiting vascular smooth muscle cell growth in such hyperplastic states while at the same time promoting endothelial cell growth. The agonist compositions are also useful for encouraging endothelial cell growth, e.g., in wound sites; antagonists for discouraging vascularization in tumor sites. In addition, the AT4 receptor-ligand system may play a role in triggering vasodilation through a selective effect on subpopulations of endothelial cells that exist in particular vascular beds (e.g., in the heart, lung, liver, kidney, brain and the like). As shown in the examples, increased renal blood flow occurs in rats following infusion of AIV ligands and taken together with the demonstrated ability of AIV to stimulate EDRF production in vascular endothelial cells, the AIV ligand-receptor system mediates actions of angiotensin that fall within the bounds of cardiovascular regulation and body water homeostasis. Thus, therapeutic uses for AIV analogs, AIV agonists and antagonists, and derivatives and covalently modified AIV peptide ligands include promoting renal blood flow (e.g., in chronic kidney diseases) or, alternatively, inhibiting renal blood flow (i.e., using inhibitors and antagonists of AIV), e.g., in conditions of hyperacute renal dysfunction and water loss, or during renal surgical procedures.

In cardiac myocytes (also termed herein "cardiocytes") it has been speculated previously that angiotensin II may somehow be involved in the development of left ventricular hypertrophy since patients treated with angiotensin converting enzyme (ACE) blockers to block blood pressure changes, show less tendency to develop left ventricular hypertrophy (25,26). As shown herein, AIV antagonizes the hypertrophic action of AII. Accordingly, the control of cardiocyte growth may be regulated endogenously by a balance between the activating action of AII and the inhibiting action of AIV. It is further believed that AIV and AIV agonists will be effective in blocking the development of, and reversing the effects of, left ventricular hypertrophy in patients. Additionally, it is believed that the action of ACE inhibitor is due not to their inhibition of AII synthesis but to their ability to enhance the synthesis of AIV ligands such as results from the shunting of precursors from the AII synthetic pathway into the AIV pathway. Contrary to current popular belief, the beneficial effect of ACE inhibitors in treating cardiac hypertrophy may be due to ACE inhibitor enhancement of the formation of AIV.

The data presented herein also indicates that AII and AIV operate by separate receptors employing different intracellular signaling systems. It has been reported that ACE inhibitors may have a beneficial effect in reducing cardiac hypertrophy through effects at the level of AII or AIII. Considering the results disclosed herein it is most likely that the long-term effects previously attributed to decreased AII may in fact be mediated by the interaction of increased levels of endogenous AIV ligands with the AT4 receptor. Further, it is most likely that the antagonists and agonists of AIV ligands, disclosed herein, will provide improved pharmaceutical compositions for treating cardiac hypertrophy attributable to the renin-angiotensin system, e.g. ventricular hypertrophy. The inventors believe that the interaction between AIV and the AT4 receptor may trigger the receptor and inhibit growth in cardiomyocytes.

In adrenal cells angiotensin AII's role in the regulation of aldosterone release from the adrenal cortex is reportedly well established (27). As shown herein, certain activities (such as adrenocortical cell growth), previously attributed to AII or ATI, are actually activated following AIV ligand binding to the AT4 receptor. AII (and AIII) reportedly stimulates aldosterone release from adrenal glomerulosa cells. The disclosure, herein, of high levels of AT4 receptors in adrenal cortical cells (Examples 1–2) suggests a possible role of AIV ligand (i.e., rather than AII or AIII) in triggering AT4 receptors on adrenal cells to inhibit AII-mediated aldosterone release. Another role of AT4 receptors in adrenocortical cells may be to up-regulate the threshold level of AII ligand required to trigger a cellular response by regulating the levels of cellular AT1 and/or AT2 receptors and/or to regulate adrenal blood flow.

In addition to being found in high concentrations in the adrenal cortex, AT4 receptors are found at even higher levels in the adrenal medullary cells where AII has previously been reported by others to potentiate catecholamine release. AIV ligand may modulate release of catecholamines (i.e., increase or decrease the release) acutely (or possibly even long-term, e.g., by triggering the AT4 receptor and thereby stimulating increased or decreased expression of tyrosine hydroxylase, the rate-limiting enzyme in catecholamine synthesis.

In vascular smooth muscle cells the role of AIV and its specific receptor appears to be similar to that articulated above for AIV in cardiocytes: AIV may act to inhibit growth of the cells thus opposing the action of AII. Agonists of AIV binding to the AT4 receptor will be effective inhibitors of vascular smooth muscle growth and will be therapeutically useful in reducing neointimal growth which often occurs following angioplasty.

As disclosed herein, high levels of AT4 receptors are present in cardiac and vascular tissue, including cultured bovine endothelial cells. The disclosure, herein, that AIV ligands and the AT4 receptors may function as growth factors of the tyrosine kinase class indicates that certain inhibitors of tyrosine kinase growth factors may also serve as inhibitors of certain angiotensin AIV ligand-receptor system-mediated cellular hypertrophic processes (e.g., ventricular hypertrophy), and that nucleotide probes constructed for complementarity to portions of RNA encoding the AIV ligand and receptor sequence may be useful in identifying other members of the AIV family of growth factors.

The invention also provides diagnostic applications for the AIV peptide ligands and antibodies. The role of the AT4 receptor-ligand system in cardiovascular regulation suggests a possible value to diagnostic tests for monitoring the levels of AIV ligand and AT4 receptor in biological fluids and tissues (i.e., rather than AII or AIII). Individuals with high renin-sodium profiles are reportedly at five times greater risk of myocardial infarction than individuals with low renin-sodium profiles despite adequate control of systemic blood pressure (28).

The AIV peptides, ligands, receptor fragments, and the like disclosed herein are useful in diagnostic assays, e.g., immunoassays, for the detection of the presence or amounts of AIV ligands or receptors in tissues, cells, and biological fluids of patients. The AIV peptides, ligands, analogs, derivatives, or covalently modified AIV peptides of the invention may be formulated in buffers with stabilizers, e.g., for use as positive or negative controls in diagnostic assay, or in reagent test kits for receptor-binding assays.

Those skilled in the art will recognize that the AIV ligands of the invention may be readily employed using conventional techniques to produce polyclonal or monoclonal AIV ligand specific antibodies, and that the isolation and purification of the AT4 receptor provides materials useful for preparation of polypeptide fragments (e.g., using CNBr and proteolytic enzymes) that can be subjected to automated amino acid sequencing. The amino acid sequence of the AT4 receptor, in turn, provides the sequence data necessary for construction of conserved and degenerate nucleotide probes for cDNA or genomic molecular cloning of nucleic acids expressing the AT4 receptor, mutant AT4 receptor, or fragments of the AT4 receptor. A convenient method for molecular cloning of the receptor is provided in Example 7.

EXAMPLE 1

Physical Characterization of the AIV Receptor
Kinetic Binding Studies: Bovine Adrenal Cortical Membranes In kinetic binding studies, conducted as set forth in Example 1 Materials and Methods described below, both $^{125}$I Sar$_1$,Ile$_8$-AII and $^{125}$I-AIV binding were characterized by slow association rates ($k_1$=1.01±12×10$^{-2}$ and 5.58±0.64× 10$^{-2}$ nM$^{-1}$ min$^{-1}$, respectively), very slow dissociation rates ($k_{-1}$=2.36±0.49×10$^{-2}$ and 2.57±0.05×10$^{-2}$ nM$^{-1}$ min$^{-1}$, respectively), and high affinity binding (calculated $K_d$=2.25±0.26×10$^{-10}$ M and 4.42±0.46×10$^{-10}$ M, respectively; number of experiments (n)=4) (Table 2).

TABLE 2

Kinetic constants for $^{125}$I Sar$_1$,Ile$_8$-AngII and $^{125}$I-AIV binding to bovine adrenal cortical membranes.*

| Ligands | $k_1$ (nM$^{-1}$ min$^{-1}$) | $k_{-1}$ (min$^{-1}$). | $K_d$ (M) |
|---|---|---|---|
| $^{125}$I Sar$_1$, Ile$_8$-Ang II | 1.01 ± 12 × 10$^{-2}$ | 2.36 ± .49 × 10$^{-2}$ | 2.25 ± .26 × 10$^{-10}$ |
| $^{125}$I-AIV | 5.58 ± .64 × 10$^{-2}$ | 2.57 ± .05 × 10$^{-2}$ | 4.42 ± .46 × 10$^{-10}$ |

*n = 3, mean ± SD

Equilibrium Binding Studies: Bovine Adrenal Cortical Membranes

Equilibrium binding studies were conducted to evaluate the binding of $^{125}$I-AIV to receptors in bovine cortical membrane preparations. Comparisons were made of the binding of both AIV and of AII, i.e., to the classical AT1 receptor sites defined by binding of $^{125}$I-Sar$_1$,Ile$_8$-AII. Binding studies were carried out in buffer containing 5 mM EDTA, 10 μM Bestatin, 50 μM Plummer's inhibitor, and 100 μM PMSF, developed specifically to inhibit metabolism of angiotensin fragments and receptors during the assay.

Saturation isotherms for $^{125}$I-AII and $^{125}$I-AIV indicated the presence of two distinct separable high-affinity binding sites in bovine adrenal cortical membrane preparations, i.e., one for AII ligand and a second for AIV ligand. The equilibrium constants calculated from this data were as follows: a) for AII receptor-ligand binding (i.e., $^{125}$I-Sar$_1$Ile$_8$-AII) the $K_d$=0.54±0.14 nM, $B_{max}$=1.03±0.26 pmol/mg membrane protein (n=4); and b) for the AT4 receptor ligand binding (i.e., $^{125}$I-AIV) the $K_d$=0.74±0.14 nM, $B_{max}$=3.82±1.12 pmol/mg membrane protein (n=4). The results of the equilibrium binding studies with membrane-bound AT4 receptor are summarized in Table 3.

TABLE 3

Equilibrium Binding Constants for $^{125}$I Sar$_1$, Ile$_8$-Ang and $^{125}$I-AIV Binding to Bovine Adrenal Cortical Membranes.

| Ligand | $K_d$ (nM) | $B_{max}$ (pmol/mg prot.) | Hill Coeff. | r (Scatchard) |
|---|---|---|---|---|
| $^{125}$I Sar$_1$, Ile$_8$-Ang II | 0.54 ± .14 | 1.03 ± .26 | 1.00 ± .03 | 0.91 ± .08 |
| $^{125}$I-AIV | 0.74 ± .14 | 3.82 ± 1.12 | 1.00 ± .02 | 0.93 ± .05 | n = 4, mean ± SD

The results of these kinetic and equilibrium binding studies show: (a) two separable high affinity binding sites, one for AII and a second for AIV; (b) large differences in the maximal binding ($B_{max}$) per mg membrane protein, i.e., with more than three-fold more AT4 receptor in this preparation than AII receptor; and, (c) no cross-displacement of AII binding by AIV or vice versa. The results provide convincing evidence for the existence of two separable receptors; one for AII and a second for AIV. However, the theoretical possibility existed that a single receptor might have differing affinities for AII and AIV. Since it was known that AT1 and AT2 are commonly destroyed during extraction from membranes, and are also heat labile (i.e., at 60° C.) a scheme was devised to rule out the later possibility by testing for AT4 receptors in solubilized and heat-treated membrane preparations. The results of these studies are presented below.

Equilibrium Binding Studies: Solubilized Bovine Adrenal Cortical AT4 Receptor

Initial studies, conducted as described in Example 1 Materials and Methods, confirmed that $^{125}$I-AIV bound to solubilized receptors in membrane preparations which would not be expected to contain AT1 or AT2 receptors. The kinetics of binding of $^{125}$I-AIV to the solubilized bovine adrenocortical receptor, at an AIV ligand concentration equal to 25% of the apparent $K_d$ (with 25 μg of membrane protein), indicated that equilibrium was reached in approximately 100 min. at 37° C.) The plateau region of binding to the solubilized receptor for $^{125}$I-AII or $^{125}$I-AIV, (after reaching equilibrium), was stable for at least one additional hour. The off-rate of the AT4 receptor, as determined following the addition of 1000-fold excess of unlabeled AIV, was exceedingly slow, with an average $t_{1/2}$=292.4 min (n=5).

Figure 2A:
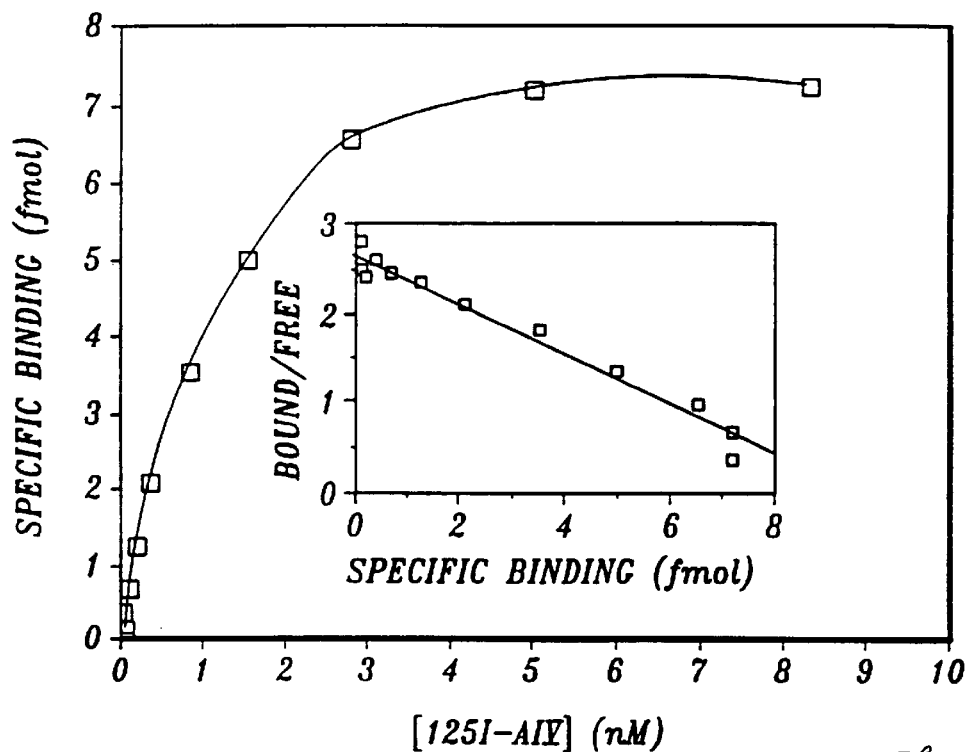
FIG. 2A is a graphical representation of the results of equilibrium binding studies of $^{125}$I-radiolabeled AIV to AT4 receptors isolated from bovine adrenal cortical membranes; and described in Example 1.

Equilibrium binding studies were next conducted at 37° C. with a 120-minute incubation (as in the Materials and Methods) with the solubilized membrane receptor preparations. Saturation isotherms for $^{125}$I-AIV (FIG. 2A) and $^{125}$I-AII (not shown) were developed to compare the equilibrium binding constants of the solubilized AT4 receptor. A concentration range of about 5×10$^{-6}$ M to about 5×10$^{-12}$ M AIV was employed in a typical experiment using 25 μg of total protein. The best fit for the transformed data using the LIGAND program revealed a single AIV binding site with no apparent cooperactivity. A summary of the binding data for AIV ligand to solubilized receptor is found in Table 4.

TABLE 4

Equilibrium Binding Data for $^{125}$I-AIV to Bovine Adrenal Cortical Solubilized Receptor.

| *$K_d$ (M) | $B_{max}$ (fmol/mg protein) | r (Scatchard Plot) | Hill Coefficient |
|---|---|---|---|
| 5.06 ± .57 × 10$^{-10}$ | 87.9 ± 9.7 | 0.991 ± .009 | 0.995 ± .039 |

*N = 4, mean ± SD

The data presented in Table 4 shows that the solubilized receptor, like the membrane receptor (Table 3), has an extraordinarily high binding affinity for AIV.

Competition Binding Studies: Bovine Adrenal Cortical Membranes

To establish the specificity of the AT4 receptor, competition curves were developed with several different angiotensin analogs using a concentration range of 10$^{-6}$ M to 10$^{-11}$ M. Comparisons were also made of the binding specificity of classical AT1 receptor binding sites (i.e., $^{125}$I-Sar$_1$,Ile$_8$-AII binding sites). Competition analysis (the summarized results of which are presented below in Table 5) also clearly distinguished the existence of two distinct receptors based on their specificity for different ligand structures in the angiotensin analogs. (The r values for log-logits transformations of the competition data were typically >0.98.) Binding of $^{125}$I-AII ligand to the AII receptor (as characterized by binding of $^{125}$I-Sar$_1$,Ile$_8$-AII) was effectively competitively inhibited by Sar$_1$,Ile$_8$-AII, AIII, and DuP 743. In contrast, AIV ligand, $AII_{(4-8)}$, and CGP42112A demonstrated very little affinity for the AII binding site (Table 5.) The pattern of binding at the AII site is consistent with a Type I classic AII binding site (20,25). (Binding $Sar_1$, $Ile_8$-Ang II, $Sar_1$, $Ile_8$-Ang II, AII, AIII, and DuP 753 with high affinity is a pattern of binding specificity consistent with an AT1 site.) In contrast to the AII receptor, the binding site for $^{125}$I-AIV ligand was effectively competitively inhibited only by AIV ligand and to a lesser extent by the peptides in the AIII preparation (Table 5).

TABLE 5

Competition of $^{125}$I-$Sar_1$, $Ile_8$-AII and $^{125}$I-AIV Binding to Bovine Adrenal Cortical Membranes.

| Competitor | $^{125}$I-$Sar_1$, $Ile_8$-AII Binding ($K_i$, M) | $^{125}$I-AIV Binding ($K_i$, M) |
|---|---|---|
| $Sar_1$,$Ile_8$-AII | $0.22 \pm 0.10 \times .10^{-9}$ | $>10^{-6}$ |
| AII | $2.01 \pm 0.67 \times .10^{-9}$ | $>10^{-6}$ |
| AIII | $1.15 \pm 0.34 \times .10^{-9}$ | $>14.50 \pm 2.3 \times 10^{-9}$ |
| AIV | $>10^{-6}$ | $0.58 \pm 0.15 \times 10^{-9}$ |
| AII(4–8) | $>10^{-6}$ | $>10^{-6}$ |
| DuP743 | $3.10 \pm 0.67 \times 10^{-8}$ | $>10^{-4}$ |
| CGP 42112A | $>10^{-4}$ | $>10^{-4}$ |

Binding Studies: Two Receptor Binding States in Rabbit Heart Membranes

Studies were next conducted to examine the kinetic parameters of $^{125}$I-angiotensin IV binding to receptors in P2 membrane preparations from rabbit heart. Comparisons were made of the binding of both AIV and of AII, i.e., to the classical AT1 receptor sites defined by binding of $^{125}$I-$Sar_1$, $Ile_8$-AII. Binding studies were carried out in a buffer (below) containing an extensive cocktail of inhibitors that was designed to minimize metabolism of both the receptor and the test ligand, i.e., the buffer contained 5 mM EDTA, 0.2% BSA, 10 μM Bestatin, 50 μM Plummer's inhibitor, and 100 μM PMSF.

Angiotensin peptides (i.e., AI, AII, AIII, or AIV) were stable in this buffer for 4 h at 37° C. with less than 10% hydrolysis measured by reverse phase HPLC.

The studies were conducted as described in the Materials and Methods, below. The association rate constant ($k_1$) for $^{125}$I-AIV was determined to be $3.05 \times 10^8$ M$^{-1}$ min$^{-1}$ and the dissociation rate constant ($k_{-1}$) was $0.028+/0.017$ min$^{-1}$ The overall dissociation constant ($K_d$) measured under equilibrium binding conditions as determined to be $9.15 \times 10^{-11}$ M. (The results represent the mean values from the results of 4 experiments conducted using duplicate samples.) Saturation isotherms and Scatchard analysis produced data best resolved in a two-site model using non-linear curve fitting methods (LIGAND program curve fitting options). The $K_d$ for site #1 was determined to be $10.3 \pm 3$ mM with $B_{max}$= $1747 \pm 393$ fmol/mg; the $K_d$ for site #2 was $10.1 \pm 5$ pM with $B_{max}$=$15 \pm 4$ fmol/mg. Binding to the rabbit heart membranes was competitively inhibited in a specific manner by AIV but not AII, AIII, $^{125}$I $Sar_1$,$Ile_8$-AII, DuP753, CGP, $AII_{(4-8)}$, or DAAI (see Table 6).

TABLE 6

Competition of Binding of $^{125}$I-AIV to Rabbit Heart Membrane Receptors

| Competitor | $K_i$ (M) |
|---|---|
| AIV | $1.4 \times 10^{-9}$ |
| AII | $>10^{-6}$ |
| AIII | $2-3 \times 10^{-7}$ |

TABLE 6-continued

Competition of Binding of $^{125}$I-AIV to Rabbit Heart Membrane Receptors

| Competitor | $K_i$ (M) |
|---|---|
| $Sar_1$, $Ile_8$-AII | $>10^{-6}$ |
| DUP753 | $>10^{-6}$ |
| CGP | $>10^{-6}$ |
| $AII_{(4-8)}$ | $>10^{-6}$ |
| DAAI | $90.5 \times 10^{-9}$ |

The data in Table 6 was calculated from competition displacement curves for binding of 0.5 nM $^{125}$I-AIV to membrane fractions; membranes were incubated for 120 min. at 37° C. in the presence of 10 pM to 1 mM competitor; possible conversion of AIV to other (smaller) fragments was evaluated after 120 min at 37° C. by adding 20% TCA to stop the incubation, and then evaluating the percentage of AIV by reverse-phase HPLC on a C18 column with a 20% ACN/TEAP3 mobile phase; greater than 92% of the $^{125}$I label present at the conclusion of the incubation was present as AIV.

Structural Requirements for Ligand Binding to Bovine Adrenal AT4 Receptors

Figure 2B:
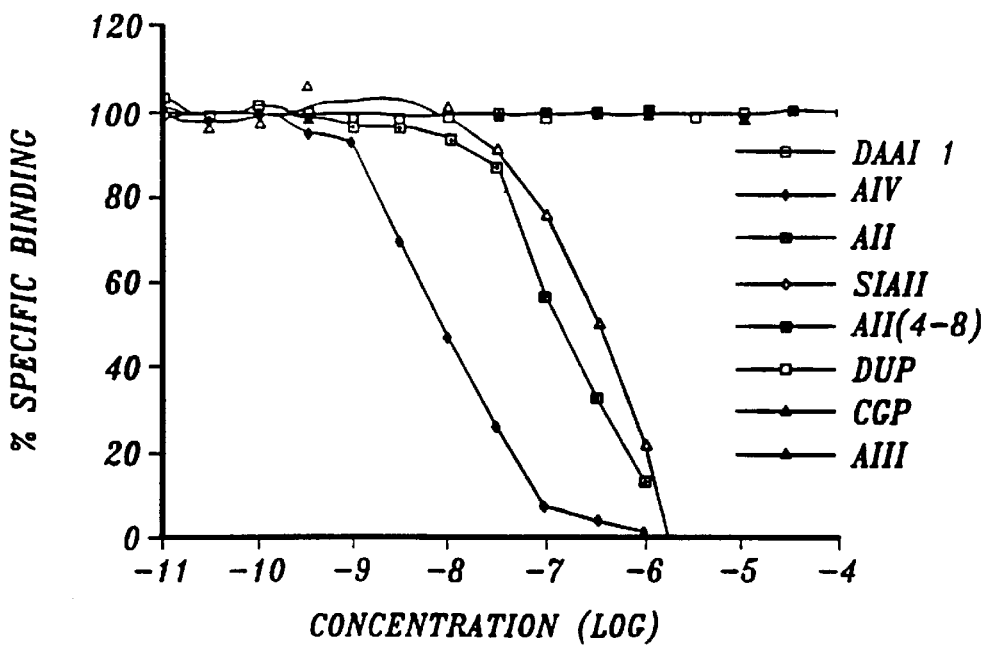
FIG. 2B depicts graphically the structural requirements and specificity for binding of AIV ligand to the AT4 receptor from rabbit cardiac myocyte membranes; as described in Example 1.
Figure 3A:
FIGS. 3A–3I compares AT2 and AT4 receptor localization in the Habenula region of the brain using receptor autoradiography with $^{125}$I-Sar$_1$,Ile$_3$-AII to localize AT2 receptors, and $^{125}$I-AIV to localize AT4 receptors, as described in Example 2. Panel A shows binding of $^{125}$I-AIV to cells in the habenula, thalamus, cerebral cortex and hippocampus of guinea pig brain. Panel B shows that the binding of $^{125}$I-AIV is specifically competitively inhibited by 100 nM non-labeled AIV competitor. Panel C shows that binding of $^{125}$I-AIV is not competitively inhibited by 100 nM Sar$_1$,Ile$_8$-AII. Panel D shows a pattern of binding of $^{125}$I-Sar$_1$,Ile$_8$-AII to AT2 receptors that is different from the pattern observed with $^{125}$I-AIV in Panel A. Panel E shows that binding of $^{125}$I-Sar$_1$,Ile$_8$-AII is specifically inhibited by 100 nM of non-labeled AII competitor. Panel F shows that binding of $^{125}$I-Sar$_1$,Ile$_8$-AII is not inhibited by 100 nM non-labeled AIV competitor. Panel G shows a "pseudo-color" photograph of $^{125}$I-AIV binding. Panel H shows a "pseudo-color photograph of $^{125}$I-Sar$_1$,Ile$_8$-AII binding. Panel I shows a photomicrograph of a histology slide of a serial section of the same tissue as in Panels A–I.
Figure 3B:
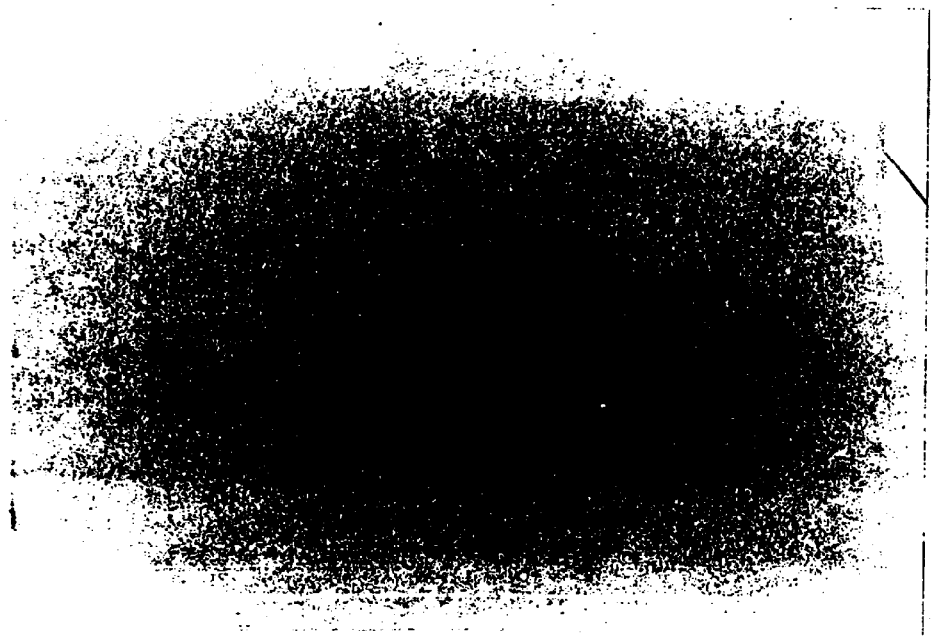
Figure 3C:
Figure 3D:
Figure 3E:
Figure 3F:
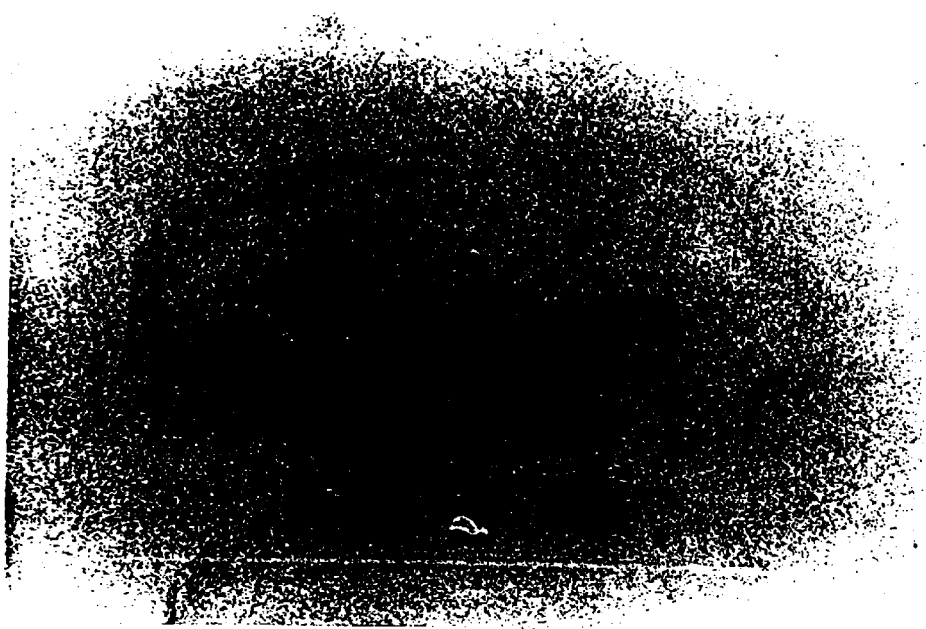
Figure 3G:
Figure 3H:
Figure 3L:

The results in Table 7, also include a summary of studies designed to analyze the structural features of the N-terminus of an AIV ligand that are required for binding to an AT4 receptor. The results of these structural studies are also presented in FIG. 2B. The results show that modification of the N-terminal valine residue (i.e., by N-terminal shortening of AIV to $AII_{(4-8)}$), or extending the N-terminus with a hydrophobic residue such as Sar or GABA, or changing the stereoisomer of the L-Val to D-Val, all drastically decrease binding of an AIV ligand to the AT4 receptor (Table 7). The AT4 receptor also failed to bind DuP 743 (DuP, FIG. 2B) or CGP 42112A (CGP, FIG. 2B) and thus did not exhibit the pharmacological properties of a classic AII binding site (26). As shown in FIG. 2B, the ability of the various compounds to inhibit AIV binding to the solubilized AT4 receptor was tested. The following compounds are shown in FIG. 2B as follows: DAAI1, desAsp angiotensin I (i.e., identical at the N-terminus to AIII; see open squares with a dot, FIG. 2B); AIV, angiotensin IV (closed diamonds, FIG. 2B); AII (open squares, FIG. 2B); SIAII (AII lacking the Ile residue at position 5, FIG. 1; open diamonds, FIG. 2B); DuP (Dup 743, an AII analog; open squares, FIG. 2B); CGP (CGP 42112A, another AII analog; closed triangles, FIG. 2B); and, AIII (open triangles, FIG. 2B. The results presented in FIG. 2B and the $K_i$ values summarized below in Table 7 show that: (a) only AIV, and peptides in the DAAI1 (i.e., AIII N-terminal sequence), and AIII preparations effectively competitively inhibit binding of the $^{125}$I-AIV ligand to the AT4 receptor; and (b) the peptides in the AIII, $Sar^1$-AIII, and DAAI1 preparations are approximately 100 times less effective than AIV in competing binding to the AT4 receptor.

TABLE 7

Competition of $^{125}$I-AIV Binding to Solubilized Bovine Adrenal Cortical Receptor.

| Analog/Competitor | $K_i$ (M) |
|---|---|
| AIV | $5.67 \pm 1.71 \times 10^{-10}$ |
| AIII | $2.28 \pm 0.17 \times 10^{-8}$ |
| AII | $>10^{-6}$ |
| $AII_{(4-8)}$ | $>10^{-6}$ |

TABLE 7-continued

Competition of $^{125}$I-AIV Binding to Solubilized Bovine Adrenal Cort gradient were 65% H₂O, 35% acetonitrile and 1% TFA. Purified peptides were amino acid analyzed to determine both peptide and total purity. Typically the peptides produced were greater than 99% pure and contain 20–25% acetate.

Tissue Preparation: bovine adrenal cortical tissues

Adrenal cortex was removed from bovine adrenals obtained from a local slaughterhouse. The minced cortex was then homogenized in a Polytron as a 40:1 suspension in assay buffer at 10 sec/ml. The homogenate was then centrifuged at 500 g for 10 min. to remove whole cells and nuclei. After a rehomogenization and recentrifugation the combined supernatants were spun at 40,000×g for 20 min. The pellet was rehomogenized and respun at 40,000 rpm for 30 min. This final pellet was resuspended in assay buffer and layered on a discontinuous sucrose gradient (0.8M/1.2M). After a 100,000×g spin for 90 min. the purified membranes were located at the density interface and were removed. The sucrose containing membrane suspension was diluted 1:10 in assay buffer and spun a last time at 40,000×g for 30 min. The pellet was resuspended in assay buffer at a concentration of 10 mg protein/ml and heat treated at 60° C. for 30 min. in the presence of 20 mM MgCl₂. The membranes, now devoid of almost all peptidase activity, were ready for use in the binding assay.

Binding studies: bovine adrenal cortical membranes

To test the ability of the synthesized analogs to competitively inhibit for $^{125}$I-AIV binding a displacement curve was established using purified bovine adrenal cortical membranes. Binding was carried out in 10–75mm siliconized glass culture tubes containing 0.2 nM $^{125}$I-AIV, 25 mg of membrane protein, and the desired analog over a concentration range of $10^{-12}$M to $10^{-4}$M using half-log dilutions. All binding incubations were carried out in duplicate at 37° C. for 2 h in a buffer containing: 50 mM Tris, 150 mM NaCl, 5 mM EDTA, 10 μM bestatin, 50 μM Plummer's Reagent, 100 μM PMSF and 0.2% BSA (assay buffer) in a total volume of 0.25 ml. After incubation, the incubates were filtered through GF-B filters soaked in 0.3% polyethyleneimine and washed with four-4 ml washes of PBS. The filters were then counted in a Beckman 5500 gamma counter. A typical experiment examines 5 analogs simultaneously and includes a positive control curve in which AIV was used as the displacer. All curves were run in quadruplicate, each with a different tissue preparation. Nonspecific binding was defined as total binding minus binding observed in the presence of 100 mM Sar₁,Ile₈-AII or 100 mM AIV. No cross displacement (i.e., of AII binding by AIV or AIV by AII) was observed. HPLC analysis of both the bound and free $^{125}$I-AII or 125I-AIV ligand indicated that 100% of the "specifically bound" label was either 125I-AII or 125I-AIV, respectively, and the overall hydrolysis of $^{125}$I-AII under conditions of the assay was less than 2%.

Data were analyzed by the LIGAND program (29) from which $K_i$ values can be obtained.

Binding studies: solubilized bovine adrenal cortical receptor

Solubilization and characterization of the receptor from bovine adrenal membranes was accomplished by homogenizing the membranes (above) in hypertonic buffer followed by fractionation of the membranes by sucrose density gradient centrifugation. The membrane preparation was then heat treated at 60° C. in the presence of MgCl₂ (to inactivate AT1 receptors). The heat treatment also reduced endogenous peptidase activity in the preparations by 90–95%. The AT4 receptor in the preparations was then solubilized using 1% zwitterionic detergent 3-[(3-cholamidopropyl) dimethyl ammonio]-1-propanesulfonic acid (CHAPS).

Binding studies: rabbit heart

P2 membranes from rabbit heart were prepared by homogenization and differential centrifugation at 4° C. Binding was carried out in the presence of 5 mM (EDTA), 0.2% heat-treated bovine serum albumin (HTBSA), 10 μM Bestatin, 50 μM Plummer's inhibitor, 100 μM phenylmethylsulfonylfluoride (PMSF), and 50 mM Tris, pH7.4, at 22° C. Binding was initiated by the addition of 100 mg protein and appropriate amounts of labeled ligand. (For kinetic binding studies the samples were incubated for 10, 20, 30, 40, 50, 60, 90, 120, 150, 180, and 220 minutes at 37° C. For equilibrium binding studies the same conditions were used and samples were incubated for 120 min at 37° C.) All incubations were conducted at a final volume of 250 ml in 12×75 mm siliconized (SigmaCote) borosilicate tubes, and they were terminated by rapid vacuum filtration in a Brandel cell harvester through glass fiber filters (Schleicher and Schuell #32) soaked in 0.3% polyethyleneimine. Filters were immediately rinsed with 4×4 ml 150 mM NaCl, 50 mM Na₂HPO₄, pH7.2 at room temperature. Filters were allowed to air dry, placed in fresh tubes and counted in a gamma counter. Specific binding was defined as the difference between the absence and presence of 1.0 mM displacing ligand.

Dissociation (i.e., of ligand from receptors) experiments were conducted by adding 1 mM unlabeled AIV ligand competitor to the assay at 120 minutes after initiating binding (at 37° C.) with 0.5 nM $^{125}$I-AIV.

Saturation isotherms for binding were conducted with approximately 25 μg of tissue protein incubated with various concentrations of $^{125}$I-AIV for 120 min. at 37° C.; nonspecific binding was defined in the presence of 1 mM AIV. Three experiments were conducted resulting in 36 data points for Scatchard analysis.

EXAMPLE 2

Tissue and Species Distribution of the AIV Receptor

Species Distribution:

A second major approach to defining separate and distinct binding sites was to examine their relative tissue and species distribution (Table 8). The results presented in Table°8 show the fentamoles of AII or AIV bound per milligram of membrane protein in extracts prepared under identical conditions from the tissues and species indicated.

TABLE 8

*Distribution of $^{125}$I-SI-AII and $^{125}$I-AIV Binding in Mammalian Tissues.**

| Species | Tissue | $^{125}$I-SI-AII (fmol/mg prot.) | $^{125}$I-AIV (fmol/mg/prot.) |
|---|---|---|---|
| cow | adrenal medulla | 218.8 ± 56.2 | 397.3 ± 53.6 |
| pig | whole adrenal | ND | 70.8 ± 6.7 |
| horse | whole adrenal | 1.8 ± 1.0 | 72.7 ± 13.5 |
| dog | whole adrenal | 4.6 ± .7 | 36.5 ± 5.4 |
| cat | whole adrenal | 3.3 ± 2.3 | 199.6 ± 19.7 |
| rabbit | whole adrenal | 79.6 ± 21.6 | 105.3 ± 15.6 |
| rat | whole adrenal | 158.2 ± 21.6 | N.Det. |
| guinea pig | whole adrenal | 45.6 ± 9.2 | 101.2 ± 26.3 |
| cow | coronary venule endothelial cells | 2.9 ± 0.3 | 85.1 ± 3.3 |
| rabbit | heart | 10.6 ± 3.6 | 249.9 ± 36.3 |

*25 $\mu$g of membrane protein was incubated with 500,000 cpm of label. Specific binding was defined as total binding-nonspecific binding at 100 nM unlabeled peptide.

TABLE 8-continued

*Distribution of $^{125}$I-SI-AII and
$^{125}$I-AIV Binding in Mammalian Tissues.**

| Species | Tissue | $^{125}$I-SI-AII (fmol/mg prot.) | $^{125}$I-AIV (fmol/mg/prot.) |
|---|---|---|---|

**n = 2–6; mean ± SE; $^{125}$I-SI-AII = 125I-Sar$_1$, Ile$_8$-AII; fmol/mg protein = femtomoles (i.e. $10^{-15}$M) of AII ligand bound per mg of total protein in the preparation.
N.Det. = not detectable, i.e., less than 1.8 fmol/mg protein.

The results show that: a) the human AIV ligand binds AT4 receptors in a wide variety of mammalian species; and b) most mammalian adrenal tissue express an AT4 receptor capable of binding the AIV hexapeptide VYIHPF (SEQ. ID. NO. 1).

Tissue Distribution:

In order to begin to assign physiological functions to the AIV ligand-AT4 receptor interaction, preliminary tissue distribution studies have been conducted in guinea pigs. Guinea pigs were chosen because their adrenal tissues demonstrated high levels of AIV binding (Table 8). The tissue distribution of AT4 receptors was measured by assaying radioligand binding to membrane preparations, i.e., as described in Example 1, above.

TABLE 9

Distribution of $^{125}$I Sar$_1$, Ile$_8$-AII and $^{125}$I-AIV Binding sites in the Membranes of Guinea Pig Tissues.*

| Tissue | $^{125}$I Sar$_1$, Ile$_8$AII Binding (fmol/mg prot) | $^{125}$I-AIV Binding (fmol/mg prot) |
|---|---|---|
| aorta | 3.17 ± 2.2 | 45.4 ± 11.0 |
| brain | 17.70 ± 9.5 | 60.8 ± 13.5 |
| heart | 5.70 ± 0.6 | 83.3 ± 20.8 |
| kidney | 8.10 ± 1.19 | 22.7 ± 12.1 |
| liver | 22.40 ± 5.3 | 28.9 ± 6.4 |
| lung | 12.20 ± 6.4 | 56.1 ± 10.1 |
| uterus | 4.00 ± 1.5 | 87.0 ± 6.3 |

*n = 4; Binding was carried out as described in Table 6, above.

The combined results presented in Table 9, above, show that the receptor was widely distributed in the tissues. The combined results suggest evolutionary conservation of both the AT4 receptor and the AIV ligand.

Additional studies were next conducted to physically compare the receptors in guinea pig brain, rabbit heart, and bovine coronary venule endothelial cells with respect to their binding affinities for AIV ligand. The results of these studies indicate that cells in these different tissues all have AT4 receptors with comparable binding affinity for AIV ligand; each cell type has an AT4 receptor with a $K_d$ for $^{125}$I-AIV of about 0.1 nM to about 0.5 nM. Next, competition studies similar to those presented above in Example 1 were conducted to evaluate the structural requirements for building AIV in different tissues. The results indicate that each AT4 receptor exhibits the same N-terminal specificity recorded, above, i.e., for V, I, or K. The results of these combined studies support the notion that a remarkable degree of evolutionary conservation has been maintained for AIV ligand-AT4 receptor system, and this level of conservation is commonly predictive of important, and probably critical, physiological functions.

Surprisingly, it has not been possible to demonstrate binding of $^{125}$I-AIV in rat tissues including brain, heart, kidney, aorta, lung, liver, or cultured smooth muscle cells (n=5) (Table 8). At this time, the significance of this finding is uncertain. It is possible that the in vitro assay conditions may not be optimal for this species and that the AT4 receptor or AIV ligand may be rapidly inactivated, e.g., by high levels of peptidases known to be present in rat tissues.

In addition, on a technical note, binding of the AIV ligand to the AT4 receptor was inhibited in the presence of Bacitracin (i.e., 10 mg/ml; at a final calculated concentration in the assay of 0.07M). Bacitracin is a polypeptide antibiotic with the sequence ICLEIKOIFHDD (SEQ. ID. NO. 32) (i.e., O is ornithine), and it is often included in angiotensin binding assays to inhibit the action of nonspecific proteases (i.e., as an alternative substrate for the proteases). The observation of bacitracin interference is of potential significance for at least two reasons: 1) previous investigators who have included bacitracin in their assay buffers may have inhibited AIV ligand binding to the AT4 receptor; and, 2) inhibition of AIV binding by this polypeptide (notably at a very high molar concentration) may provide an indication of amino acid sequences that may contribute to electrostatic interactions in the AT4 receptor binding site (e.g., $R_1IR_2HR_2$, where $R_1$ is an amino acid with an aromatic side chain such as OH, SH, or NH, and $R_2$ is a polar amino acid).

The results of the tissue distribution studies, above, indicate that the receptor is present in the adrenal tissues in most mammalian species, and can be isolated in P2 membrane preparations from most mammalian species.

Receptor Autobiography in Tissues:

Receptor autoradiography is a useful extension of radioligand binding studies since it provides detailed anatomical information about the location of receptors in tissues and groups of cells in tissues, and thus it facilitates understanding the function of the AIV ligands and AT4 receptors in those sites. Autoradiographic analyses of serial sections of guinea pig brain (20 mM thickness) were performed. The autoradiographs showed a pattern of distribution for AII receptors and AT4 receptors in the Habenula (FIG. 3), Hippocampus (data not shown) Cerebellum (data not shown), Prefrontal Cortex (data not shown), and Thalamus (data not shown). In each case the receptor distribution in the tissue was determined by binding of $^{125}$I-Sar$_1$,Ile$_8$-AII, or $^{125}$I-AIV, respectively. Specificity of ligand binding in these autoradiographic studies was demonstrated by competing the binding of the specific ligand (i.e., AII or AIV) with unlabeled 100 nM Sar$_1$,IIe$_8$-AII, or 100 nM AIV, respectively. The data demonstrate that while specific AII and AT4 receptors are located at similar sites in the Habenula, Hippocampus, and Cerebellum of guinea pig brain, the two receptors are distinct with regard to exact groups of cells that express the two different receptors. Major differences were observed in the Prefrontal Cortex and Thalamus where AT4 receptors were abundant but AII receptors appear to be relatively rare.

In the Hippocampus the AT4 receptor is present in the pyramidal cell layer CA1, CA2, and CA3 of the Hippocampus and dentate gyrus. Binding of AIV occurred at a single binding site with high affinity ($K_d$=1.29±0.18 nM, mean ±SD, Hill Coef.=0.993±0.015) and in a saturable manner ($B_{max}$=449±62 fmol/mg protein). The properties of the hippocampal AIV ligand-receptor system as described in greater detail below (see Example 7). The findings of AT4 receptors in the Hippocampus suggest that the AIV ligand-receptor interactions in the Hippocampus may mediate unique angiotensin-dependent functions including memory enhancement. The AIV ligand-receptor system may provide a link between the Hippocampus and memory.

The mutually exclusive cellular distribution of AIV and AII receptors is demonstrated in the autoradiograph shown in FIG. 3. Panel A reveals intense $^{125}$I-AIV binding in the habenula, while Panel D indicates that $^{125}$I-Sar$_1$,Ile$_8$-AII binding is localized primarily to fiber tracts including the visual segmental relay zone and the medial lemniscus. The specificity of ligand binding to receptors in these tissues was illustrated by competing $^{125}$-AIV binding with 100 nM non-labeled AIV (not AII) [(FIG. 3, Panels B and C)]; and, 100 nM non-labeled Sar$_1$,Ile$_8$-AII displaced only the $^{125I}$-Sar$_1$, Ile$_8$-AII binding [(FIG. 3, Panels E and F)]. Some tissues, however, may contain both AII and AT4 receptors.

Quantitative aspects of binding in brain is presented in Example 7, and other tissues data is presented in Example 1, above. The results show that all important cardiovascular tissues in guinea pigs contain the AT4 receptor. This result is not surprising in light of the observation (above) that vascular endothelial cells contain high concentrations of receptors, but this is not responsible for tissue binding of AIV ligand because every vascularized tissue will possess AT4 receptors, i.e., skin and skeletal muscle has low levels of receptor.

Materials and Methods:

Autoradiographic analysis of $^{125}$I-AIV and $^{125}$I-Sar$_1$,Ile$_8$-AII binding in guinea pig tissue was determined as follows. Heart, kidney, brain, and other tissues were cryostat-sectioned into 20 mm sections that were mounted on chrome-alum- gelatin-coated slides in multiple sets of seven. The slide-mounted tissue sections were thawed (35° C.) and preincubated in assay buffer (150 mM NaCl, 50 mM Tris, 5 mM EDTA, 0.1% BSA, 10 µM bestatin, 50 µM Plummer's inhibitor, 100 µM PMSF, at pH7.4) for 30 min. and then incubated for 1 h in the same buffer with the addition of 225–250 pM of $^{125}$I-Sar$_1$,Ile$_8$-AII (for visualizing AH1 receptors) or $^{125}$I-AIV (for visualizing AT4 receptors). To define the specificity of the ligand binding, tissue sections were incubated in the radioligand in the presence and absence of 100 nM unlabeled AII or AIV peptide. After appropriate washing, autoradiograms were prepared by apposing the slide-mounted tissue sections to X-ray film (Hyperfilm, Amersham) for an appropriate exposure time. The amount of radioligand binding in a tissue was quantified using densitometric techniques and $^{125}$I standards (Microscales, Amersham, Arlington Hts, Ill.).

EXAMPLE 3

Receptor Isolation, Purification and Properties and Production of Monoclonal Antibodies Receptor Isolation and Purification:

The AT4 receptor was solubilized in high yield from purified bovine adrenal membranes using the zwitterionic detergent CHAPS (1%) at 4° C. over 4 h under conditions where peptidase activity and differential solubilization of the AT4 receptor (but not the AII receptors) is permitted (see also Example 4, *Materials and Methods*, below). For example, membranes from a variety of different tissues and cells (e.g., 25 mg of P2 membranes, Example 1) were incubated for 4 h in Hepes buffer (20 mM, pH7.4) containing 1% CHAPS and a cocktail of protease inhibitors and alternative protease substrates, i.e., 10 µM bestatin; 50 µM Plummers' inhibitor; 0.2% BSA (bovine serum albumin); and 100 µM PMSF (phenylmethylsulfonyl fluoride).

A most useful component of any AII receptor purification scheme was including a step wherein the solubilized membrane proteins were subjected to a heat treatment at 60° C., e.g., for 20 minutes and in the presence of 20 mM Mg$^{++}$. This step was useful in destroying any residual AII receptor leaving the AT4 receptor intact.

The AT4 receptor was stable to chromatofocusing and SDS-PAGE, allowing isoelectric focusing, or one- or two-dimensional PAGE or SDS-PAGE to be used for purification. Due to the slow-off rate of $^{125}$I-AIV binding, the receptor was radiolabeled with $^{125}$I-AIV ligand to allow ease of identification during purification. As an additional aid to purification, the receptor was successfully cross-linked to a $^{125}$I-radiolabeled AIV analog ligand having a C-terminal extension, i.e., from residue 8, with lysine residues (i.e., $^{125}$I-Lys$_{11}$-AIV). The Lys$_{11}$-AIV analog binds to the AT4 receptor with a K$_d$ that is similar to AIV ligand. Using Bis (sulfosuccinimidly) suberimidate (BS3) as the cross-linking agent, the $^{125}$I-Lys$_{11}$-AIV analog of AIV was bound to the AT4 receptor and then cross-linked to the AT4 receptor through the e-amino group of Lys. Purification of the AT4 receptor may also be achieved, for example, by ion exchange, lectin chromatography, hydrophobic chromatography with conventional techniques, HPLC, or FPLC.

SDS-PAGE analysis of isolated and purified receptor indicated a molecular weight between 130 KDa and 150 KDa, at about 146 KDa for the BS3-cross-linked AT4 receptor from bovine adrenal tissue. The purified, uncrosslinked receptor appears to have a significantly smaller molecular weight, on the order of 60 KDa.

Receptor Properties:

Identification of the family to which a receptor belongs commonly permits predictions to be made about possible improvements in purification, useful methods for stabilizing the receptor during purification, cellular sources and assays useful for molecular cloning of the receptor, and identification of novel physiological roles for a receptor. For instance, neurotransmitters and hormones are known to interact with four types of plasma membrane receptors: 1) multisubunit receptors that regulate an intrinsic ion channel; 2) G-protein linked receptors that, via the G-protein, can activate membrane channels and enzymes; 3) guanylate cyclase receptors that possess intrinsic guanylate cyclase activity in a single membrane spanning polypeptide chain; and, 4) protein tyrosine kinase receptors that have intrinsic tyrosine kinase activity capable of phosphorylating multiple protein substrates.

Many common neurotransmitters like acetylcholine, glycine, glutamate, and GABA activate receptor-ion channels. The interaction of the neurotransmitter and receptor results in the opening of an intrinsic ion channel. In all cases these receptors are constructed as heteromultimers and are most likely evolutionarily related. Despite the importance of this receptor class, to our knowledge no known peptide transmitter or hormone acts by such a mechanism. Thus, it is reasoned unlikely that the AT4 receptor is a member of this family of receptors.

Studies have been conducted to determine the receptor family to which the AT4 receptor belongs (see Examples 5 and 7). It has been reported previously that the AII receptor may be a member of the G-protein-linked family of cellular receptors. The majority of known peptide receptors belonging to this family are characterized by seven membrane-spanning alpha-helical regions and when stimulated are capable of activating membrane-bound enzymes like adenylate cyclase, phosphodiesterase, and phospholipase C. (30). Additionally, membrane channel or ion transporter properties can be indirectly modified by the intervening G-protein(31). Although many strategies have been devised to test a particular receptor's linkage with a G-protein, three strategies seem to predominate. In one form or another these include the following approaches: 1) GTP and its analogs are known to alter the binding affinity of agonists to their receptors. Therefore, the ability of GTP or analogs to change agonist-binding affinity is diagnostic of a G-protein-linked receptor. In the presence of GTP, dissociation of the G-protein subunits from the receptor results in a lowered affinity for agonists. This was examined (see Example 5) by the direct assessment of GTP (of GTPγS) effects on agonist binding via changes in dissociation rates or total binding over a range of GTP concentrations, or indirectly by monitoring shifts in $IC_{50}$ values for agonists during competition for antagonist binding. 2) Another indication of G-protein linkage is the ability of agonists to stimulate the intrinsic GTPase activity of the alpha subunit of G-proteins. This GTPase activity is triggered following receptor occupation and subsequent dissociation of alpha and beta-gamma subunits. 3) A final approach is to determine whether an agonist can facilitate nucleotide cycling. A crucial step in G-protein signal transduction is the agonist-stimulated dissociation of GDP from the alpha-subunit and its replacement with GTP. Changes in cycling are often assessed by comparing the binding of radiolabeled irreversibly bound GTP analogs before and after agonist stimulation.

Studies to date include studies to determine the cellular signal transduction mechanisms activated following binding of AIV ligand to the receptor. The data obtained with isolated AT4 receptor now strongly suggest Materials and Methods:
Cross-linking to the AT4 receptor Cross-linking $^{125}$I-AIV to the AT4 receptor can be accomplished with Bis (sulfosuccinimidyl) suberimidate (BS3) as discussed above. The cross-linked receptor (approx. mw of 146,000) can then be electroeluted from PAGE gel slices in a substantially pure form for use as an electrophoretic standard.

For cross-linking one milligram of total solubilized membrane protein containing AT4 receptor was incubated with 30×10−6 cpm of $^{125}$I-AIV in 50 mM Tris, pH7.4 and 150 mM NaCl containing a cocktail of protease/peptidase inhibitors for 2 hr at 37° C. (final volume 0.5 ml). Following incubation, the incubate was spun through two successive spin columns packed with 0.8 ml of Biogel P-6 extrafine (Biorad) that has been pre-equilibrated with 20 mM NaP buffer, pH7.4 containing 0.01% CHAPS.

The labeled receptor, now in phosphate buffer, was cross-linked with BS3 (final conc. 9 mM; added as 90 mM in DMSO). The mixture was incubated 30 min. at 0° C. Cross-linking was terminated by the addition of 100 ml of 1M Tris, pH9.0 with an additional 10 min. incubation at 0° C. The mixture was then spun through a final spin column to remove reactant and free ligand. The centrifugate was now ready for PAGE.

Production of Monoclonal Antibodies:

Monoclonal antibodies are useful for purification of receptor, and for identifying the receptor (and fragments thereof) in tissues, cells, and biological fluids. Purified or semi-purified AT4 receptor (preferably nondenatured) can be used as an in vivo or in vitro immunogen. (Those skilled artisans will recognize a variety of options available to them for evoking monoclonal and polyclonal antibodies, e.g., see Harlow, E. and D. Lane, Eds., "Antibodies: A Laboratory Manual" Cold Spring Harbor Laboratory, 1988). For in vitro immunization antigen can be incubated in picogram quantities with murine, rat, or human lymphocytes. Production of antibodies can be screened by testing for the ability of $^{125}$I-AIV-prelabeled receptor to bind to antibodies adsorbed on a polystyrene plastic surface, e.g., in 96 well plates; or, alternatively, by testing the ability of the antibody to inhibit binding of a purified labeled receptor to AIV ligand adsorbed to a solid phase. In either case, antibody producing cells are identified, cultured, and cloned. The monoclonal antibody product of the cloned cell lines can bind the AT4 receptor in ligand-binding and non-binding domains of the AT4 receptor. Non-binding domains can include structural regions of the molecule as well as enzyme active sites, phosphorylation sites, glycosylation sites, and the like. The presence of antibodies specific for the ligand-binding domain can be assessed directly via the ability of the mono to competitively inhibit in binding assays. As mentioned earlier antibodies are useful for receptor purification and immunohistochemical studies designed to elucidate the cellular location of receptors and also in structure/activity studies designed to map functional domains in the receptor.

EXAMPLE 4

AIV Receptor Antagonists and Agonists

To test the ability of synthesized AIV ligands to competitively inhibit for $^{125}$I-AIV ligand binding to the AT4 receptor, displacement curves were constructed using heat-treated (60° C. for 20 min. in 20 mM $MgCl_2$) purified bovine adrenal cortical membranes using Methods described in Example 1, above. Effects of AIV analogues on renal blood flow were determined as described in Example 6.

The design of AIV analogs followed a question based approach. The unifying question: What are the essential ligand domains for receptor binding and activation? Individual chemical modifications were made to ask specific questions about spacial orientation of molecular surfaces, charge, hydrophobicity and occupancy of space (volume occupied at a specific location). A standardized assay of analog competition was employed to study receptor-ligand binding affinity of the high affinity $^{125}$I-AIV-binding receptor in heat treated, sucrose density gradient purified bovine adrenal cortical membranes. Energy minimized, computer generated models ("Macromodel" program run on a Vax mainframe) provided the visual representations of the molecular conformation of highest probability.

Agonist versus antagonist activity was assessed using a laser doppler to monitor renal cortical blood flow following infusion of a test analog into the renal artery (see Example 6). Maximal response was compared to the response (increased in flow) to AIV. (Note that under these conditions AII produces a decrease in blood flow in this assay.) Interprestation of physiologic and binding data was based on the precept of a lock and key model of receptor binding and that dynamic change of the receptor upon interaction of the ligand was required for activation (full agonist activity; with second messenger activation).

The following main assumptions were used:

1.) Ligands with the highest affinity, when modeled in an energy minimized conformation offer a visual representation of the receptor binding site field surface (i.e., hydrophobic charge interactions) and charge locations in the "pre-binding state" and "non-activated state" (i.e., just as a clay imprint on a well fitting key represents the interaction surface of the lock).

2.) Specific ligand domains induce changes in the receptor upon binding that produce cellular responses. Ligands that fit the "pre-binding" receptor with high affinity may not activate the receptor, i.e., they may act as antagonists, while structures that induce changes in the conformation of the receptor may be compatible with, and part of, the changes that produce high affinity binding, i.e., they may act as agonists.

The following is a summary of the questions asked and the compounds synthesized to identify antagonists and agonists of the AT4 receptor that interfer with binding of physiological AIV fragments. The inventors believe that mapping the receptor binding site (herein) and understanding of the structure of the receptor and its signal transduction mechanism form the requisite basis for rational design of pharmacologic therapeutic agents that interact with this receptor system in vivo in mammals.

Question #1. What are the absolute AIV ligand amino acid requirements for binding to the AT4 receptor?

The approach used to answer this question involved deletion of residues from either the N- or C-terminus of AIV (i.e., VYIHPF; SEQ. ID. NO. 1), or from the larger AI sequence of which AIV is a part (i.e., FIG. 1). For the most part these studies employed the bovine adrenal cortical AT4 receptor present in membrane preparations prepared as described above in Example 1. The binding assays were also conducted as described in Examples 1 and 2, above, and certain of the results summarized here are also presented above in those Examples.

Deletion of the N-terminal $Val_1$ residue from VYIHPF (SEQ. ID. NO. 1) to produce YIHPF (SEQ. ID. NO. 33) reduced binding affinity to the bovine adrenal cortical AT4 receptor by 1000-fold. Addition of d-arginine to the N-terminal, (i.e., a peptidase analogue of AIII), reduced affinity by 100-fold. Deletion of the C-terminal Phe (i.e., des-Phe$_6$AIV) did not alter binding significantly. Further truncation of the C-terminal Pro$_5$, however, produced a moderate affinity (i.e., 21-fold less than AIV). Fragments containing less than positions #1 through #4 (i.e., N-VYIH-C; SEQ. ID. NO. 30) have K$_i$'s>500 nM. Addition of histidine to the C-terminus, (i.e., AI$_{(3-9)}$, FIG. 1), did not alter binding significantly, and further addition of leucine (i.e., AI$_{(3-10)}$ FIG. 1) reduced affinity by just 2-fold and resulted in data best plotted in Scatchard analysis to fit a two site binding model.

These results suggest that the binding domain in the AT4 receptor recognizes the N-terminus of AIV with a high degree of specificity. The receptor appears to interact less closely with the C-terminal region of AIV, but binding of receptors to this region of AIV may determine the receptor subtype specificity of AT4 receptors in different tissues.

Question #2. Does the binding site that interacts with the #1 residue in AIV (i.e., valine) exhibit any stereospecificity for particular orientations of the N-terminal residue?

Replacement of the L-valine$_1$ in AIV with D-valine$_1$ reduced binding affinity by 1000-fold. This indicates that the domain in the AT4 receptor binding site that interacts with the #1 position amino acid residue in AIV possesses a minimum of "4 non-planar ligand interacting sub-domains that have a fixed spacial orientation" that can be designated by the L-conformation of an L-valine amino acid. Examples of the latter "4 non-planar ligand interacting sub-domains" may be supplied by the side chain residues of 4 amino acids that appear in a requisite 3dimensional space within this subdomain of the receptor binding site. (Results discussed in response to Question #4, suggest that one of the 4 non-planar ligand interacting sub-domains interacts with the 1°-amine in the N-terminal amino acid.) Compounds that mimic the space filled by L-valine in a hydrophobic environment may mimic the interactions of L-valine with this subdomain of the receptor.

Question #3. Is the hydrophobic nature of the R$_1$-group (i.e., Val$_1$) in AIV a requirement for receptor binding and agonist activity?

Four analogues were synthesized and tested. Substitution of Val$_1$ with Ile$_1$ produced a slightly more hydrophobic peptide (i.e., IYIHPF; SEQ. ID. NO. 18) as determined by retention on reverse phase HPLC, and this peptide exhibited a slight increase in binding to AT4 receptors. Substitution of Val$_1$ with Phe greatly increased hydrophobicity but decreased binding affinity to the AT4 receptor by 4-fold. Surprisingly, substitution of Val$_1$ with Lys (i.e., KYIHPF; SEQ. ID. NO. 14) containing a positively charged side chain, greatly decreased hydrophobicity but increased binding affinity to the receptor by more than 45-fold. Substitution of Val$_1$ with a negatively charged side chain (i.e., Asp) resulted in an analogue (i.e., DYIHPF; SEQ. ID. NO. 34) with virtually no affinity for the AT4 receptor.

Figure 5A:
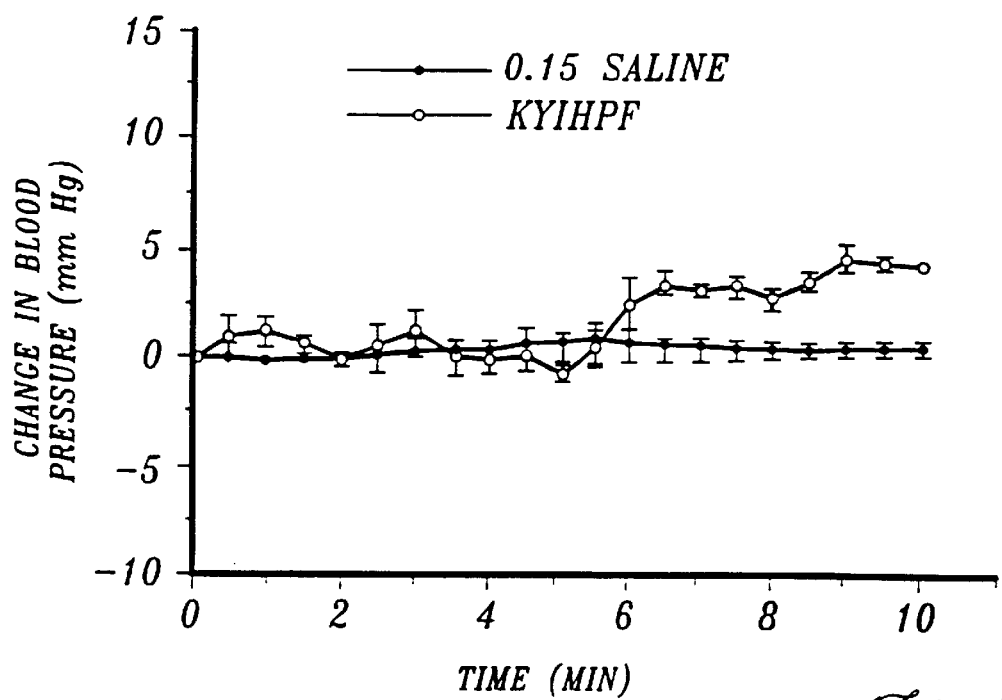
FIGS. 5A and 5B are graphical representations of changes in blood flow that result from binding of agonist, Lys$_1$AIV, to AT4 receptors in kidney, without changes in systemic blood pressure, as described in Example 4.
Figure 5B:
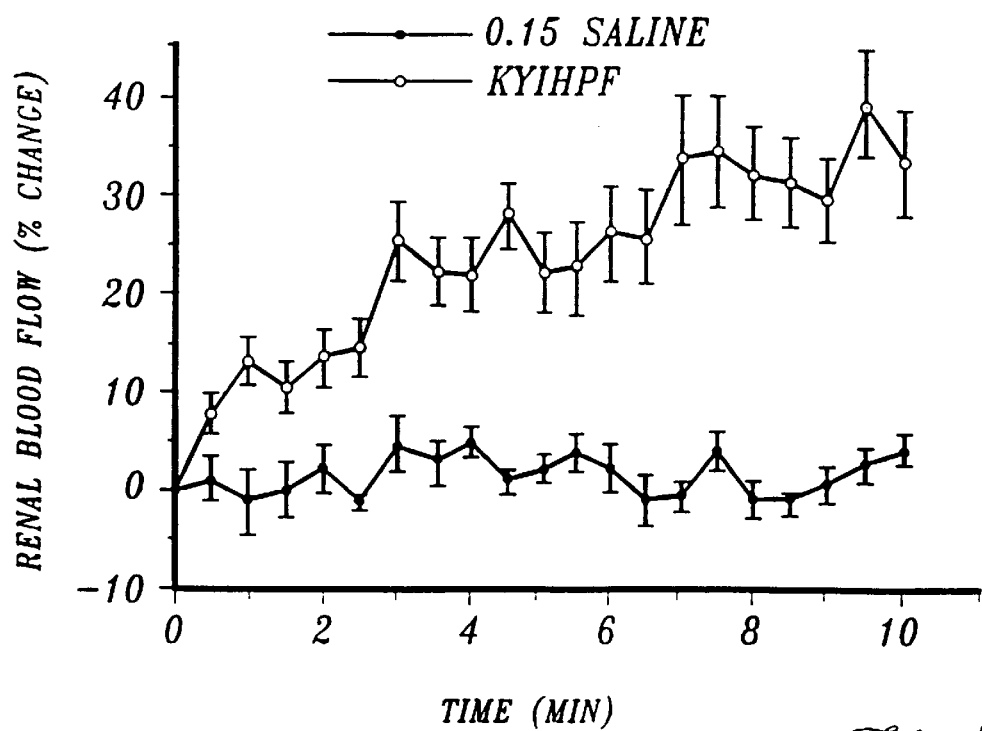
Figure 6A:
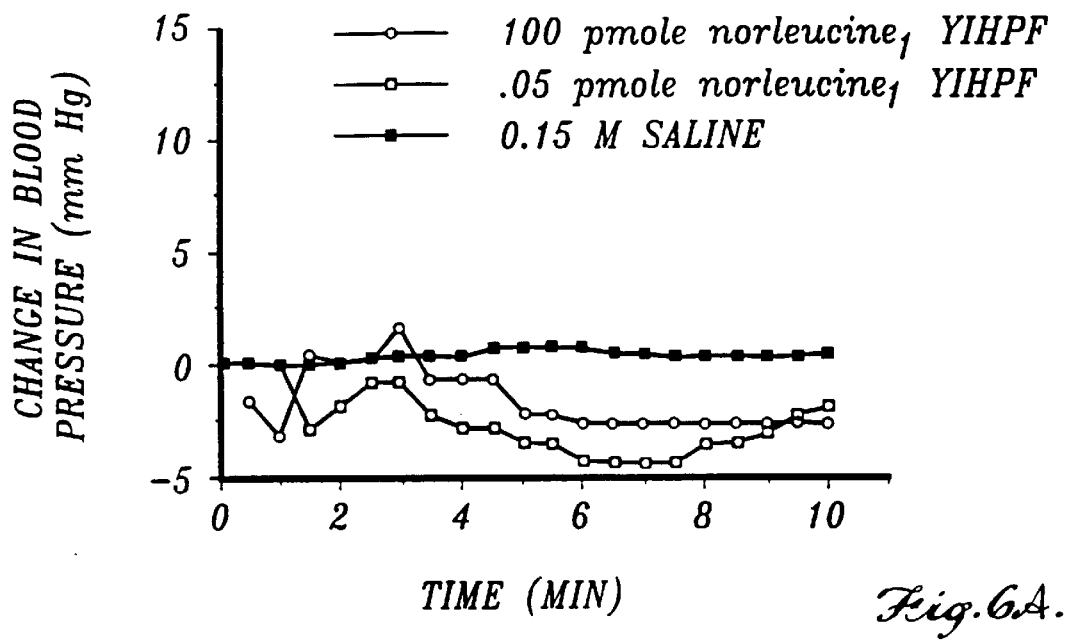
FIGS. 6A and 6B are graphical representations showing changes in blood flow that result from administering different doses of an agonist NorLeu$_1$AIV (i.e., NorLeuYIHPF; SEQ. ID. NO. 4) that binds to AT4 receptors in kidney, without changes in systemic blood pressure, sa described in Example 4. A therapeutically effective dose for increasing renal blood flow was achieved when doses greater than 50 fmole/25 µl/min were infused.
Figure 6B:
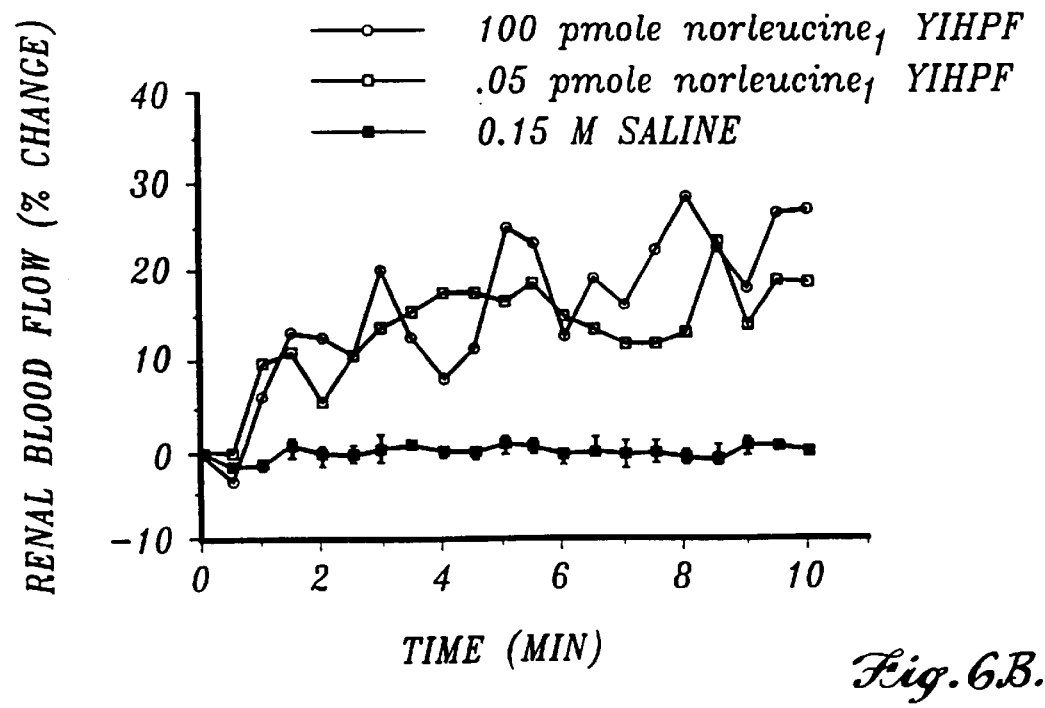

These results indicate that the nature of the R$_1$-group (i.e., a rigid aromatic ring versus a flexible aliphatic carbon chain having an optional positive charge) dictates the interaction with the binding site in the AT4 receptor, and not the just the degree of hydrophobicity of the amino acid residue. The results presented in FIGS. 5A and 5B also indicate that Lys$_1$-AIV (i.e., KYIHPF (SEQ. ID. NO. 14)) exhibits full (or increased) agonist activity relative to AIV (i.e., VYIHPF; SEQ. ID. NO. 1). FIG. 5 shows changes in blood flow that result from binding of agonist Lys$_1$-AIV (i.e., KYIHPF; SEQ. ID. NO. 14) to AT4 receptors in kidney, without changes in systemic blood pressure. Systemic arterial pressure and cortical renal blood flow were measured as described in Example 3, above. (No. of experiments=10.) FIG. 5A shows no significant changes in arterial blood pressure following administration of KYIHPF (SEQ. ID. NO. 14) at 100 pmole/25 ml/min (open circles) or saline control (closed circles). FIG. 5B shows changes in renal blood flow following administration of KYIHPF (SEQ. ID. NO. 14) at 100 pmole/25 ml/min (open circles) or saline control (closed circles), with the increased blood flow being equal to 38% of the maximum attainable with a strong vasodilatory agent (i.e., bradykinin, as described above).

Question #4. Does the primary (1°) amine in the N-terminal amino acid interact specifically with the Val$_1$-binding subdomain in the AT4 receptor binding site?

As described above in response to Question #2, Ile$_1$YIHPF (SEQ. ID. NO. 18) binds to the receptor with nearly the same binding affinity as VYIHPF (SEQ. ID. NO. 1). Methylation of Ile$_1$ in the latter peptide (i.e., to form N-methyl-Ile$_1$YIHPF; SEQ. ID. NO. 20) reduced bindng affinity for the AT4 receptor by 67-fold. Substitution of a secondary amine into the R$_1$ position of AIV (i.e., Pro$_1$YIHPF; SEQ. ID. NO. 21) reduced binding affinity to the AT4 receptor by 8-fold. Substitution of R$_1$ with benzoic acid (a partial structural analogue of Phe) or with 6-amino hexanoic acid (a structural analog of Lys) produced peptides with K$_i$'s>1 mM. Placement of GABA (gamma-aminobutyric acid) in the R$_1$ position decreased binding by 250-fold, i.e., relative to binding with AIV.

This data suggests that the receptor contains a binding site sub-domain that closely interacts with the primary amine function in the R$_1$ residue with respect to absolute space occupancy (volume) and probably a electrostatic charge, i.e., the receptor non-planar NH$_3$-binding component of the R$_1$-binding sub-domain (the same non-planar sub-domain component described in response to Question #1 above), most likely is a negatively charged residue that resides adjacent to the 1°-amine when the R$_1$ group is engaging the receptor sub-domain.

Question #5. Is the positive charge of the e-amine in Lys$_1$ responsible for the increased binding affinity of KYIHPF (SEQ. ID. NO. 14) to the AT4 receptor, or is this property attributable to the flexible, linear carbon chain?

Four different R$_1$ position MIV analogues were synthesized to answer this question: 1) Lys$_1$-substituted MIV (i.e., KYIBPF; SEQ. ID. NO. 14); 2) norleucine-substituted AIV, (i.e., NLe$_1$-YIHPF; SEQ. ID. NO. 4); 3) ornithine-substituted AIV (Orn$_1$-YIHPF; SEQ. ID. NO. 15); and, 4) norvaline-substituted AIV (i.e., Nva$_1$-YIHPF; SEQ. ID. NO. 35). The chemical structures of these side chains are shown in Table 10.

TABLE 10

Chemical Structures of Aliphatic Carbon Side Chains

| Lys | Nle | Orn | Nva |
|---|---|---|---|
| $CH_2$ | $CH_2$ | $CH_2$ | $CH_2$ |
| $CH_2$ | $CH_2$ | $CH_2$ | $CH_2$ |
| $CH_2$ | $CH_2$ | $CH_2$ | $CH_3$ |
| $CH_2$ | $CH_3$ | $NH_3^{\oplus}$ | |
| $NH_3^{\ominus}$ | | | |

NVa-substituted AIV had a 4-fold greater affinity for the AT4 receptor than Orn-substituted AIV. Nle-substituted AIV had a rem reversed phase HPLC (acetonitrile:triethylamine-phosphate, pH3) gradient method (12–18% over 60 min at 2ml/min).

Figure 11:
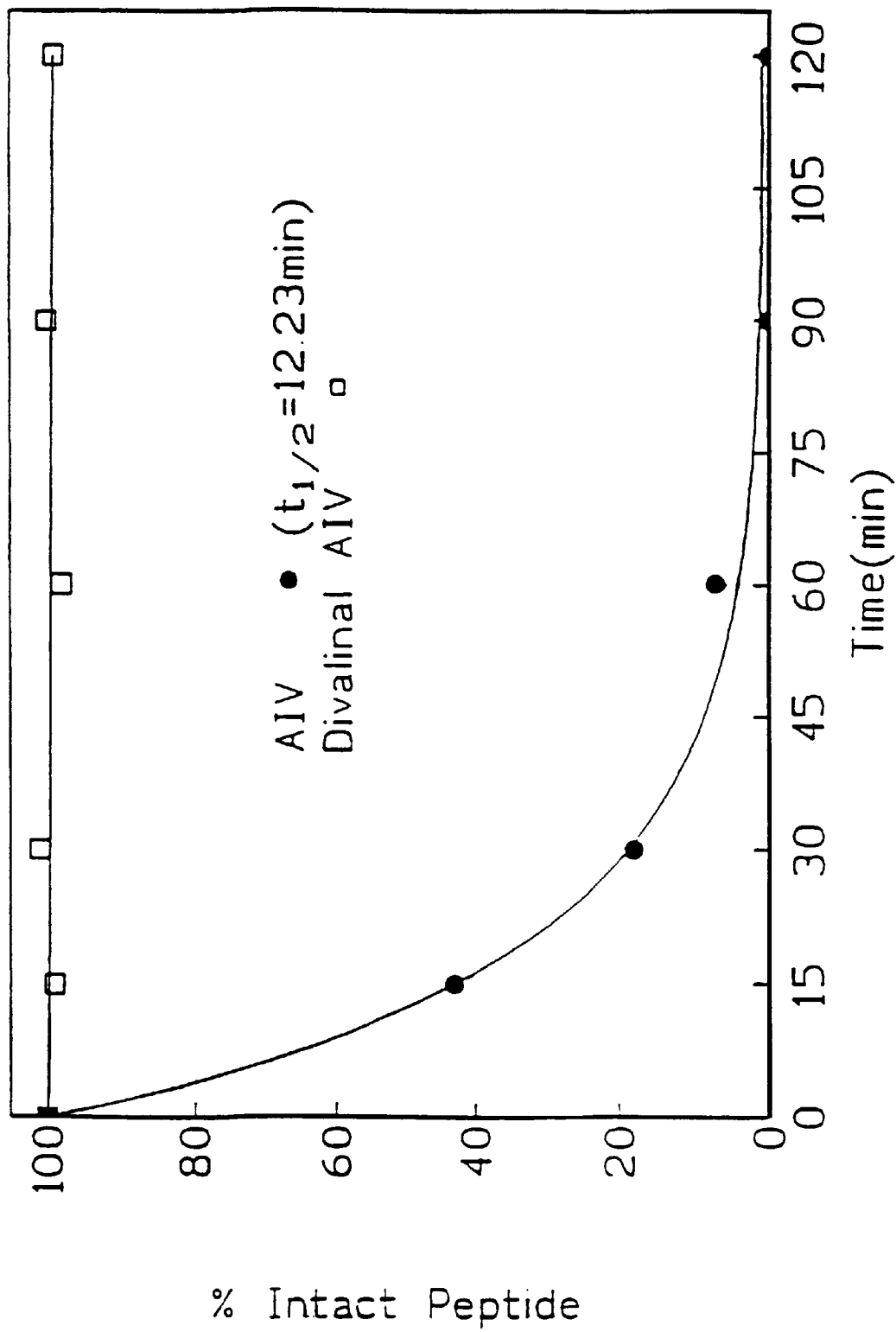
FIG. 11 is a graphical representation of the comparative stability of $^{125}$I-AIV (closed dots) and $^{125}$I-divalinal (or $^{125}$I-Val$_1$Val$_3$AIV, open squares) following exposure to rat kidney, as described in Example 4.

Replacement of the $R_1$–$R_2$ peptide bond with the methylene bond reduced affinity of binding to the AT4 receptor by 5-fold. Double replacement of both the $R_1$–$R_2$ and the $R_3$–$R_4$ peptide bonds and substitution of the $R_3$ Val with Ile produced the peptide: N—$V_1$—$CH_2$—NH—$Y_2V_3$—$CH_2$—NH—$H_4P_5F_6$—C (SEQ. ID. NO. 25) (Divalinal AIV) that had equal or better affinity than AIV for the AT4 receptor. In addition, divalinal AIV has been shown to exhibit enhanced metabolic stability and to be a potent antagonist of AT4 receptor activity. FIG. 11 illustrates the comparative stability of $^{125}$I-AIV and $^{125}$I-Dival AIV following exposure to a membrane fraction prepared from rat kidney. Kidney was chosen as the tissue of study because of its well-known degradative capacity. The metabolish of $^{125}$I-AIV and $^{125}$I-Dival AIV by rat kidney membranes was determined as follows: Rat membranes (25 µg protein) were incubated with 0.6 nM $^{125}$I-peptide at room temperature in a buffer containing Tris, 50 mM, pH7.4; NaCl, 150 mM; BSA, 0.1%; EDTA, 5 mM; bestatin, 20 µM; and Plummer's inhibitor, 50 µM. Metabolism was stopped by the addition of acetonitrile (final concentration 50%), and the samples were analyzed by reverse phase ($C^{18}$) HPLC. As can be seen in FIG. 11, AIV is rapidly degraded while Dival AIV remains 100% intact after 4 hr of incubation.

Figure 12A:
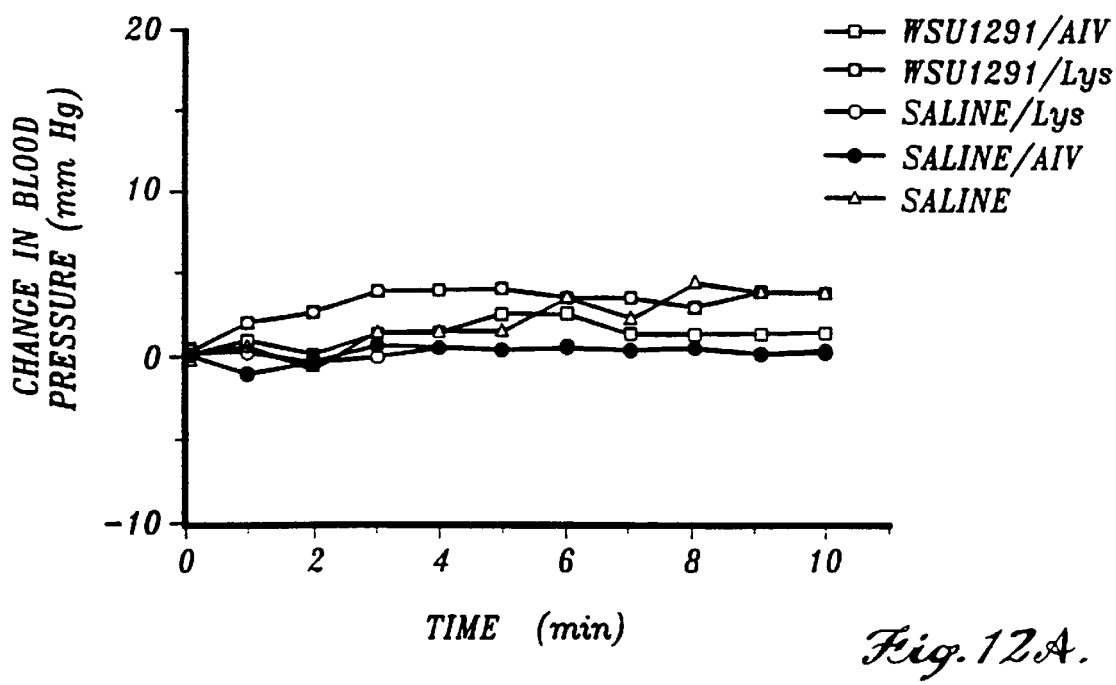
FIGS. 12A and 12B are a graphical representation of the effects of divalinal AIV (open squares), and divalinal AIV followed by Lys$_1$AIV (squares with dots), on blood pressure (FIG. 12A) and renal blood flow (FIG. 12B), as compared to saline alone (triangles), saline followed by AIV (closed circles) and saline followed by Lys$_1$AIV (open circles), as described in Example 4.
Figure 12B:
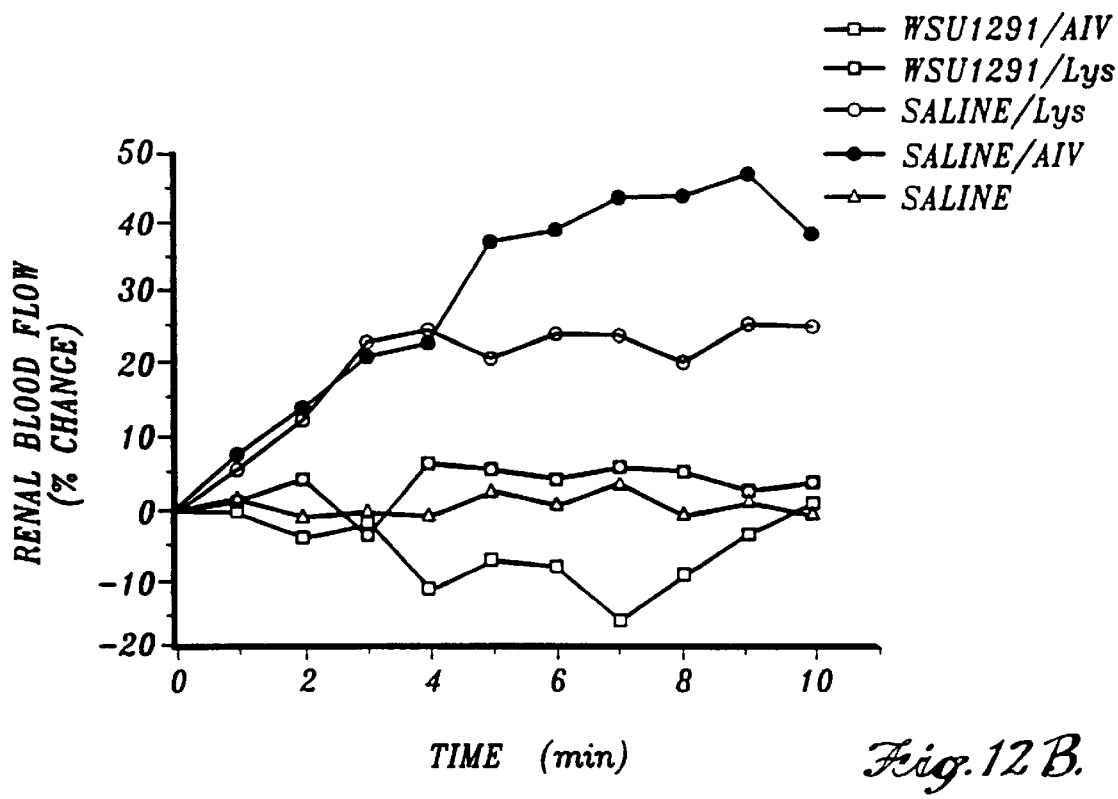

In addition, following the procedures of Examples 4 and 6, it has been found that preinfusion with divalinal AIV completely blocks Lys$^1$AIV-induced increases in blood flow, and preinfusion with divalinal AIV actually transforms AIV's effects on blood flow from an increase to a decrease. This effect of divalinal AIV on AIV suggests that AIV also acts at AII receptors, the effects of which are normally masked by AIV's action on $AT_4$ receptors. Divalinal AIV treatment by itself did not alter blood pressure or renal blood flow (FIG. 12A). Additionally, it had no effect on AIV-induced decreases in blood flow (FIG. 12B).

It has been further found that AIV potentiates the performance of rats in a passive avoidance task in a dose-dependent manner while AII exhibited no specific effect. In this experiment, the mean latency (see ±SEM) for independent groups of rats to reenter the dark compartment following passive avoidance conditioning on Day 1. On Day 1 (5 min prior to testing for retention) the Control Group received 2 µl aCSF, angiotensin II (AII), AIV, or divalinal AIV. Each group except the divalinal AIV revealed significant elevations in latency to reenter the dark compartment—comparing Days 1 and 2. In addition, the groups that received 100 pmole or 1 nmole of AIV indicated a significant elevation in latency to reenter compared with those groups that received aCSF and AII, while these latter groups did not differ from each other. Rats treated with divalinal AIV were not statistically different from preshock controls. Interestingly, treatment of rats with divalinol AIV blocked the typical increase in latency seen in control rats. Responses by rats treated with divalinal AIV were not statistically different than preshock controls. These data indicate that while AIV potently enhanced cognitive function, divalinal AIV acting as an AIV antagonist completely blocks the learning and/or retrieval of the passive avoidance task. Furthermore, these data suggest that endogenous AIV must play a critical role in cognitive function.

These results indicate that the AT4 receptor binding site domain binds analogues in which the peptide bond has been replaced with a non-carbonyl (non-peptidase sensitive) bond that has a similar bond length, and that is non-planar and has a non-rigid carbon-nitrogen bond. Non-peptide bonds offer pharmacological advantages for a therapeutic composition, i.e., prolonged half-life.

Question #8. What determines agonist versus antgonist activity? Both AIV (i.e., VYIHPF; SEQ. ID. NO. 1) and Lys$_1$-AIV (i.e., KYIHPF; SEQ. ID. NO. 14) exhibit full agonistic activity, while Nle$_1$-AIV (i.e., NleYIHPF; SEQ. ID. NO. 4) is only a partial agonist. The model capable of explaining this behavior has the following component parts:

a) The receptor binding site sub-domain interactions with the side groups (i.e., of $R_1$) determines receptor activation;

b) The interaction at the $R_1$-sub-domain binding site involves a hydrophobic pocket;

c) The space in the latter hydrophobic pocket conforms very closely with the 4 carbon side chain of norleucine;

d) Nle$_1$ (i.e., in Nle$_1$YIHPF; SEQ. ID. NO. 4) interacts with the hydrophobic pocket without changing the conformation of the pocket;

e) Val$_1$ (i.e., in VYIHPF; SEQ. ID. NO. 1) must occupy an "expanded" hydrophobic pocket, i.e., where the receptor hydrophobic pocket is displaced laterally to accomodate the branched carbon side chain in these residues. Lys$_1$ (i.e., in KYIHPF; SEQ. ID. NO. 14) must similarly occupy an "expanded" hydrophobic pocket because of the charge repulsion from the hydrophobic "walls" of the pocket; and, f) The process of "expanding" the hydrophobic pocket constitutes a molecular trigger for the process transitioning the receptor from the "pre-binding state" to the "binding state".

To study the properties of the "hydrophobic pocket" subdomain of the AT4 receptor binding site it is useful to prepare derivatives of Orn$_1$ (i.e., Orn$_1$YIHPF; SEQ. ID. NO. 15) at the delta amino group to: a) the charge of the group; b) place a planar, conformationally-fixed bond in the 4 carbon side-chain group that will inhibit binding in the hydrophobic pocket if the "walls" of the pocket are unable to move to accomodate the space required by the conformation; and, c) synthesize conformationally-fixed bonds in carbon side-chains of different length (e.g., 3–5 carbons) to explore the optimal longitudinal dimensions of the flexible wall space in the receptor pocket. Suitable N-delta groups for this exploration are acetate, propionate, benzoic acid, isobutyric acid, and trimethyl acetic acid.

Question #9. Can the shorter peptide AIV$_{(1-4)}$ analogues (e.g., VYIH; SEQ. ID. NO. 30) be converted to high affinity ligand by norleucine substitution at position $R_1$?

Answers to this question provide tetrapeptides agonists and antagonists whose interactions with the AT4 receptor are easier to molecularly model, and mimic. The peptides Nle$_1$-AIV$_{(1-5)}$ (i.e., NleYIHP; SEQ. ID. NO. 4), Nle$_1$-AIV$_{(1-4)}$ (i.e., NleYIH; SEQ. ID. NO. 4), and Nlel-AIV$_{(1-3)}$ (i.e., NleYI) may be useful for testing space-filling modifications that can be made to alter binding in the receptor binding site sub-domains. It is considered highly likely that independent modifications that can be made to alter the binding of the latter small Nle$_1$ peptides into the AT4 receptor binding site sub-domains will be paralleled when the modification are incorporated into larger AIV ligands.

Question #10. Will substitution of Ile$_1$ at position $R_6$ (e.g., to form VYIHPI (SEQ. ID. NO. 37), KYIHPI (SEQ. ID. NO. 26), or NleYIHPI (SEQ. ID. NO. 38) create antagonist activity?

Three Ile$_6$ substituted AIV analogues were synthesized (Val$_1$Ile$_6$-AIV, Lys$_1$Ile$_6$-AIV and Nle$_1$Ile$_6$-AIV). When tested for in vitro receptor binding activity Val$_1$Ile$_6$-AIV had a higher binding affinity for the AT4 receptor than AIV (i.e., VYIHPI (SEQ. ID. NO. 37)>VYIHPF (SEQ. ID. NO. 1)); and $Lys_1Ile_6$-AIV had a lower affinity than $Lys_1$-AIV (i.e., KYIHPI (SEQ. ID. NO. 26)<KYIHPF (SEQ. ID. NO. 14)).

The results suggest that the AT4 receptor binding site is a multi-domain binding site with interactions such that binding in one sub-domain (e.g., within the hydrophobic pocket of the $R_1$ sub-domain) can be excluded by high affinity binding at a distant sub-domain site (e.g., within the sub-domain with specificity for the C-terminal $Ile_6$ or $Pro_5$ residues; i.e., at the $R_6$ subdomain binding site in the receptor). The induced-fit model supplied above in response to Question #8 is compatible with the observed exclusionary binding properties: i.e., binding of $R_1$ hydrophobic pocket that constitutes the $R_1$-binding subdomain requires flexibility of expansion in the pocket, and binding of $R_6$ in the $R_6$ sub-domain binding site confers a rigidity to the receptor that inhibits flexibility in the $R_1$-binding subdomain.

Materials and Methods:

Binding was carried out as described in Example 1, above, in siliconized glass culture tubes containing 0.2 nM $^{125}$I-AIV, 25 μg of membrane protein, and the desired analogue over a concentration range of $10^{-12}$ to $10^{-4}$M using half-log dilutions. All binding incubations were carried out in duplicate at 37° C. for 2 h in a buffer containing: 50 mM Tris, 150 mnM NaCl, 5 mM EDTA, 10 μM bestatin, 50 μM Plummer's Reagent, 100 μM PMSF and 2% BSA (Assay buffer) in a total volume of 0.25 ml. After incubation, the incubation mixtures were filtered through glass fiber (GF-B) filters soaked in 0.3% polyethyleneimine and washed with 4—4 ml washes of PBS. The filters were then counted on a Beckman 5500 gamma counter. A typical experiment examined 5 analogues simultaneously and included a positive control curve in which non-radiolabeled AIV ligand was used as the displacer to inhibit binding of $^{125}$I-AIV to the AT4 receptor. All samples were run in quadruplicate, each with a different tissue preparation. Data was analyzed by the LIGAND program (29) from which $K_i$ values were obtained. AIV analogues that are peptides were synthesized by the standard Merrifield method utilizing t-Boc protected amino acids and chloromethylated resins on a Vega 250 coupler automated synthesizer (as described in Example 1, above). Following synthesis, the crude peptides were purified by preparative reverse-phase HPLC. The amino acid composition of the purified peptides was determined with respect to both composition and total purity. Typically the peptides used in these studies were greater than 99% pure and contained about 20–25% acetate.

EXAMPLE 5

Vascular Effects of the AIV Ligand-AIV Receptor Interactions

In endothelial cells (such as bovine coronary venular endothelial cells), it has been reported previously that these cells may play a critical role in angiogenesis (review, 21). In one study by others angiotensins were reported to be capable of stimulating angiogenesis (22). However, studies in the inventors' laboratory over the past ten years have failed no less than six times to demonstrate detectable levels of AII receptors in preparations of endothelial cells that were free of smooth muscle contamination (a finding contradictory to one report that AII receptors may be present on endothelial cells, (23). In addition, AII and $Sar_1,Ile_8$-AII have been reported to stimulate bovine endothelial cell proliferation (24), but the possible mechanisms were not clear, especially in light of other studies reportedly showing that AII and $Sar_1,Ile_8$-AII were rapidly metabolized in tissues and biological fluids to smaller metabolites. In light of the present disclosure it is now clear, in hindsight, that hydrolysis of AII or AIII to AIV can result in binding of AIV to AT4 receptors on endothelial cells with triggering of cell proliferation, and may possibly be involved in the initiation of hyperplastic growth of endothelial cells or vascular smooth muscle cells.

AT4 receptors in vascular cells

The following study describes the characteristics of a new class of angiotensin binding sites in vascular endothelium that exhibit high specificity and affinity for hexapeptide AIV. Analysis of $^{125}$I-AIV binding was performed in membrane fractions of two endothelial cell lines, bovine coronary venular endothelial cells (CVEC) and bovine aortic endothelial cells (BAEC). Kinetic analysis of binding indicated that equilibrium was reached in 60 min. at 37° C., remained stable for at least 4 h, and produced a calculated kinetic $K_d$ of 0.3 nM. Saturation equilibrium binding studies analyzed by non-linear curve fitting suggested the following two site models (mean +/− SEM): CVEC $K_{d1}$=14.6 +/−26.5 pM, $B_{max1}$=6 +/−1 fmol/mg protein, $K_{d2}$=4.4 +/−0.8 nM, $B_{max2}$=434 +/−51 fmol/mg protein. Competition binding curves from CVEC demonstrated high specificity of the receptor for for AIV. The competitive binding affinities of analogues to the receptor showed affinities that (in decreasing order) were AIV>$AII_{(3-7)}$>AIII >AII>$Sar_1Ile_8$-AII, or $AII_{(4-8)}$>>DUP 753, or CGP42112A. The AT4 receptor in endothelial cells may not be G-protein linked because the non-hydrolyzable GTP analog GTPγS had no effect on $^{125}$I-AIV binding to receptors in BAEC cells. These data indicate that AIV binds to a site in vascular tissues that is distinct and separate from the classic AT1 or AT2 angiotensin receptors.

Kinetic binding studies

Kinetic analysis of $^{125}$I-AIV binding to AT4 receptors in CVEC membrane revealed that equilibrium was reached in approximately 60 min. and remained stable for at least 4 h. at 37° C. (FIG. 7A). The kinetic properties of $^{125}$I-AIV binding to AT4 receptors in membrane fractions of bovine coronary venular endothelial cells (CVEC) at 37° C. are shown in FIGS. 7A and 7B. The association (FIG. 7A) and dissociation (FIG. 7B) rate constants for binding of 0.6 nM $^{125}$I-AIV were $9.3\times10^7$ $M^{-1}min^{-1}$ and 0.028 $min^{-1}$, respectively. The kinetic $K_d$ calculated from these rate constants is 0.3 nM. Calculations were performed by the LIGAND program from a mean of four experiments with duplicate samples. Data presented here represent the results from a single experiment.

Analysis of association data under pseudo first order rate conditions resulted in an observed association rat constant ($k_{obs}$)=0.084 +/−0.013. The dissociation rate constant ($k_{-1}$)= 0.028 +/−0.005 $min^{-1}$ was estimated by the addition of 1 mM undlabeled ligand following incubation of 0.6 nM $^{125}$I-AIV for 120 min at 37° (FIG. 7B) and the actual association rate constant ($k_1$) was calculated to be $9.3\times10^7$ $M^{-1}min^{-1}$. Based on these rate constants, the apparent kinetic $K_d$ value is 0.3 nM. Less than 10% degradation of the ligand occurred under the binding conditions used here.

Equilibrium binding studies

As shown in FIGS. 7A and 7B, quilibirum binding of $^{125}$I-AIV to AT4 receptors in CVEC and BAEC membranes reached saturation at 37° C. in 120 min. Equilibrium saturation binding and Scatchard transformation analysis (insert) for 125I-AIV binding to AT4 receptors in CVEC is shown in FIG. 7A, and BAEC in FIG. 7B, membrane fractions after 120 min. at 37° C. The data were best fit by a two site model utilizing the non-linear curve fitting program LIGAND (No. of expts.=4, each with duplicate samples).

Figure 7A:
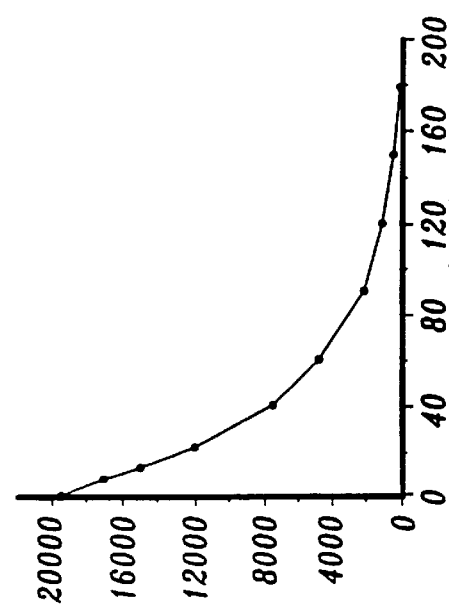
FIGS. 7A–7D, 8 and 9 are graphical representations of AIV binding, as described in Example 6.
Figure 7B:
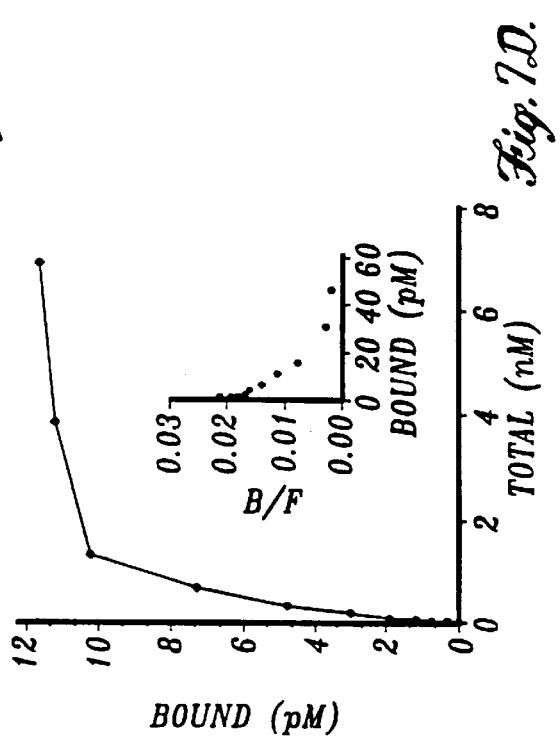
Figure 7C:
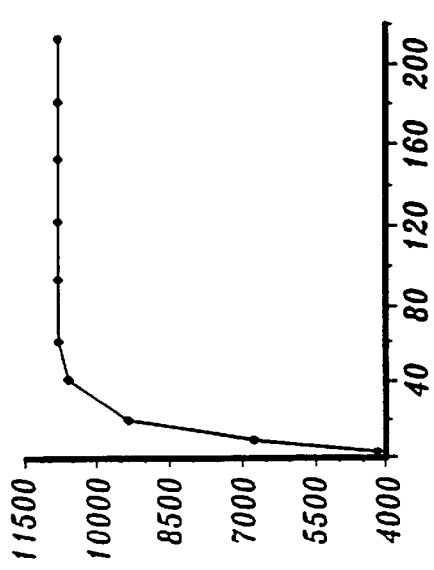
Figure 7D:
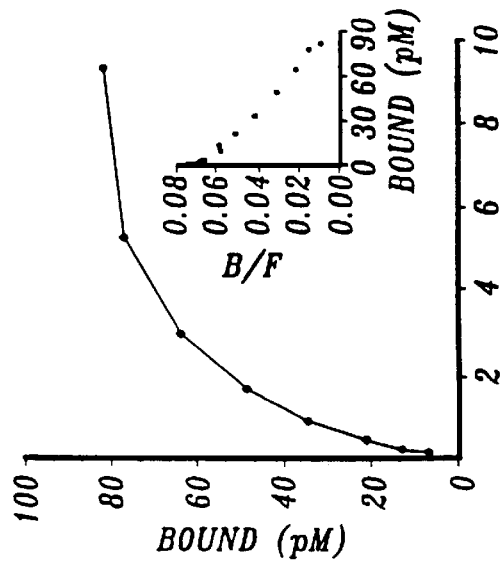

Scatchard transformation of these data suggested the presence of multiple binding sites in endothelial cell membrane-associated AT4 receptors. The data were best resolved into two components corresponding to a high and a low affinity binding site. The final $K_d$ and $B_{max}$ values were as follows:

In CVEV (FIG. 7A): site #1 14.6 +/−26.5 pM with 6 +/−1 fmol/mg protein; site #2 1.4 +/−0.2 nM with 594 +/−4 fmol/mg protein; and, In BAEC (FIG. 7B): site #1 26.9 +/−9 pM with 10 +/−2 fmol/mg protein; site #2 4.4 +/−0.8 nM with 434 +/−51 fmol/mg protein.

Values obtained when fitting the data to a single receptor affinity site model were: in CVEC 0.7 +/−0.1 nM Kd with $B_{max}$=10 +/−2 fmol/mg protein; and in BAEC 1.0 +/−0.2 nM with $B_{max}$=260 +/−38 fmol/mg protein. The two site model produced a significantly better fit for both cell types as compared with the single site model (i.e., F-test, p<0.001).

Competition binding studies

Figure 8:
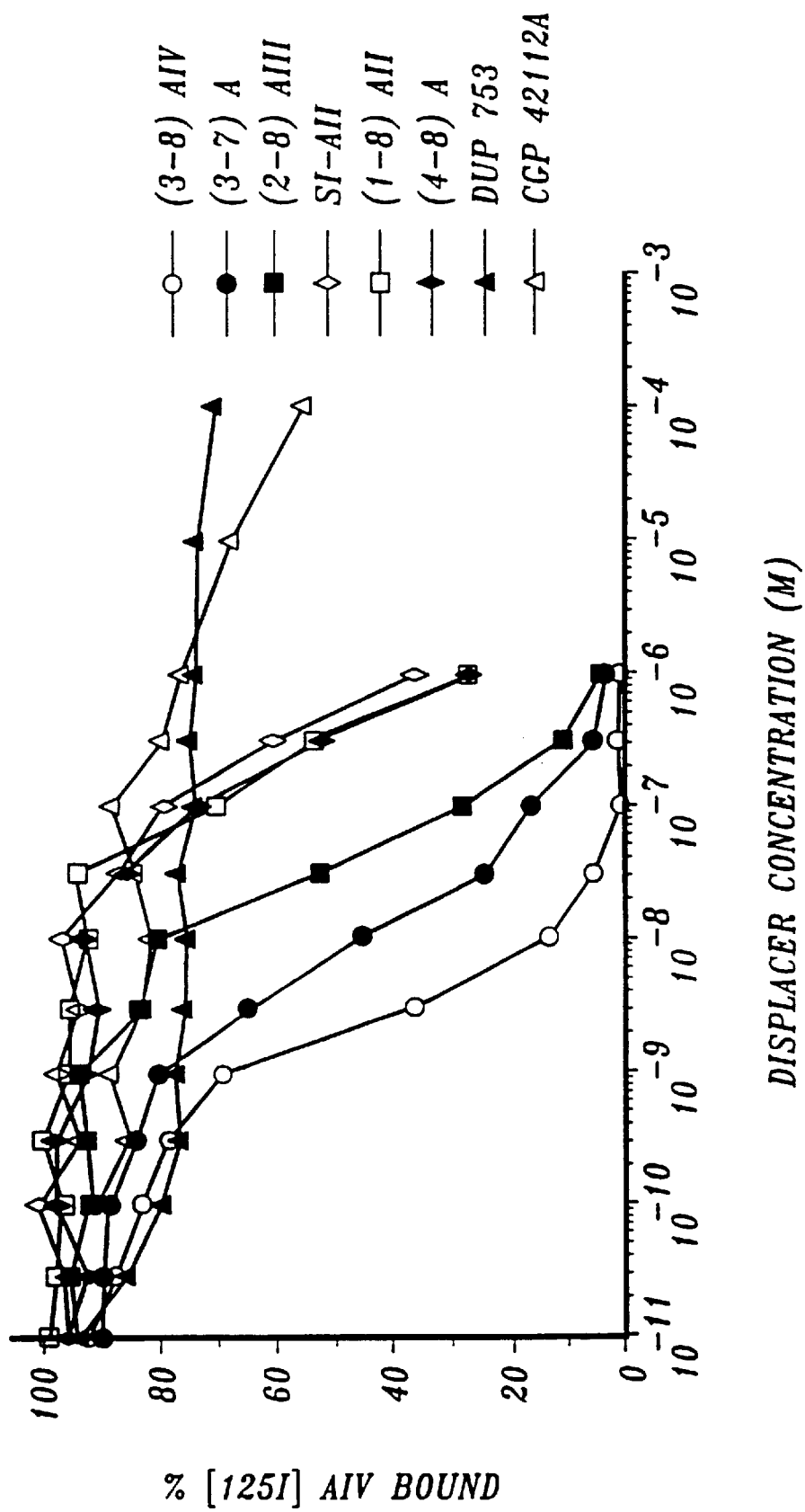

Competition studies were conducted to displace $^{125}$I-AIV binding to AT4 receptors in CVEC membrane preparations with specific ligand, i.e., AIV, and other related angiotensin fragments. FIG. 8 shows competition displacment curves delineating the ability of angiotensin fragments to inhibit specific binding of 0.5 nM $^{125}$I-AIV to AT4 receptors in membrane preparations of bovine coronary venular endothelial cells (CVEC). (No. of exper. =2; each conducted with duplicate samples.)

The rank order affinity of competitive analogues competitively displacing bound AIV from its receptor were as follows: AIV>$AII_{(3-7)}$>AIII>AII >$Sar_1Ile_8$-AII, or $AII_{(4-8)}$ >>DUP 753, or CGP42112A. (For sequences of AII analogues see FIG. 1). The results of these studies are summarized in Table 11.

TABLE 11

Competition of $^{125}$I-AIV binding to AT4 receptors in CVEC membrane preparations

| Fragment | Sequence | $K_i$ |
|---|---|---|
| AIV | VYIHPF | 1.1 +/− 0.2 nM |
| $AII_{(3-7)}$ | VYIHP | 7.3 +/− 1.2 nM |
| AIII | RVYIHPF | 23.3 +/− 3.4 nM |
| $AII_{(1-8)}$ | DRVYIHPF | 193.8 +/− 44.5 nM |
| $AII_{(4-8)}$ | YIHPF | 252.6 +/− 89.1 nM |
| $Sar_1$,$Ile_8$-AII | SRVYIHPI | 261.0 +/− 89.1 nM |
| DUP 753 | — | $>10^{-4}$ |
| CGP 42112A | — | $>10^{-4}$ |

*All values represent mean +/− SEM of two experiments with duplicate samples; $K_i$ determined by LIGAND.

G-protein linkage of the AT4 receptor in vascular cells

G-protein interactions with vascular angiotensin receptors are shown in FIG. 9, where membrane fractions from rat vascular smooth muscle cells (RVSMC) or bovine aortic endothelial cells (BAEC) were preincubated in various concentrations of a non-hydrolyzable GTP analogue (i.e., GTPγS) for 60 minutes at 22° C. prior to use in equilibrium binding assays with 0.5 nM $^{125}$I-AII (RVSMC) or 0.6 nM $^{125}$I-AIV (BAEC). (No.1 of exper.=3; each with duplicate samples.) Data presented here represent results from a single experiment.

Addition of non-hydrolyzable GTP (i.e., GTPγS) to the binding assays did not inhibit (or alter) binding of $^{125}$I-AIV to AT4 receptors in BAEC membrane preparations (FIG. 9). In constrast, in a positive control GTPγS inhibited $^{125}$I-AII binding to AT1 receptors in rat vascular smooth muscle cell (RVSMC) membrane preparations in a dose-dependent manner (FIG. 9); in agreement with observations reported previously by others. (This property distinguishes AT4 receptors of the invention from AT1 and AT2 receptors reported by others previously in vascular tissues.)

Discussion

This study is the first to describe a novel angiotensin binding site in vascular endothelium that exhibits high affinity and specificity for the hexapeptide AIV fragment of angiotensin AII. The AT4 receptor is distinct from the AT1 or AT2 receptors in vascular tissue. Analysis of the binding characteristics indicates that the AT4 receptor binds AIV in a saturable and reversible manner, and that $^{125}$I-AIV reaches equilibrium in binding to the AT4 receptor in membrane preparations in approximately 60 min. at 37° C. Binding of AIV to its receptor remains stable for at least 4 h (FIG. 7A) with less than 10% degradation of the ligand under these binding conditions. Scatchard analysis of the AT4 receptor binding site by the non-linear curve fitting program LIGAND reveals two components to the binding data. The first component is a high affinity component that exhibits $K_d$'s of 14 and 27 pM with $B_{max}$'S of 6 and 10 fmol/mg protein for receptors in CVEC and BAEC membrane preparations, respectively. (Because of the extremely low number of these high affinity sites it is unclear at present whether this is a physiologically important state of the receptor; or, is a result of modification of AT4 receptors in the membrane preparations, or changes in receptor binding affinity resulting from co-operative binding of AIV; or alternatively, that this site is an artifact created in the membrane preparations or assay conditions.) The second binding component is a lower affinity component with $K_d$'s of 1.4 and 4.4 nM (i.e., in CVEC and BAEC, respectively). The second component displays a high concentration of ligand binding commensurate with large numbers of such receptor sites in the membrane preparations: i.e., these sites bind 594 and 434 fmol/mg protein in CVEC and BAEC membrane preparations, respectively.

The overall binding affinity (i.e., $K_d$, single or composite site fit produced by LIGAND) was calculated to be 0.7 nM for CVEC and 1.0 nM for BAEC. These results are in good agreement with the $K_d$ calculated from the results of kinetic binding studies (0.3 nM).

The pharmacological profile derived from competition displacement of $^{125}$I-AIV bound to these AT4 receptors in vascular tissues is presented in FIG. 8 and Table 11, above. This profile reveals a strict structural requirement for the N-terminus of the AIV ligand, i.e., removal of the N-terminus ($Val_1$) of the AIV ligand results in a 200-fold decrease in affinity of the AIV ligand for the AT4 receptor in vascular tissues (i.e., an increase in the $K_i$). In addition, N-terminal extension, i.e., beyond $Val_1$, is detrimental to the binding of AIV ligands to the vascular AT4 receptor as indicated by the inability of AII and $Sar_1$,$Ile_8$-AII to competitively inhibit binding of AIV to the AT4 receptor, (i.e., note the 200-fold increase in $K_i$ seen with AII and $Sar_1$,$Ile_8$-AII, when compared with AIV in Table 11). (This property distinguishes AT4 receptors of the invention from AT1 and AT2 receptors.) The apparent affinity of AIII for the vascular AT4 receptor (i.e., 20-fold higher $K_i$ than AIV, Table 11) may be an artifact of N-terminal metabolism of AIII to form AIV in these membrane preparations. (In previous studies, above, $^{125}$I-AIII binding to bovine adrenal AT4 receptors was directly proportional to the amount of AIII hydrolyzed to AIV.)

The vascular AT4 receptor appears to exhibit less specificity for the C-terminus than exhibited for the N-terminus: i.e., the $AIV_{(1-7)}$ fragment (with the C-terminal $Phe_8$ deleted still bound with reasonable affinity to the receptor (i.e., only a 7-fold increase in $K_i$ over AIV). (These findings are in agreement with the findings above in Example 1 using AT4 receptors in bovine adrenal cortical tissues.)

The vascular AT4 receptors do not apparently bind either DUP 753 or CGP 42112A (i.e., $K_i > 10^{-4}$), but AT1 or AT2 receptors are well-known to do so (Timmermans, P. et al. TIPS 12:55–62, 1991; Whitebread, S. et al. Biochem. Biophys. Res. Comm. 163:284–291, 1989). (This property of failure to bind either DUP 753 or CGP 42112A distinguishes AT4 receptors of the invention from AT1 and AT2 receptors.)

Figure 9:
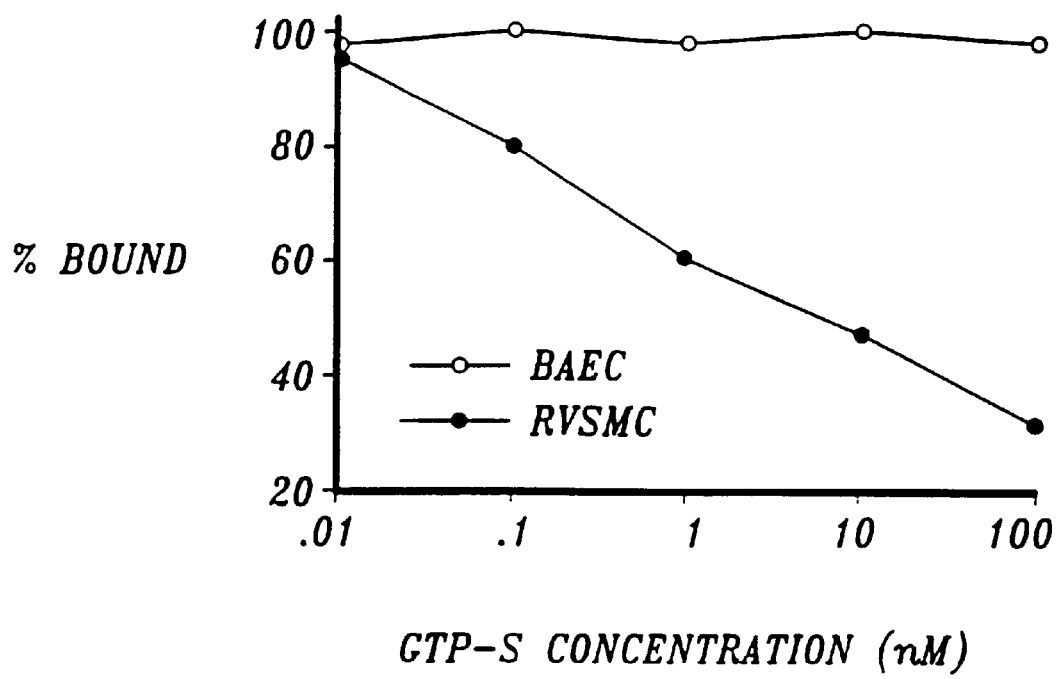

Binding of $^{125}$I-AIV to vasular endothelial AT4 receptors was not sensitive to inhibition by guanine nucleotides. In contrast, binding of AII to AT1 and AT2 receptors in membrane preparations of rat vascular smooth muscle cells (RVSMC; FIG. 9) was sensitive to inhibition by guanine nucleotides in a dose-dependent manner, i.e., the affinity of the AT1 receptor for AII was shifted to a lower value when the receptor was uncoupled from G-proteins by the presence of the GTP analogue GTPγS (FIG. 9). This shift in binding affinity in response to gunaine nucleotides is a characteristic of the high affinity form of the AT1 receptor (Glossmann, H. et al. J. Biol. Chem. 249:664–666, 1974). The insensitivity of the AT4 receptor to G-protein uncoupling agents was also observed with AT4 receptors in membrane preparations of bovine adrenal cortex. (This property of insensitivity to G-protein uncoupling agents distinguishes AT4 receptors of the invention from AT1 and AT2 receptors.)

Despite the inability of AIV to bind to AII receptors, several recent studies have suggested that that AIV-like fragments of AII may have unique biological attributes. In cultured chick myocytes, AIV-like fragments of AII have been reported to antagonize the effects of AII-induced increases in cytosolic free calcium, protein synthesis, and hypertrophic cell growth while being unable to competitively inhibit for $^{125}$I-AII binding (Baker, K. M. et al. Am. J. Physiol. 259:H610–H618, 1990). Topical application of both AII and AIV-like fragments of AII have been reported to mediate endothelium-dependent vasodilation in rabbit brain arterioles. However, in the presence of the amino peptidase inhibitor amastatin, the vascular response to AII, but not AIVlike fragments, was reportedly blocked (Haberl, R. L. et al. Circ. Res. 68:1621–1627, 1991). AIV-like AII fragments and AII have also been reportedly applied intracerebroventricularly in the rat where they reportedly are equipotent in enhancing memory and learning (Braszko et al. Brain Res. 542:49–54, 1991). Given the low affinity of AIV for AT1 and AT2, disclosed herein, it is most likely that the latter activities previously attributed to binding of AII and/or AIV-like fragments at AT1 and AT2 sites are, in fact, the result of binding of AIV at the AT4 receptor sites of the invention.

It is likely that the actions evoked by AIV binding to its specific AIV receptors may act contrary to the actions of the AII and AT1 and AT2 receptors. For example, infusion of AIV into rat kidney, as shown above, to stimulate a significant increase in blood flow in the renal cortex, while AII binding to AT1 and AT2 receptors in these tissues produces the converse effect—a significant decrease in blood flow.

Effects on Vascular Tissues:

Assessment of AIV effects on the contractile properties of aorta and inferior vena cava was demonstrated using tissues from rabbits. The presence of numerous AT4 receptors in aortic tissue suggest a possible action of AIV ligand on cerebral vessels. The routine use of rabbit aortic strips or rings in cardiovascular pharmacology dictate that rabbits are suitable for use in such studies.

The following protocols are useful for: 1) confirming the vasodilating potential of an AIV ligand, demonstrating that ligand action is dependent on an AT4 receptor, and showing that the action is independent of AI or AII receptors; 2) establishing that any observed vasodilation is endothelium dependent; 3) determining whether the mechanism of vasodilation involves prostaglandins, EDRF, or other factors like EDHF as second messengers; and 4) determining the functionality of the many AIV analogues (i.e., such as those synthesized in Example 4) as either AIV ligands or as agonists, antagonists, inhibitors, or promoters of the AIV ligand-receptor interaction.

AIV and AII ligands and various analogues (Example 4) in the presence or absence of angiotensin inhibitors (e.g., $Sar_1$,$Ile_8$-AII, DUP 753, and CGP42112A) were screened for the vasodilating activity using rabbit aorta and inferior vena cava rings or spiral strips suspended in 20 ml organ baths containing Krebs solution at 37° C. and continuously gassed with 5% $CO_2$ in oxygen. After a 1 h equilibration period, cumulative dose-response curves were constructed for the analogues over a concentration range of $10^{-10}$M to $10^{-5}$M. In relaxation studies, aortic strips were precontracted to 70% of maximum diameter with phenylephrine, and then the test ligand is added and relaxation of the vessel is quantified. Changes in contractile or relaxant response may be calculated for each dose of each different ligand or analogue and subsequently analyzed by analysis of variance.

Effects on Endothelial Cells:

The effect of AIV ligand on endothelial cells was examined by measuring growth of bovine endothelial cells. Cells were grown at 37° C. in 35 mm culture plates $CO_2$/air under 5% $CO_2$/95% air in Dulbecco's Modified Eagle's Medium (DMEM) supplemented with 5 $\mu$g/mi insulin and 10% (v/v) newborn bovine serum (NBBS). The test medium was supplemented with $^3$H-thymidine and either AII ligand (50 nM) or AIV ligand (50 nM) or 10 ng/ml acidic or basic FGF (as a positive control). Negative controls were also included using ethidium bromide (1 mM). The cells were harvested at various times, and cellular lysates were prepared for scintillation counting by lysing and washing the cells on glass fiber filters.

Materials and Methods:

Reagents

AIV QVYIHPF; SEQ. ID. NO. 1), $AII_{(3-7)}$ (VYIHFP; SEQ. ID. NO. 27), and $AII_{(4-8)}$ (YIHPF (SEQ. ID. NO. 33)) were synthesized as described in Example 1, above. All reagents and other peptides were obtained from Sigma Chemical Co., with the exception of: Plummer's inhibitor (Calbiochem); bestatin (Peninsula Biochem); DUP 753 was a gift from Dr. Ron Smith of Dupont/Merck and CGP 42112A was a gift from Dr. Marc de Gasparo of Ciba-Geigy. Angiotensin fragments numbering was based on the sequence of AII (FIG. 1).

Cell Culture

Bovine coronary venular endothelial cells (CVEC) were isolated by a bead-perfusion technique and characterized as described previously (Schelling, M. E. et al. Am. J. Physiol. 254:H1211–H1217, 1988). Bovine aortic endothelial cells (BAEC) were a gift from Dr. Stephen Schwartz (University of Washington). Cells were grown in 100 mm tissue culture plates (Falcon, Becton Dickinson Co.) coated with 1.5% gelatin in PBS (per liter of distilled water: 8.12 g NaCl, 1.14 g $Na_2HPO_4$, 0.28 g $NaH_2PO_4$) in Dulbecco's modified Eagle's medium (DMEM; FLOW Labs) supplemented with 2 mM sodium pyruvate, 2 mM L-glutamine, 100 mg/ml heparin, 100 mg/ml Penicillin-G, 50 mg/ml Streptomycin, 44 mM NaHCO$_3$, and 10% fetal bovine serum (GIBCO). Cells were passaged 1:3 by tryptic digestion (0.05% trypsin, 0.025% EDTA in Ca$^{++}$/Mg$^{++}$-free PBS, pH7.4 at 37° C.). All data collected in this study was from cell lines passaged between passage 5 and passage 9.

Tissue preparation

Cells were grown to confluence in 100 mm culture dishes. Dishes were washed once in Ca$^{++}$/Mg$^{++}$-free PBS, pH7.4 at 37° C. followed by the addition of 2 ml of cold isotonic assay buffer (150 mM NaCl, 50 mM Tris, 1 mM PMSF, 10 $\mu$M bestatin, 50 $\mu$M Plummer's inhibitor, pH7.4 at 4° C.). Cells were then removed from the plates with a rubber policeman and homogenized in 5 ml assay buffer for approximately 10 sec (Polytron, Bruman Inst. Co.). Cell extracts were centrifuged at 40,000×g for 20 min at 4° C., the supernatant was discarded and the pellet was rehomogenized in assay buffer and centrifugation was repeated for a total of two high speed centrifugation steps. The final pellet was resuspended in assay buffer to a working concentration of approximately 5 mg/ml as determined by the method of Lowry (J. Biol. Chem. 193:265–267, 1951).

Iodination of AIV

AIV (and other peptides) were iodinated using an immobilized lactoperoxidase-glucose oxidase system (Enzymobeads, Biorad Laboratories) to a specific activity of 2176 Ci/mmole. $^{125}$I-AIV was separated from unlabeled peptide by HPLC (Beckman) using a reverse phase C$_{18}$ column (5 mm×250 mm; Adsorbosphere, Alltech, Associates).

Receptor binding assays

Binding assays were performed at 37° C. in a total volume of 250 ml (isotonic buffer, pH7.4 at 37° C.). Bound and free ligand were separated at the conclusion of each experiment by the addition of ice-cold PBS (pH7.4), and separation of bound from free was achieved by 4 vacuum filtration washes with 4 ml of this buffer (Schleicher and Schuell #32, Brandel Cell Harvester). Radioactivity retained by the filters was determined using a Tracor Analytic gamma counter, model #1185 having 68% counting efficiency. Nonspecific binding was ascertained in the presence of 1 mM unlabeled AIV.

Kinetic binding experiments (N=3) were performed at 37° C. over a time course of 240 min with 11 time points and duplicate samples. The apparent pseudo-first order association rate constant k$_{obs}$ was determined by the non-linear curve fitting program LIGAND. Dissociation experiments (N=4) were conducted at 37° C. by preincubating cell extracts for 120 min with 0.5 nM radiolabeled ligand followed by the addition of 1 mM unlabeled ligand (final conc.). Binding was determined for duplicate samples representing 10 time points over 180 min. The apparent dissociation rate constant, k$_{-1}$, was determined by LIGAND. The apparent association rate constant, k$_1$, was then calculated from the equation k$_1$=(k$_{obs}$−k$_{-1}$)[L], where [L] is the radioligand concentration, and the apparent kinetic equilibrium dissociation constant, K$_d$, was derived from the equation K$_d$=k$_{-1}$/k$_1$.

Saturation equilibrium binding and competition displacement studies (with CVEC, N=4 expts., 46 total data points; BAEC, N=3, 34 data points) were conducted over 120 min. of incubation in the presence of increasing concentrations of radioligand or competing ligands, respectively. Saturation data were analyzed by LIGAND for the determinations of maximum number of binding sites (B$_{max}$) and K$_d$.

For determining the linkage of G-proteins to the AT4 receptor, membrane preparations were first preincubated in GTP assay buffer (50 mM Tris, 150 mM NaCl, 5 mM MgCl$_2$1 mM EGTA, 1 mM PMSF, 50 $\mu$M Plummer's inhibitor, 10 $\mu$M bestatin, pH7.4) at 22° C. for 60 min in solutions of GTPγS calculated to produce a final concentration in the assay of 100 mM, 10 mM, 10 nM and 0 GTPγS. The rat vascular smooth muscle cell line WKY IV passage #17, was included as a positive control for G-protein linkage to AT1 receptors. All data are presented as the mean +/− SEM, standard error of the mean.

Endothelial cell growth and the effects of AIV ligand on EDRF production

Bovine aortic endothelial cells were grown at 37° C. in 35 mm culture plates under 5% CO$_2$ in air in Dulbecco's Modified Eagle's Medium (DMEM) supplemented with 5 $\mu$g/ml insulin and 10% (v/v) newborn bovine serum (NBBS). The medium was aspirated 10–12 hours after seeding and replaced with serum-free medium. The medium was again aspirated 10–12 hours later and replaced with either test or control medium. Control medium was DMEM with either 5 g/ml insulin and 2%, 5%, or 10% (v/v) NBBS as indicated. The test medium was supplemented with either AII or AIV ligand+the antagonist Sar$_1$,Ile$_8$-AII at various concentrations. The medium was changed every 48 h (i.e., with supportive DMEM medium for the remainder of the experiment).

For measurements to determine the effects of AIV in stimulating an increase in endothelial cell numbers, cells can be harvested on various days during the culture period by washing the plates with calcium free medium (CMF) two times for 5 min. followed by incubation in 0.1% trypsin in CMF for 5 min. The cells can then be washed free from the plate and aspirated by Pasteur pipet into 15 ml centrifuge tubes containing 3 ml DMEM with 20% (v/v) NBBS. The plates can be washed with an additional 1 ml DMEM 20% NBBS which was transferred to the appropriate centrifuge tube and spun at 300 x g for 10 min. Excess medium was aspirated and the pellet resuspended in a final volume of 1 ml of the control medium. Aliquots can then be counted using a hemocytometer and cell number expressed as cells/plate.

As an adjunct to the determination of cell numbers, thymidine incorporation was measured. For quantitation of DNA synthesis [methyl-$^3$H]thymidine (60 Ci/mmol, 10 mCi per plate) was added to cultures 12 h after addition of the AII or AIV. Twelve h later, medium was removed and 1 ml of a 1% aqueous solution of Triton X-100 was added. The cells were incubated with this solution for 5 min. and the entire contents of the plate transferred to 10 ml of absolute ethanol. This material was then filtered under vacuum through 2.4 cm glass fiber filters (GF/A, Whatman), and the filters were washed twice with 10 ml of absolute ethanol and assayed for radioactivity by scintillation counting.

EXAMPLE 6

Physiological Function of Angiotensin IV Receptor and Ligand

Angiotensins AI, AII, and AIII are reported to have a wide variety of effects on target issues, some of which are acute while others appear more long-term. AII reportedly has a cellular effect of increasing c-fos levels in cultured vascular smooth muscle cells (17), and c-fos is reported to be one common pathway for triggering cell growth. Considering the widespread distribution of AT4 receptors in many organs and tissues (EXAMPLES 1 and 2, above), it is likely that AIV has multiple functions, including long-term effects on cells by triggering increased expression of c-fos, i.e., activities previously mistakenly attributed to AII and AIII.

The following studies focus on the role that the AIV ligand-receptor system may play in three organs enriched in AT4 receptors: blood vessels, kidney, and adrenal glands. (Other organs such as brain or heart which also possess high levels of specifically localized AT4 receptors can be studied in a similar manner.)

Renal Blood Flow: The AIV Receptor and AII Receptor Have Physiologically Distinct and Opposing Activities:

Physiological studies, described below, investigated the involvement of AIV ligand in the regulation of renal blood flow. The rationale for initially choosing to examine the kidney was at least two-fold. First, the AT4 receptor is found in high concentrations in kidney and endothelial cells (Example 1 and 2, above). Second, vascular endothelial cells are reported to regulate vascular tone and to play a role in the control of renal blood flow.

Figure 4:
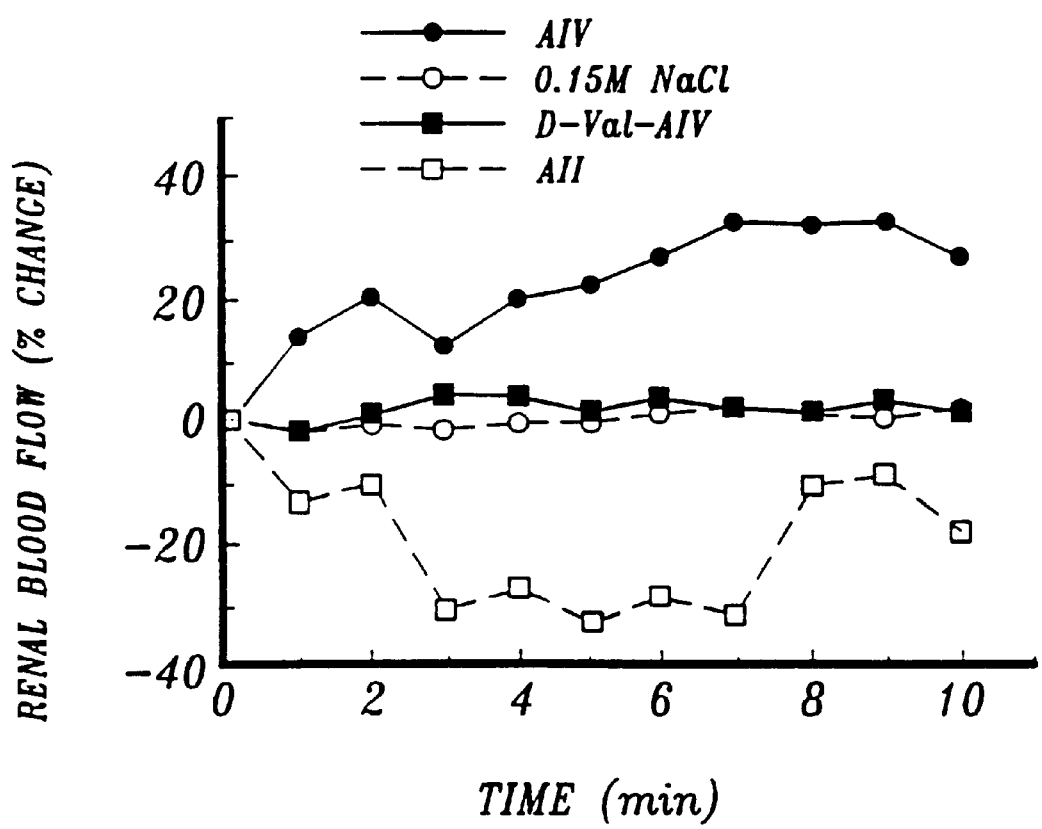
FIG. 4 graphically depicts the percentage change in renal blood flow after infusion of 100 pmol of AIV (n=13 experiments); 0.15 M saline (n=9); 100 pmol of D-Val$_1$-AIV (i.e., AIV with a D-valine residue in the 1 position); or 100 pmol of AII (n=8) into the renal artery at a rate of 25 ml/min, as described in Example 6.

Superficial blood flow in the rat kidney was assessed using laser doppler methods in anesthetized rats following direct infusion of a test substance into the renal artery. The results are presented in FIG. 4 which depicts the percentage change in cortical renal blood flow following infusion into the renal artery of 25 µl/min of a 0.15M NaCl solution containing 100 pmol/25 µl AIV (closed circles; number of experiments (n)=13); 0.15M saline (open circles; n=9); 100 pmol/25 µl of AIV lacking the N-terminal $Val_1$ residue (i.e., YIHPF (SEQ. ID. NO. 33); D-$Val_1$; closed squares; n=9); and 100 pmol/25µl of AII (open squares; n=8). The infusion of experimental compounds and saline had no effect on systemic arterial blood pressure (see results in Example 4). The infusion of AIV (closed circles) show that AIV ligand infused at 100 pmol/min. stimulates a profound and long-lasting increase in blood flow. In contrast, infusion of AII (also at 100 pmol/min.; open squares FIG. 4) produced a dramatic decrease in renal blood flow. The AIV analogue d-$Val_1$-AIV (i.e., lacking the N-terminal valine and lacking binding activity for the AT4 receptor, see Example 1, above) had no effect on renal blood flow (closed squares; FIG. 4).

The experimental protocols employed in these studies is detailed in the Materials and Methods, below.

Materials and Methods:

Experimental Protocol #1:

For comparison of AII, AIV, d-$Val_1$ AIV and saline infusion on renal blood flow, the respective agents were infused into the renal artery at 100 pmol/min. for 10 min. at 25 µl/min. Saline and the AIV analogue d-$Val_1$ AIV were included as controls, i.e., the number of experiments=8; average standard error of the mean (SE)=±3% change blood in flow. As expected, saline and d-$Val_1$ AIV had no effect on renal blood flow. Also, as expected, AII produced a dramatic decrease in flow followed by an autoregulatory return toward baseline. AIV produced an equally dramatic increase in flow that showed little autoregulation.

Consistent with the involvement of different receptors in the mediation of AII and AIV effects, the specific AII antagonist $Sar_1$, $Ile_8$-AII (1 nmol/min—10 min. pretreatment) completely blocked the AII effect while having no effect on AIV. The decrease in blood flow witnessed with AIV was dose dependent and was not accompanied by alterations in mean arterial pressure, suggesting that the effects of the AIV ligand-receptor system may be limited to selective vascular beds or that compensatory changes in cardiac output occurred during AIV infusion.

Experimental Protocol #2:

The AIV-induced increase in renal blood flow was not blocked preinfusing AII: $Sar_1$, $Ile_8$-AII was infused over the 10 min. immediately prior to infusion at 1 mnol/min., and a comparison was made with the change in blood flow that occurred when AIV ligand was infused without the AII preinfusion. In 8 experiments an average change in AIV-induced blood flow of <3% was recorded with the AII preinfusion, which was within the standard error of the experiments, i.e., SE=±3%. Thus, as predicted from the competition binding studies conducted above (Example 1), $Sar_1$, $Ile_8$-AII was unable to block the vasodilatory effect of AIV ligand. When tested in control experiments for the ability of AIV ligand to block AII-mediated decrease in blood flow (i.e., in the same type of preinfusion experiment, but using AIV preinfusion instead of AII). AIV ligand completely blocked the constrictive action of AII. Therefore, the results support the notion that AIV may antagonize certain of the actions of AII.

Effects of AIV-Ligand-Receptor Interactions on Renal Functions

Results presented above demonstrate that intravenous application of AIV ligand can dramatically increase renal blood flow and urine flow in a dose-dependent fashion. This effect appears to be mediated by the AT4 receptor and not by nonspecific, nonreceptor-dependent processes. Neither AII nor d-$Val_1$ AIV (a nonbinding AIV analogue) could reproduce the effects of AIV ligand, and the specific AII antagonist $Sar_1$, $Ile_8$-AII was unable to block the action of AIV ligand.

Another assessment of the AIV ligand-receptor effects on renal functions was provided by analyzing distribution of radio-labeled insulin and p-aminohippicuric acid; in combination with measurements of urine flow, urine osmolality, urine $Na^+$ and $K^+$, and hematocrit. The effects of AIV ligand, AII, and other AIV analogues were determined, i.e., a) on renal blood flow, b) glomerular filtration rate, c) osmolal clearance, d) filtration fraction, and e) tubular function. Dose-response curves for AIV ligand and AII ligand were constructed in the presence and absence of the AII antagonist $Sar_1$, $Ile_8$-AII. In addition, AIV analogues with special in vitro properties (e.g., AIV antagonists, AIV superagonists, or metabolically resistant analogues of AIV) were tested in a similar manner (above) to determine their effects on renal function. Studies were carried out as acute preparations in anesthetized rabbits and using jugular and urethral catheters.

EXAMPLE 7

Neurological Effects of the AIV-AIV Ligand-Receptor Interaction

Local Effects:

Given the presence of AT4 receptors in the brain (Example 2, above; FIGS. 6–10) and most likely in cognitive and motor memory and learning centers (i.e., hippocampus, frontal cortex, cerebellum, and thalamus), and in areas within the hindbrain cardiovascular nuclei involving the tractus solitarious, it is reasonable to suspect that at least in some tissues AIV ligand is produced locally in neural tissues, i.e., by synthesis of AI and conversion to AIV. Two scenarios of local production can be envisioned. In the first, AIV ligand is produced locally from precursors synthesized in the tissue. In the second, circulating AIV precursors (e.g., AI, AII or AIII) are converted locally to AIV ligand. Whether the first or second scenario is an operative mechanism in a particular tissue can be determined by introducing radiolabeled precursors (i.e., $^{125}I$-AI) into the bodily fluid bathing the tissue (e.g., plasma or CNS fluid), and by then collecting samples of the fluid at different times and assaying by reverse-phase HPLC to determine if the AIV precursor has been converted to AIV ligand in the fluid. If it has been converted, the second scenario is operative; if it has not been converted a second series of experiments is conducted. In the second series of experiments biosynthesis of AIV precursors is evaluated (i.e., with radiolabeled amino acids) and conversion of the precursor into AIV ligand is examined in pulse-chase type experiments. If biosynthetically radiolabeled AIV precursor chases into AIV ligand, then the first scenario is operative in the tissue.

Changes in the AIV-Ligand-Receptor System in Response to Neurological Effects:

A representative experimental protocols for showing changes in the AIV-ligand-receptor system in response to neurological and physiological effects is described in the Materials and Methods, below.

AT4 receptors in brain:

A comparison was made of the binding affinities (under equilibrium binding conditions) of AT4 receptors in different regions of guinea pig brain. The results of Scatchard analysis of binding data (conducted in the manner described above in Example 1) are summarized in Table 12, below.

TABLE 12

Binding of AIV in Regions of Brain[a]

| Brain Region | $K_d$ (nM) | $B_{max}$ (fmol/mg) |
|---|---|---|
| HSTA[b] | 0.11 +/− 0.051 | 168 +/− 52.7 |
| Hippocampus | 0.10 +/− 0.073 | 306 +/− 95.1 |
| Cerebellum | 0.21 +/− 0.237 | 232 +/− 93.2 |
| Brain stem | 0.09 +/− 0.054 | 197 +/− 63.9 |

[a]mean +/− SD; no. of experiments = 4

[b]HSTA = hypothalamus, thaiamus, septum, antereoventral third ventricular area.

The Hippocampal AIV Ligand-Receptor System:

Hippocampal AT4 receptors identified in tissues by receptor autoradiography in Example 2, above, were evaluated further by isolating hippocampal membranes (i.e., including hypothalamus, thalamus, septum, anteroventral third ventricular area, HSTA, above) and then solubilizing the receptor. (A similar approach may be employed with AT4 receptors in other tissues.) The results presented below show that the guinea pig hippocampal AT4 receptor binds AIV ligand with a high affinity ($K_d$=1.29±0.18 nM, mean ±SD, Hill Coeff.=0.993±0.015) and in a saturable manner ($B_{max}$= 449±62 fmol/mg protein). (It is noteworthy that the guinea pig hippocampal AT4 receptor binds AIV ligand with approximately the same binding affinity as the bovine adrenal AT4 receptor described in Example 1, above.) The density of the AT4 receptors in hippocampal cells and tissues was considerably higher than reported in brain for AII receptors (43, 44). In the present studies no AII receptors could be detected in Hippocampus by binding of $^{125}$I-Sar$_1$, Ile$_8$-AII (data not shown). The N-terminal structure of the binding AIV ligand is paramount in determining the binding affinity. The C-terminal requirements seem less stringent as evidenced by the binding affinity of AII$_{(3-7)}$(Kd=20.9±2.1 nM). Neither AII, AIII, Sar$_1$, Ile$_8$-AII, Dup 753 nor CGP42112A appear to bind indicating that this binding site is neither the AT1 nor AT2 sites described for AII/AIII. Autoradiographic analysis of Hippocampus binding confirms the inability of Sar$_1$, Ile$_8$-AII to competitively inhibit for $^{125}$I-AIV binding. Conversely AIV was unable to displace $^{125}$I-Sar$_1$, Ile$_8$-AII binding at this site. The finding of AT4 receptors in the Hippocampus suggests that AIV ligand-receptor interactions may mediate unique central angiotensin-dependent functions including memory enhancement and provide a link between the Hippocampus and memory.

Saturation isotherms and corresponding Rosenthal plot for $^{125}$I-AIV binding to AT4 receptors in guinea pig hippocampal membranes show specific binding of $^{125}$I-AIV ligand to isolated hippocampal membrane AT4 receptors purified from guinea pig brain. Nonspecific binding was defined in the presence of non-labeled competitor, i.e., 100 nM AIV. The experiment was carried out 5 times (n=5); $^{125}$I-AIV bound saturably and ligand analysis of the binding data indicated the presence of a single high affinity binding site ($K_d$=1.29±0.18 nM), $B_{max}$=449±62 femtomol/mg protein; Hill Coef=0.993±0.015; mean±SD.

Structural characteristics of AIV ligands that determine binding to the hippocampal AT4 receptor were determined in competition binding studies, i.e., similar to those described above in Example 1. The results of these competition studies are presented in Table 13.

TABLE 13

Competition of $^{125}$I-AIV Binding to Guinea Pig Hippocampus Membranes*

| Compound | $K_i$ (M) |
|---|---|
| AII | $<10^{-6}$ |
| AIII | $1.60 \pm .09 \times 10^{-7}$ |
| AIV | $4.28 \pm .51 \times 10^{-9}$ |
| AII$_{(3-7)}$ | $2.09 \pm .45 \times 10^{-8}$ |
| AII$_{(4-8)}$ | $>10^{-6}$ |
| AII$_{(3-5)}$ | $>10^{-6}$ |
| Sar$_1$,Ile$_8$-AII | $>10^{-6}$ |
| Dup753 | $>10^{-4}$ |
| CGP42112A | $>10^{-4}$ |

*n = 2, mean ± SD; 25 mg of total membrane protein was incubated with 0.6 nM $^{125}$I-AIV plus a variable concentration of unlabeled angiotensin as a competitor.

The results of these studies confirm those presented above in Example 1 with bovine adrenal AT4 receptors. The N-terminal of the AIV ligand (e.g., valine) is a major determinant of binding affinity. In agreement with the saturation isotherm data, AIV exhibited a high specificity for AIV (Table 13). N-terminal extended peptides including Sar$_1$, Ile$_8$-AII, AII, and AIII had significantly reduced affinities for the AT4 receptor while AII$_{(4-8)}$, which has the N-terminal L-Val removed, did not bind. (The low, but apparent ability of AIII to bind, may (as above) be due to conversion of AIII to AIV. The C-terminal specificity of the hippocampal AT4 receptor appears less. Removal of Phe from the C-terminal of AIV ligand diminishes, but does not eliminate binding (Table 13), while removal of Phe, Pro, and Ile eliminates binding. As seen in Table 7 neither Dup 753 nor CGP42112A competitively inhibited for the binding of $^{125}$I-AIV to the AT4 receptor. In addition, the peptides listed in Table 14, failed to bind to the HIV receptor in guinea pig brain as evidenced by their inability to significantly alter binding of AIV to receptors in this tissue.

TABLE 14

| Nonbinding Peptides ($K_d$ > $10^{-6}$ M)[a] |
|---|
| [pGlu,Cyt$_6$]-AVP$_{(4-9)}$ |
| pmp, O—Me—Tyr$_2$—Arg$_8$ |
| Arg$_8$-Vasopressin |
| Neurotensin |
| Oxytocin |
| Substances P |
| VIP |
| Neuropeptide Y |
| Atriopeptin |
| TRH |
| Tetradecapeptide |

TABLE 14-continued Nonbinding Peptides ($K_d > 10^{-6}$ M)[a]

Met—Enk
Leu—Enk
Gly—Phe—Ala
Bradykinin

[a]Peptides that fail to bind to guinea pig brain tissues as evidenced by $K_d > 10^{-6}$M.

This study demonstrates the existence of a unique angiotensin binding site in guinea pig Hippocampus which is specific for the N-terminal deleted AII hexapeptide, AIV. The location of this specific binding site in the Hippocampus supports the hypothesis that the AT4 receptor is the receptor that mediates angiotensin-dependent cognitive effects in the brain. It is clear from the autoradiographic sections shown in FIGS. 6–10, above, that the $^{125}$I-AT4 receptor is not restricted to the Hippocampus. The localization of $^{125}$I-AIV binding sites in other brain regions detailed in Table 15 presents an opportunity to expand the realm of angiotensin AIV-related actions.

TABLE 15

Autoradiographic Quantitation of AIV Receptors in Brain

| Region[a] | AIV Bound (fmol/gm) | AIV Displaced by AII (fmol/gm)[b] |
|---|---|---|
| Cerebellum | 6950.7 +/– 1675.7 | 6122.2 +/– 1496.3 |
| Hippocampus | 5059 +/– 1963.7 | 4501.8 +/– 223.0 |
| Piriform Cortex | 2771 +/– 954.7 | 2605.6 +/– 789.2 |
| Par 1/2 | 1644.3 +/– 343.5 | 1710.9 +/– 369.8 |
| Fr 1/2 | 1551.9 ± 604.2 | 1446.2 +/– 453.6 |
| Caudate Putamen | 1755.1 +/– 622.1 | 1663.3 +/– 654.1 |
| HDB | 2082.3 +/– 702.2 | 1985.6 +/– 621.1 |
| Thalamus | 2077.9 +/– 390.9 | 1904.4 +/– 646.5 |
| Inferior Colliculus | 2432.1 +/– 871.49 | 2235.0 +/– 663.8 |
| SOL** | 2446.3 +/– 881 | 2053.6 +/– 714.9 |
| ION** | 3323.1 +/– 136.3 | 3267.7 +/– 461.0 |

Figure 10A:
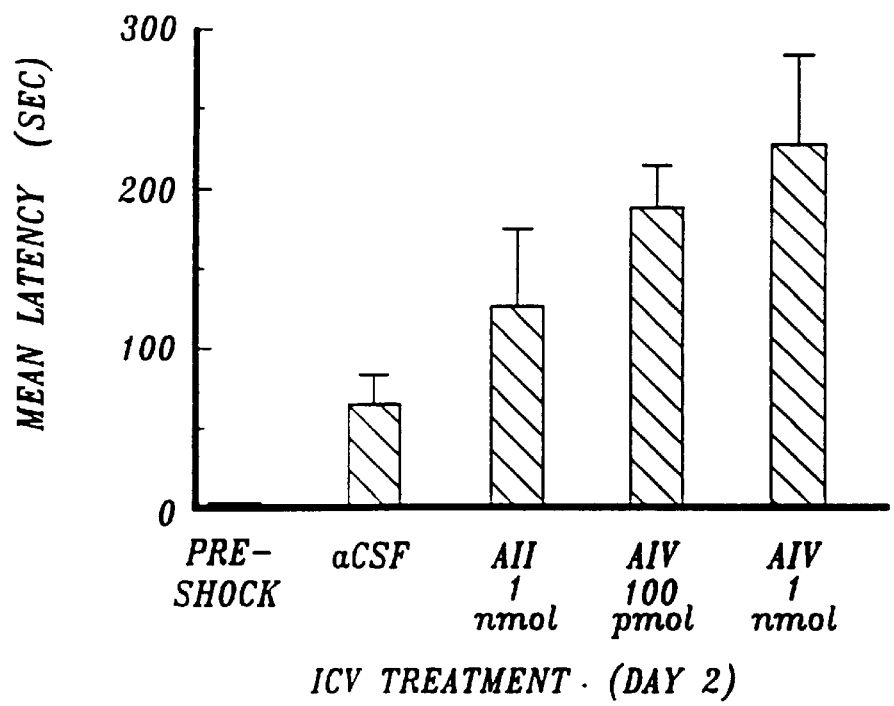
FIGS. 10A and 10B show enhancement of cognitive function, i.e., learning, in AIV intracerebroventricularly (icv) injected animals but not in AII-icv-injected animals. Testing of memory was conducted one day (FIG. 10A), or one, two and three days (FIG. 10B), after the animals learned a passive avoidance response; as described in Example 7.
Figure 10B:
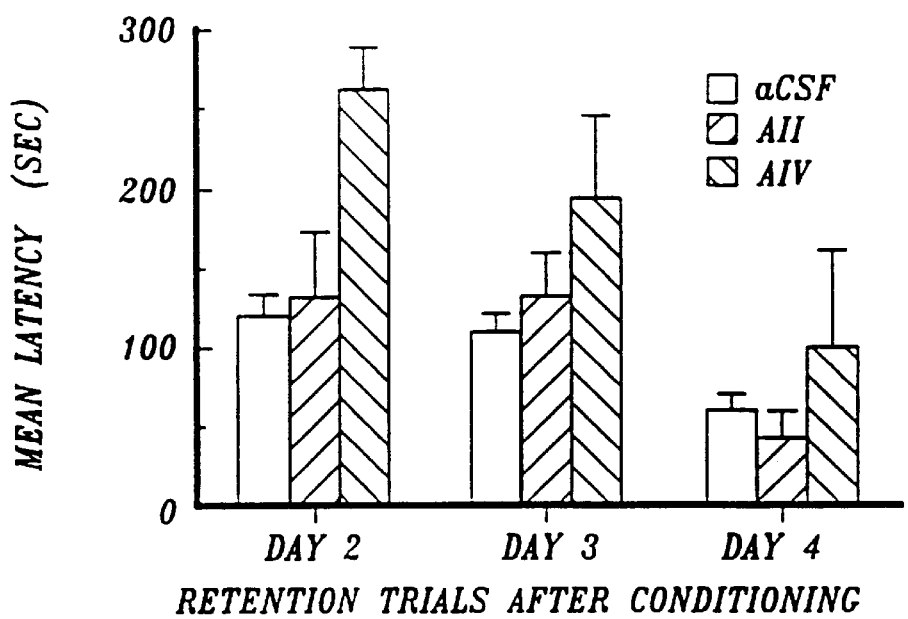

[a]n = 4 experiments;
*n = 3 experiments;
**n = 2 experiments;
[b]displacement of $^{125}$I-AIV by Sar,Ile-AII Cognitive effects of the AIV ligand-receptor system Learning: The results presented in FIG. 10B show the mean latency (sec+/–SEM) for independent groups of rats to re-enter the dark compartment on Days 2–4 following passive avoidance conditioning on Day 1. One minute prior to the shock trial on Day 1, members of each group received aCSF (2 ml), or 100 pmol in a total volume of 2 ml aCSF of AII or AIV. On subsequent test days each animal was placed back into the lighted compartment and latency to enter the dark compartment was measured. Members of the group that received AIV on Day 1 showed significantly elevated latency times to re-enter the dark side on Day 2, as compared with the mean results from animals in the aCSF and AII test groups. On day 1 artificial cerebrospinal fluid (aCSF), AII, or AIV was administered by intracerebroventribular (icv) injection into rat brains one minute prior to training. Training was conditioned (as described above) to avoid a dark compartment. On Days 2, 3, and 4 of the experiment the animals were tested for the latency of time before they would re-enter the dark compartment. Enhancement of memory retrieval was observed on days 2 and 3 after learning of the response (FIG. 10B). As can be seen from the results presented in FIG. 10B the effect diminished with time after the learning of the response.

Memory Retrieval: The effects of AIV ligand on learning and memory were tested in rats by measuring the passive avoidance response, i.e., the mean latency period (time in seconds) for which the animal avoided a dark compartment. Training was conditioned to avoid the dark compartment by administering a 0.25 mA foot shock over a period of 2 seconds with the door to a lighted compartment closed. On day 2 retrieval of the cognitive memory was tested 5 minutes after intracerebroventribular (icv) injection of AII or AIV. The results presented in FIG. 10A show that AIV has a positive effect on memory retrieval at 1 nmol and 100 pmol, i.e., the AIV test animals avoided the dark side for a longer latency period than AII-injected animals, or CSF-injected control animals.

Materials and Methods:

Hippocampal AT4 receptor studies:

Hippocampus was from 4-month old male guinea pigs following decapitation. The tissue was homogenized in 40 volumes of hypotonic buffer containing 50 mM Tris, pH7.4 and 5 mM EDTA, and spun at 1000 g for 10 min. The supernatant was removed and recentrifuged at 40,000 g for 30 min. The pellet was rehomogenized in hypotonic buffer and recentrifuged. The 40,000 g pellet was homogenized in isotonic buffer (50 mM Tris, pH7.4, 5mM EDTA, 150 mM NaCl, 20 mM bestatin, 50 mM Plummer's inhibitor, 100 mM PMSF, and 0.1% heat treated BSA) and recentrifuged a final time at 40,000 x g. The pellet was resuspended at a concentration of 2.5 mg protein/ml as determined by the Lowry protein assay. Binding assays, which totaled 250 ml, contained 10 ml $^{125}$I-AIV ligand (sp. act-2176 Ci/mmol), 10 ml tissue homogenate, 10 ml unlabeled peptide (if employed), and the remainder isotonic buffer. Incubations were carried out for 2 h at 37° C. Preliminary experiments demonstrated that incubation for 1 h at 37° C. was necessary for equilibrium to be reached and that binding was stable for at least 4 h. At that time less than 10% of the $^{125}$I-AIV was shown to be by HPLC analysis. Saturation isotherms were developed using 12 concentrations of $^{125}$I-AIV in duplicate and included total and nonspecific binding [+100 nM AIV]. Competition curves were developed using 500,000 cpm/tube (0.6 nM) of $^{125}$I-AIV and varying unlabeled peptide ($10^{-6}$M to $10^{-11}$M) in half-log dilutions (Dup 753), CGP42112A: $10^{-4}$M to $10^{-11}$M).

Autoradiographic studies:

Autoradiographic analysis of Hippocampus binding was carried out using 20 mM tissue sections mounted on slides. Slices were initially preincubated in isotonic buffer for 30 min at room temperature, then incubated in labeled ligand (0.6 nM) for 2 h, rinsed, dried, and exposed to X-ray film as previously described.

EXAMPLE 8

Isolation, Purification, and Characterization of the AIV Angiotensinase Enzyme

AIV Angiotensinase:

The results of studies conduced in Examples 1–3, above, with bovine adrenal cortex indicate that a high affinity peptidase (Km=3 nM) is present in these preparations that is capable of catalyzing hydrolysis of AII or AIII to AIV. Hydrolytic conversion of AII (or AIII) to AIV may result from the action of an AIV-specific aminoendopeptidase, capable of hydrolyzing an arginyl-valinyl peptide bond (between positions #2 and #3 in AII; FIG. 1) in an angiotensin termed herein AIV-angiotensinase. (Alternatively, the conversion of AIII to AIV may result from the action of nonspecific proteases but these enzymes may also cleave all angiotensins at sites other than the AII $R_2$-$V_3$, and are not termed herein AIV angiotensinase.). In either case, cleavage of the AII $Arg_2$-$Val_3$ peptide bond in AI, AII, or AIII generates AIV.

Considering the important evolutionary conservation of the AT4 receptor and AIV ligand, and their most significant physiological roles, it is most likely that certain tissues and cells possess a specific AIV angiotensinase enzyme(s), i.e., that cleaves AI, AII, and AIII in an efficient manner to permit regulatable formation of AIV. The AIV angiotensinase enzyme may be identified, isolated, and purified using the experimental approaches described below, in the Materials and Methods, in combination with the assays described in the Examples above (see Example 1). Data presented herein indicate that AII and AIII are excellent and specific inhibitors of $^{125}$I-AIV formation from $^{125}$I-AI.

Materials and Methods:

Experiment #1. Formation of AIV Ligand From AIV Precursors in Circulation.

$^{125}$I-labeled angiotensins ($10^7$ dpm)—AI, AII, or AIII, and tetradecapeptide can be injected into the carotid artery of a guinea pig and blood samples (50 µl) can be collected at 30-sec or 1-min. intervals from a second cannula in the femoral artery into 100 µl of 20% TCA for 10 min. Samples may be analyzed by reverse-phase HPLC utilizing methods that have been reported previously (47). The data are analyzed to determine the rate of formation of AIV ligand from potential AIV precursors.

Experiment #2: Formation of AIV from Precursors via Action of Adrenal Enzymes.

Guinea pig adrenals were excised and homogenized in a Krebs-Ringer buffer containing the full complement of ions (as above in Example 1). After a low speed spin at 500 g for 10 min. to remove whole cells and nuclei, the supernatant is centrifuged at 40,000 g for 30 min. The supernatant is recentrifuged at 100,000 g for 90 min. yielding both a soluble (100,000 g supernatant) and a microsomal (100,000 g pellet) fraction. The 40,000 x g pellet is rehomogenized and fractionated on a discontinuous sucrose fractionated gradient (0.4M–1.2M sucrose, in 0.2M steps). The membranes at the 0.8M to 1.M and 1M to 1.2M interfaces can be collected and combined, resuspended in a 10X excess of Krebs buffer. The membranes were then centrifuged at 40,000 x g for 30 min. After a final resuspension in Krebs buffer and centrifugation at 40,000 x g for 30 min., the final plasma membrane fraction is ready for the assay. Soluble, membrane, and microsomal fractions may be incubated at various protein concentrations and times at 37° C. with $10^6$ cpm of $^{125}$I-AI, AII, AIII, and tetradecapeptide. Conditions were chosen (as above) to yield less than 10% total precursor hydrolysis thus assuring that comparisons of conversion rates is carried out under initial rate conditions. The reaction is terminated with 20% TCA and the products were evaluated by reverse-phase HPLC. The assay may also be useful for identifying AIV angiotensinase enzyme in chromatographic and other SDS-PAGE fractions isolated from adrenal, plasma, neural, and other tissues and bodily fluids.

Experiment #3: Characterization of AIV-Specific Angiotensinase.

If guinea pig adrenal tissue (as expected) possesses an AIV angiotensinase, the specificity of the enzyme(s), its activity on various substrates, and metal ion requirements can be established by incubating preparations of the isolated enzyme with angiotensins (e.g., in the presence of inhibitors of nonspecific proteases), and followed by examination of the hydrolytic products on reverse-phase HPLC. The sequence of the hydrolytic products may be determined by automated amino acid sequencing. Incubation conditions with varying concentrations of the angiotensin substrate were used to develop data for double reciprocal plots thus allowing the affinity of enzyme(s) for the different angiotensins to be determined. Next, competition studies can be undertaken using various angiotensin analogues and unrelated peptides in order to establish the structural requirements of the AIV angiotensinase enzyme(s). Finally, the ability of numerous divalent ions to activate AIV angiotensinase can be monitored. These experiments can be carried out with AIV angiotensinase enzymes that have been EDTA-stripped and the EDTA/Me$^{++}$ removed by dialysis.

CITATIONS

1. M. J. Peach, *Physio. Rev.* 57,313 (1977)
2. C. I. Johnston, *Drugs* 39 (Suppl. 1), 21 (1990
3. J. R. Blair-West et al., *J. Clin. Endocrinol. Metab.* 32, 575 (1971) [see also #9, #10]
4. J. W. Harding and D. Felix, *Brain Res.* 410, 130 (1987)
5. D. Regoli, B. Riniker, and H. Brunner, *Biochem. Pharmacol.* 12, 637–646 (1963) [see also #2, #9, #10]
6. F. M. Bumpus, P. A. Khairallah, K. Arakawo, I. H. Page and R. R. Smeby, *Biochem. Biophys. Acta* 46, 38–44 (1961)
7. D. Regoli, W. K. Park and F. Rioux, *Pharmacol. Reviews* 26, 69–123 (1974) [see also #6, #10, #3]
8. Bennett, J. P. and Snyder, S. H., Angiotensin II binding to mammalian brain membranes, *J. Biol. Chem.* 251, 7423–7430, (1976). Colossman, H., Bankal A., and Catt K. J. Properties of angiotensin II receptors in the bovine and rat adrenal cortex. *J. Biol. Chem.* 249, 825–834 (1974)
9. Fitsimons, J. T. *J. Physiol Lond.* 214, 295–303 (1971).
10. Tonnaer, J. A., Weigant, V. M., Degong, W. and DeWeid, D., *Brain Res.* 236, 417–428 (1982).
11. Siemens, I. R., Swanson, O. N., Flaharty, S. J., and Harding, J. W., *J. Neurochem* 57, 690–700 (1991)
12. T. Kono, F. Ikeda, F. Oseko, Y. Ohmori, R. Nakano, H. Muranaka, A. Taniguchi, H. Imura, M. C. Khosla and F. M. Bumpus, *Acta endocr.* 99, 577–584 (1982).
13. Kono, T. et al., *Acta Endocr.* 109, 249–253 (1985)
14. R. L. Haberl, P. J. Decker and K. M. Ejnhäupl, *Circ. Res.* 68, 1621–1627 (1991)
15. J. J. Brazko, J. Wlasienko, W. Koziolkiewicz, A. Janecka and K. Wisniewski, *Brain Res.* 542, 49–54 (1991)
16. J. J. Brazko, G. Kupryszewski, B. Witczuk and K. Wisniewski, *Neurosci* 27, 777–783 (1988)
17. J. J. Brazko, K. Wisniewski, G. Kupryszewski and B. Witczuk, *Behav. Brain Res.* 25, 195–203 (1987)
18. P. F. Semple, A. S. Boyd, P. M. Dawes and J. J. Morton, *Circ. Res.* 39, 671–678 (1976).
19. B. Blumberg, A. L., et al., (1977) *Circ. Res* 41, 154–158 (1977).
20. J. P. Bennett and S. H. Snyder, *Eur. J. Pharmacol.* 67, 11 (1980).
21. Kumar, S. Keegen, A., Erroi, A., West, D. Kumar P., and Gaffney, J., *Prog. App. Microcirc.* 4, 54–75 (1984).
22. Fernandez, L. A., Twickler, J. and Mead, A. *Lab. Clin Med* 105, 141–145 (1985).
23. Patel, J. W. et al., *Amer. J. Physiol.* 256, 987–993 (1989).
24. King, S. J., Beck, J. C., Harding, J. W., and Hosick, H. L., *Abstract Amer. Soc. Cell Biol.* (1986)
25. Baker, K. M. and Aceto, J. F., *Am J Physiol.* 259, H610–H618 (1990).
26. Baker, K. M., Chernim, M. I., Wixson, S. K., and Aceto, J. F., *Am. J Physiol.*, 259, H324–H332 (1990).
27. Yamaguchi, T., Naito, Z., Stoner, G. D., Franco-Saanz, R. and Mulrow, P. J., *Hypertension* 16, 635–641 (1990).
28. Carpenter, G., King, L. Jr., and Cohen, S., *J. Biol. Chem.* 254, 4884–4891 (1979).

29. Munson, P. J., and Rodbard, D., *Anal. Biochem.* 107, 220–239 (1980).
30. Freissmuth, M., Casey, P. J., and Gilman, A. G. *FASEB J.* 3, 2125–2131 (1989).
31. Brown, A. M. and Bimbauer, L., *Am. J Physiol.* 254, H401–H410 (1988).
32. Schulz, S., Chinkers, M., and Garbers, D. L., *FASEB J.* 3, 2026–2035 (1989).
33. Nishibe, S. Wahl, M. I., Hernandez-Sotomayor, S.M.T., Tonks, N. K., Rhee, S. G., and Carpenter, G., *Science* 250, 1253–1256 (1990).
34. Pandiella, A., Bequinot, L., Vincentini, L. M., and Meldotesi, J., *TIPS* 10, 411–414 (1989).
35. Cohen, S., Carpenter, G., and King, L. Jr.,*J. Biol. Chem.*, 255, 4834–4842 (1980).
36. Pang, T. P., Wang, J.K.T., Valtork, F., Bentenati, F., and Coreengard, P., *PNAS* 85, 762–766 (1988)
37. Dean, N. M. and Moyer, J. D., *J. Biol. Chem.* 250, 493–500 (1988).
38. Wright, J. W., Jensen, L. L., Roberts, K. A., Sardinia, M. F., and Harding, J. W.,*Am. J Physiol.* 257, R1551–R1557 (1989).
39. Gill, G. N., Ill, C. R., and Simonian, M. H., *Proc. Nat. Acad. Sci.* 74, 5569–5573 (1977).
40. Livett, B. G., Mitchellhill, K. I., and Dean, D. M., "In vitro methods for studying secretion", 171–176 (1987b).
41. Livett, B. G., Marley, P. D., Mitchellhill, K. I., Wan, D.C.C., and White, T. D., "In vitro methods for studying secretion", 177–204 (1987a).
42. Aceto, J. F. and Baker, K. H., *Am. J Physiol.* 258, H806–H813 (1990).
43. Mendelsohn, F.A.D. et al., *Proc. Natl. Acad. Sci. USA* 81, 1575–1579 (1984).
44. Speth, R. C. et al. In: J. W. Harding et al. (Eds) "Angiotensin and Blood Pressure Regulation", Acad. Press, S. D., CA. p. 1–3 (1988).
45. Paul, A. K. Marada, R. B., Jaiswal, R. K., and Sharma, R. K., *Science* 235, 1224–1226 (1987).
46. Glaring et al. 1989
47. Abhold, R. H. and Harding, J. W., *J. Pharmacol Enp. Ther.* 245, 171–177 (1988).

What is claimed is:

1. A method for screening for an agent that is an agonist or an antagonist of the interaction between an angiotensin IV ligand and an angiotensin IV receptor, comprising:

(a) adding an angiotensin IV ligand to a first sample comprising an angiotensin IV receptor to form a control mixture, said angotensin IV ligand being a compound of the formula:

$$R_1R_2R_3X,$$

wherein $R_1$ is a substituted or unsubstituted amino acid residue having neutral or positively charged aliphatic side chain $Z_1$, said amino acid being selected from among V, I, L, A, G, F, P, M, K, norvaline, norleucine, and ornithine, $R_2$ is a substituted or unsubstituted neutral polar amino acid residue selected from among Y, W, N, O, F or C, $R_3$ is a substituted or substituted neutral polar amino acid residue selected from among G, A, V, I, L, F, P, or M, and X is nothing, $R_1$, $R_4$–$R_5$, or $R_1$–$R_5$–$R_6$, wherein $R_1$ is a substituted or unsubstituted basic amino acid residue selected from the group consisting of K, R and H, $R_5$ is a substituted or unsubstituted neutral polar amino acid residue selected from the group consisting of G, A, V, I, L, F, P, and M, and $R_6$ is a substituted or unsubstituted neutral polar amino acid residue selected from the group consisting of G, A, V, I, L, F, P, M, and polvamio acid residues containing one or amino acid residues which do not prevent binding of the AIV ligand with the AT4 receptor;

with the proviso that $R_1$ can not be V when $R_2$ is Y, $R_3$ is I, $R_4$ is H, $R_5$ is P and $R_6$ is F;

(b) adding the angiotensin IV ligand and a putative agent to a second sample comprising an angiotensin IV receptor to form a test mixture;

(c) determining the rate, amount or affinity of binding of the angiotensin IV ligand to the angiotensin IV receptors in the control mixture and the test mixture; and (d) determining that the putative agent is an angiotensin IV agonist if the rate, amount or affinity of binding of the angiotensin IV ligand to the angiotensin IV receptor is greater in the test mixture than in the control mixture, or is an angiotensin IV antagonist if the rate, amount or affinity of binding of the angiotensin IV ligand to the angiotensin IV receptor is less in the test mixture than in the control mixture.

2. The method of claim 1, wherein the first sample comprises an isolated cell membrane comprising the Angistensia IV receptor.

3. The method of claim 2, wherein the isolated cell membrane is a mammalian cell membrane selected from the group consisting of an adrenal cortical membrane, an adrenal medullary cell membrane, a brain cell membrane, a vascular smooth muscle cell membrane, a vascular endothelial cell membrane, and a cardiomyocyte membrane.

4. The method of claim 3, wherein the first sample comprises a brain cell membrane and the brain cell membrane comprises homogenized mammalian hippocampal tissue.

5. The method of claim 2, wherein the cell membrane is heated to a temperature and for a time sufficient to inactivate peptidase activity before adding the Angiotensin IV ligand.

6. The method of claim 5, wherein the heating is conducted in the presence of $MgCl_2$.

7. A method of identifying the presence of an inhibitor of angiotensin IV ligand binding to an angiotensin IV receptor in a biological fluid, comprising the steps of:

(a) adding an amount of an angiotensin IV ligand effective to produce measurable receptor binding to a first cell culture comprising an angiotensin IV receptor to form a control mixture, said angiotensin IV ligand being a compound of the formula:

$$R_1R_2R_3X,$$

wherein $R_1$ is a substituted or unsubstituted amino acid residue having a neutral or positively charged aliphatic side chain $Z_1$, said amino acid being selected from among V, I, L, A, G, F, P, M, K, norvaline, norleucine, and ornithine, $R_2$ is a substituted or unsubstituted neutral nonpolar amino acid residue selected from among Y, W, N, O, F or C, $R_3$ is a substituted or unsubstituted neural polar amino acid residue selected from among G, A, V, I, L, F, P, or M, and X is nothing, $R_1$, $R_1$–$R_5$, or $R_4$–$R_5$–$R_6$, wherein $R_1$ is a substituted or unsubstituted basic amino acid residue selected from the group consisting of K, R and H, $R_5$ is a substituted or unsubstituted neutral polar amino acid residue selected from the group consisting of G, A, V, I, L, F, P, and M, and $R_6$ is a substituted or unsubstituted neutral polar amino acid residue selected from the group consist of G, A, V, I, L, F, P, M, and polvamino acid residues containing one or amino acid residues which do not prevent binding of the AIV ligand with the AT4 receptor;

with the proviso that $R_1$ can not be V when $R_2$ is Y, $R_3$ is I, $R_1$ is H, $R_5$ is P and $R_6$ is F;

(b) adding said angiotensin IV ligand and a sample of said biological fluid or fraction thereof to a second cell culture comprising angiotensin IV receptor;

(c) measuring the level of binding of said angiotensin IV ligand to the cells in the first and second cultures; and (d) determining the presence of an inhibitor of angiotensin IV ligand to the angioterisin IV receptor when the level of binding in the second culture is significantly lower than in the first culture.

* * * * *

UNITED STATES PATENT AND TRADEMARK OFFICE
CERTIFICATE OF CORRECTION

PATENT NO. : 6,022,696
APPLICATION NO. : 09/054308
DATED : February 8, 2000
INVENTOR(S) : J.W. Harding et al.

Page 1 of 6

It is certified that error appears in the above-identified patent and that said Letters Patent is hereby corrected as shown below:

| COLUMN | LINE | ERROR |
|---|---|---|
| 1 | 32 | "renin or" should read --renin on-- |
| 3 | 30 | "and" should read --as-- |
| 3 | 37 | "Ile$_3$ should read --Ile$_8$-- |
| 4 | 9 | "sa" should read --as-- |
| 4 | 13-14 | "NroLeuYIHPF" should read --NorLeuYIHPF-- |
| 4 | 36 | "$^{125}$I-AIV" should read --$^{125}$I-AIV-- |
| 5 | 9 | ""Des-Asp" should read --"des-Asp-- |
| 6 | 16 | "improves or" should read --improves on-- |
| 8 | 9-10 | "metabolite (s)" should not break |
| 8 | 17-18 | "carbox-Ypeptidase" should break as follows: --carboxy-peptidase-- |
| 8 | 53 | "AII$_{3-8)}$." should read --AII$_{(3-8)}$.-- |
| 9 (Table 1, | lines 15-16) | "Hippocampus g" should read --Hippocampus$^g$-- |
| 9 (Table 1, | line 17) | "HSTAh" should read --HSTA$^h$-- |
| 10 (Table 1, | 18 footnote g) | after "and" delete ";" |

UNITED STATES PATENT AND TRADEMARK OFFICE
CERTIFICATE OF CORRECTION

PATENT NO. : 6,022,696
APPLICATION NO. : 09/054308
DATED : February 8, 2000
INVENTOR(S) : J.W. Harding et al.

It is certified that error appears in the above-identified patent and that said Letters Patent is hereby corrected as shown below:

| COLUMN | LINE | ERROR |
|---|---|---|
| 15 | 14 | "peptide or" should read --peptide on-- |
| 22 | 7 | "later" should read --latter-- |
| 23 | 47 | "conditions as" should read --conditions was-- |
| 24 (Table 7, | 60 heading) | "Solubiiized" should read --Solubilized-- |
| 25 (Table 7, | 3 heading) | "Solubiiized' should read --Solubilized-- |
| 25 (Table 7, | 11 line 10) | "O,47" should read --0.47-- |
| 26 | 31 | "34." should read --3-4.-- |
| 26 | 32 | "Val(I)Val(3)" should read --Val(1)Val(3)-- |
| 27 | 50 | "125I-AIV" should read --$^{125}$1-AIV-- |
| 27 | 51 | "125I-AII or 125I-AIV" should read --$^{125}$I-AII or $^{125}$I-AIV-- |
| 29 | 1-7 | the table heading should not repeat on this page |
| 29 | 8 | "125I-Sar$_1$," should read --$^{125}$I-Sar$_1$,"-- |
| 29 | 11 | "1 .8" should read --1.8-- |
| 30 | 26 | "Autobiography" should read --Autoradiography-- |
| 31 | 5 | "$^{125}$-AIV" should read --$^{125}$I-AIV-- |
| 31 | 7-8 | "$^{125I}$I-Sar$_1$," should read --$^{125}$I-Sar$_1$,-- |

UNITED STATES PATENT AND TRADEMARK OFFICE
CERTIFICATE OF CORRECTION

PATENT NO. : 6,022,696
APPLICATION NO. : 09/054308
DATED : February 8, 2000
INVENTOR(S) : J.W. Harding et al.

It is certified that error appears in the above-identified patent and that said Letters Patent is hereby corrected as shown below:

| COLUMN | LINE | ERROR |
|---|---|---|
| 31 | 30 | "AH1" should read --AII-- |
| 31 | 51 | "AI1" should read --AII-- |
| 31 | 64 | "AI1" should read --AII-- |
| 32 | 52 | "AI 1" should read --AII-- |
| 32 | 61 | before "(31)" insert -- -- |
| 33 | 29 | "Ile$_8$AII" should read --Ile$_8$-AII-- |
| 33 | 48 | "Ile$_8$AII" should read --Ile$_8$-AII-- |
| 36 | 20 | "AI1" should read --AII-- |
| 37 | 32 | "3dimensional" should read --3-dimensional-- |
| 38 | 60 | "MIV" should read --AIV-- |
| 38 | 61 | "MIV" should read --AIV-- |
| 39 (Table 10, last line of 4 col. "Lys") | 13 | "NH$_3^{\ominus}$" should read --NH$_3^{\oplus}$-- |
| 39 (Table 10, last line of col. "Orn") | 13 | "NH$_3^{\oplus}$" should read --NH$_3^{\oplus}$-- |
| 40 | 11 | "COO–" should read --COO$^-$-- |
| 40 | 23 | "1XI" should read --1X1-- |
| 42 | 4 | "Both AIV . . . " should begin a new paragraph |
| 42 | 53 | "Nlel-AIV$_{(1-3)}$" should read --Nle$_1$-AIV$_{(1-3)}$-- |
| 43 | 26 | "mnM" should read --mM-- |

UNITED STATES PATENT AND TRADEMARK OFFICE
CERTIFICATE OF CORRECTION

PATENT NO. : 6,022,696
APPLICATION NO. : 09/054308
DATED : February 8, 2000
INVENTOR(S) : J.W. Harding et al.

It is certified that error appears in the above-identified patent and that said Letters Patent is hereby corrected as shown below:

| COLUMN | LINE | ERROR |
|---|---|---|
| 44 | 14-15 | "endot-<br>helial" should break as follows:<br><br>--endo-<br>thelial-- |
| 44 | 63 | "125I-AIV" should read --$^{125}$I-AIV-- |
| 45 | 14 | "Kd" should read --$K_d$-- |
| 45 | 26-27 | "endot-<br>helial" should break as follows:<br><br>--endo-<br>thelial-- |
| 47 | 44-45 | "intrac-<br>erebroventricularly" should break as follows:<br><br>--"intra-<br>cerebroventricularly-- |
| 48 | 34 | "mi" should read --ml-- |
| 48 | 45 | "QVYIHPF;" should read --(VYIHPF;-- |
| 49 | 14 | "Bruman" should read --Brinkman-- |
| 49 | 53 | "$k_1=(k_{obs}-k_{-1})[L]$," should read<br>--$k_1=(k_{obs}-k_{-1})/[L]$,-- |
| 50 | 20 | "ligand+the" should read --ligand±the-- |
| 51 | 5 | "AII" should read --AII-- |
| 51 | 23 | "N-terninal should read --N-terminal-- |
| 51 | 64 | "1 mnol" should read --1 nmol-- |

UNITED STATES PATENT AND TRADEMARK OFFICE
CERTIFICATE OF CORRECTION

PATENT NO. : 6,022,696
APPLICATION NO. : 09/054308
DATED : February 8, 2000
INVENTOR(S) : J.W. Harding et al.

It is certified that error appears in the above-identified patent and that said Letters Patent is hereby corrected as shown below:

| COLUMN | LINE | ERROR |
|---|---|---|
| 53 | 29 | "thaiamus" should read --thalamus-- |
| 53 | 53 | "AII$_{(3-7)}$" should read --AII$_{(3-7)}$-- |
| 54 | 31 | There should be no paragraph break following "nM" |
| 55 | 56 | "All," should read --AII,-- |
| 87 (Claim 1, line 6) | 7 | "angotensin" should read --angiotensin-- |
| 87 (Claim 1, line 13) | 16 | "omithine," should read --ornithine,-- |
| 87 (Claim 1, line 14) | 17 | "polar" should read --nonpolar-- |
| 87 (Claim 1, line 15) | 18 | "O," should read --Q-- |
| 87 (Claim 1, line 16) | 19 | "substituted" (second instance) should read --unsubstituted-- |
| 87 (Claim 1, line 19) | 22 | "$R_1$, $R_4$-$R_5$, or $R_1$-$R_5$-$R_6$, wherein $R_1$" should read --$R_4$, $R_4$-$R_5$, or $R_4$-$R_5$-$R_6$, wherein $R_4$-- |
| 87 (Claim 1, line 27) | 30 | "polvamino" should read --polyamino-- |
| 87 (Claim 2, lines 2-3) | 51-52 | "Angistensia" should read --angiotensin-- |
| 87 (Claim 3, line 5-6) | 57-58 | "endot-helial" should break as follows: --endo-thelial-- |

UNITED STATES PATENT AND TRADEMARK OFFICE
CERTIFICATE OF CORRECTION

PATENT NO. : 6,022,696
APPLICATION NO. : 09/054308
DATED : February 8, 2000
INVENTOR(S) : J.W. Harding et al.

It is certified that error appears in the above-identified patent and that said Letters Patent is hereby corrected as shown below:

| COLUMN | LINE | ERROR |
|---|---|---|
| 88 (Claim 5, | 7 line 3) | "Angiotensin" should read --angiotensin-- |
| 88 (Claim 7, | 26 line 14) | "omithine," should read --ornithine,-- |
| 88 (Claim 7, | 28 line 16) | "O," should read --Q-- |
| 88 (Claim 7, | 33 line 21) | "$R_1$, $R_1$-$R_5$, or $R_4$-$R_5$-$R_6$, wherein $R_1$" should read --$R_4$, $R_4$-$R_5$, or $R_4$-$R_5$-$R_6$, wherein $R_4$-- |
| 88 (Claim 7, | 41 line 29) | "polvamino" should read --polyamino-- |
| 88 (Claim 7, | 45 line 33) | "$R_1$" should read --$R_4$-- |
| 88 (Claim 7, | 54 line 40) | "angioterisin" should read --angiotensin-- |

Signed and Sealed this

Twenty-first Day of November, 2006

JON W. DUDAS
*Director of the United States Patent and Trademark Office*

SEQUENCE LISTING (1) GENERAL INFORMATION:

(iii) NUMBER OF SEQUENCES: 38

(2) INFORMATION FOR SEQ ID NO:1:

(i) SEQUENCE CHARACTERISTICS:
      (A) LENGTH: 6 amino acids
      (B) TYPE: amino acid
      (C) STRANDEDNESS: single
      (D) TOPOLOGY: linear (ii) MOLECULE TYPE: peptide
      (A) DESCRIPTION: Angiotensin IV (iii) HYPOTHETICAL: NO (iv) ANTI-SENSE: NO (v) FRAGMENT TYPE: N-terminal (vi) ORIGINAL SOURCE:
      (A) ORGANISM: Bos taurus (xi) SEQUENCE DESCRIPTION: SEQ ID NO:1:

Val Tyr Ile His Pro Phe
1             5

(2) INFORMATION FOR SEQ ID NO:2:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide
      (A) DESCRIPTION: Angiotensin II (iii) HYPOTHETICAL: NO (iv) ANTI-SENSE: NO (v) FRAGMENT TYPE: N-terminal (vi) ORIGINAL SOURCE:

(A) ORGANISM: Bos taurus (ix) FEATURE:
            (A) NAME/KEY: Modified-site
            (B) LOCATION: Multiple
            (D) OTHER INFORMATION:
                /note= Includes variants from which deletions have been
                made at the C-terminus by 1, 2, 3, 4, or 5 residues.

(xi) SEQUENCE DESCRIPTION: SEQ ID NO:2:

Asp Arg Val Tyr Ile His Pro Phe
1               5

(2) INFORMATION FOR SEQ ID NO:3:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide
            (A) DESCRIPTION: Angiotensin III (iii) HYPOTHETICAL: NO (iv) ANTI-SENSE: NO (v) FRAGMENT TYPE: N-terminal (vi) ORIGINAL SOURCE:
            (A) ORGANISM: Bos taurus (xi) SEQUENCE DESCRIPTION: SEQ ID NO:3:

Arg Val Tyr Ile His Pro Phe
1               5

(2) INFORMATION FOR SEQ ID NO:4:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
            (A) ORGANISM: Bos taurus (ix) FEATURE:
            (A) NAME/KEY: Modified-site
            (B) LOCATION: N-terminal amino acid
            (D) OTHER INFORMATION:
                /note= Xaa is Nle
                /note= Includes variants from which deletions have been
                made at the C-terminus of 1 or of 2 residues.

(xi) SEQUENCE DESCRIPTION: SEQ ID NO:4:

Xaa Tyr Ile His Pro Phe
1               5

(2) INFORMATION FOR SEQ ID NO:5:

(i) SEQUENCE CHARACTERISTICS:
            (A) LENGTH: 14 amino acids
            (B) TYPE: amino acid
            (C) STRANDEDNESS: single

```
          (D) TOPOLOGY: linear (ii) MOLECULE TYPE: peptide
          (A) DESCRIPTION: Angiotensin (iii) HYPOTHETICAL: NO (iv) ANTI-SENSE: NO (v) FRAGMENT TYPE: N-terminal (vi) ORIGINAL SOURCE:
          (A) ORGANISM: Bos taurus (xi) SEQUENCE DESCRIPTION: SEQ ID NO:5:

Asp Arg Val Tyr Ile His Pro Phe His Leu Val Ile His Ser
1               5                   10

(2) INFORMATION FOR SEQ ID NO:6:

(i) SEQUENCE CHARACTERISTICS:
          (A) LENGTH: 10 amino acids
          (B) TYPE: amino acid
          (C) STRANDEDNESS: single
          (D) TOPOLOGY: linear (ii) MOLECULE TYPE: peptide
          (A) DESCRIPTION: Angiotensin I (iii) HYPOTHETICAL: NO (iv) ANTI-SENSE: NO (v) FRAGMENT TYPE: N-terminal (vi) ORIGINAL SOURCE:
          (A) ORGANISM: Bos taurus (ix) FEATURE: Includes variants in which deletions have been made
                  at the C-terminus by 1, 2, 3, 4, or 5 residues.

(xi) SEQUENCE DESCRIPTION: SEQ ID NO:6:

Asp Arg Val Tyr Ile His Pro Phe His Leu
1               5                   10

(2) INFORMATION FOR SEQ ID NO:7:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: peptide
          (A) DESCRIPTION: [des-Asp] Angiotensin I (iii) HYPOTHETICAL: NO (iv) ANTI-SENSE: NO (v) FRAGMENT TYPE: N-terminal (vi) ORIGINAL SOURCE:
          (A) ORGANISM: Bos taurus (xi) SEQUENCE DESCRIPTION: SEQ ID NO:7:

Arg Val Tyr Ile His Pro Phe His Leu
1               5

(2) INFORMATION FOR SEQ ID NO:8:

(i) SEQUENCE CHARACTERISTICS:
          (A) LENGTH: 7 amino acids
          (B) TYPE: amino acid
```

```
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
            (A) ORGANISM: Bos taurus (ix) FEATURE:
            (A) NAME/KEY: Modified-site
            (B) LOCATION: Amino acid 7
            (D) OTHER INFORMATION:
                 /note= Xaa is any non-interfering amino acid, as defined
                 on page 8.

(xi) SEQUENCE DESCRIPTION: SEQ ID NO:8:

Val Tyr Ile His Pro Phe Xaa
1               5

(2) INFORMATION FOR SEQ ID NO:9:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
            (A) ORGANISM: Bos taurus (ix) FEATURE:
            (A) NAME/KEY: Modified-sites
            (B) LOCATION: Amino acids 1,7
            (D) OTHER INFORMATION:
                 /note= Xaa/1 is Nva
                 /note= Xaa/7 is any non-interfering amino acid (xi) SEQUENCE DESCRIPTION: SEQ ID NO:9:

Xaa Tyr Ile His Pro Phe Xaa
1               5

(2) INFORMATION FOR SEQ ID NO:10:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
            (A) ORGANISM: Bos taurus (ix) FEATURE:
            (A) NAME/KEY: Modified-sites
```

```
            (B) LOCATION: Amino acids 1 and 7
            (D) OTHER INFORMATION:
                  /note= Xaa/1 is Orn
                  /note= Xaa/7 is any non-interfering amino acid (xi) SEQUENCE DESCRIPTION: SEQ ID NO:10:

Xaa Tyr Ile His Pro Phe Xaa
1               5

(2) INFORMATION FOR SEQ ID NO:11:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
            (A) ORGANISM: Bos taurus (ix) FEATURE:
            (A) NAME/KEY: Modified-site
            (B) LOCATION: Amino acid 7.
            (D) OTHER INFORMATION:
                  /note= Xaa is one or more non-interfering amino acids.

(xi) SEQUENCE DESCRIPTION: SEQ ID NO:11:

Lys Tyr Ile His Pro Phe Xaa
1               5

(2) INFORMATION FOR SEQ ID NO:12:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
            (A) ORGANISM: Bos taurus (ix) FEATURE:
            (A) NAME/KEY: Modified-sites
            (B) LOCATION: Amino acids 1 and 7
            (D) OTHER INFORMATION:
                  /note= Xaa/1 is Nle
                  /note= Xaa/7 is one or more non-interfering amino acids.

(xi) SEQUENCE DESCRIPTION: SEQ ID NO:12:

Xaa Tyr Ile His Pro Phe Xaa
1               5

(2) INFORMATION FOR SEQ ID NO:13:

(i) SEQUENCE CHARACTERISTICS:
            (A) LENGTH: 9 amino acids
            (B) TYPE: amino acid
            (C) STRANDEDNESS: single
```

```
            (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
            (A) ORGANISM: Bos taurus (ix) FEATURE:
            (A) NAME/KEY: Modified-site
            (B) LOCATION: C-terminal amino acid.
            (D) OTHER INFORMATION:
                /note= Xaa is one or more non-interfering amino acids.

(xi) SEQUENCE DESCRIPTION: SEQ ID NO:13:

Asp Arg Val Tyr Ile His Pro Phe Xaa
1               5

(2) INFORMATION FOR SEQ ID NO:14:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
            (A) ORGANISM: Bos taurus (ix) FEATURE:
            (D) OTHER INFORMATION:
                /note= Includes variants from which deletions have been
                made at the C-terminus of 1, 2, or 3 residues.

(xi) SEQUENCE DESCRIPTION: SEQ ID NO:14:

Lys Tyr Ile His Pro Phe
1               5

(2) INFORMATION FOR SEQ ID NO:15:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
            (A) ORGANISM: Bos taurus (ix) FEATURE:
            (A) NAME/KEY: Modified-site
            (B) LOCATION: Amino acid 1
            (D) OTHER INFORMATION:
                /note= Xaa is Orn
```

(xi) SEQUENCE DESCRIPTION: SEQ ID NO:15:

Xaa Tyr Ile His Pro Phe
1               5

(2) INFORMATION FOR SEQ ID NO:16:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        (A) ORGANISM: Bos taurus (ix) FEATURE:
        (A) NAME/KEY: Modified-site
        (B) LOCATION: N-terminal amino acid.
        (D) OTHER INFORMATION:
            /note= Xaa1 is D-valine, N-methylglycine (sarcosine),
            methylated-I, benzoic acid, or 6-amino hexanoic acid;
            Xaa6 is phenylalanine, but when Xaa1 is sarcosine, Xaa6
            can be isoleucine.

(xi) SEQUENCE DESCRIPTION: SEQ ID NO:16:

Xaa Tyr Ile His Pro Xaa
1               5

(2) INFORMATION FOR SEQ ID NO:17:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        (A) ORGANISM: Bos taurus (xi) SEQUENCE DESCRIPTION: SEQ ID NO:17:

Phe Tyr Ile His Pro Phe
1               5

(2) INFORMATION FOR SEQ ID NO:18:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal

```
        (vi) ORIGINAL SOURCE:
             (A) ORGANISM: Bos taurus (xi) SEQUENCE DESCRIPTION: SEQ ID NO:18:

Ile Tyr Ile His Pro Phe
1               5

(2) INFORMATION FOR SEQ ID NO:19:

(i) SEQUENCE CHARACTERISTICS:
             (A) LENGTH: 6 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
             (A) ORGANISM: Bos taurus (xi) SEQUENCE DESCRIPTION: SEQ ID NO:19:

Ala Tyr Ile His Pro Phe
1               5

(2) INFORMATION FOR SEQ ID NO:20:

(i) SEQUENCE CHARACTERISTICS:
             (A) LENGTH: 6 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
             (A) ORGANISM: Bos taurus (ix) FEATURE:
             (A) NAME/KEY: Modified-site
             (B) LOCATION: N-terminal amino acid
             (D) OTHER INFORMATION:
                 /note= Xaa is Me-Ile (xi) SEQUENCE DESCRIPTION: SEQ ID NO:20:

Xaa Tyr Ile His Pro Phe
1               5

(2) INFORMATION FOR SEQ ID NO:21:

(i) SEQUENCE CHARACTERISTICS:
             (A) LENGTH: 6 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO
```

(v) FRAGMENT TYPE: N-terminal (vi) ORIGINAL SOURCE:
               (A) ORGANISM: Bos taurus (xi) SEQUENCE DESCRIPTION: SEQ ID NO:21:

Pro Tyr Ile His Pro Phe
1               5

(2) INFORMATION FOR SEQ ID NO:22:

(i) SEQUENCE CHARACTERISTICS:
               (A) LENGTH: 6 amino acids
               (B) TYPE: amino acid
               (C) STRANDEDNESS: single
               (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
               (A) ORGANISM: Bos taurus (ix) FEATURE:
               (D) OTHER INFORMATION:
                    /note= Xaa is nothing or gamma-amino butyric acid (GABA)

(xi) SEQUENCE DESCRIPTION: SEQ ID NO:22:

Xaa Tyr Ile His Pro Phe
1               5

(2) INFORMATION FOR SEQ ID NO:23:

(i) SEQUENCE CHARACTERISTICS:
               (A) LENGTH: 6 amino acids
               (B) TYPE: amino acid
               (C) STRANDEDNESS: single
               (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
               (A) ORGANISM: Bos taurus (ix) FEATURE:
               (D) OTHER INFORMATION:
                    /note= Xaa is D-Tyr (xi) SEQUENCE DESCRIPTION: SEQ ID NO:23:

Val Xaa Ile His Pro Phe
1               5

(2) INFORMATION FOR SEQ ID NO:24:

(i) SEQUENCE CHARACTERISTICS:
               (A) LENGTH: 6 amino acids
               (B) TYPE: amino acid
               (C) STRANDEDNESS: single
               (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
             (A) ORGANISM: Bos taurus (xi) SEQUENCE DESCRIPTION: SEQ ID NO:24:

Val Phe Ile His Pro Phe
1               5

(2) INFORMATION FOR SEQ ID NO:25:

(i) SEQUENCE CHARACTERISTICS:
             (A) LENGTH: 6 amino acids
             (B) TYPE: amino acid
             (C) STRANDEDNESS: single
             (D) TOPOLOGY: linear (ii) MOLECULE TYPE: peptide
             (A) DESCRIPTION: divalinal Angiotensin IV (iii) HYPOTHETICAL: NO (iv) ANTI-SENSE: NO (v) FRAGMENT TYPE: N-terminal (vi) ORIGINAL SOURCE:
             (A) ORGANISM: Bos taurus (ix) FEATURE:
             (A) NAME/KEY: Modified-site
             (B) LOCATION: Multiple
             (D) OTHER INFORMATION:
                 /note= Val1-Tyr2 and Val3-His4 are methylene bonds
                 instead of peptide bonds.

(xi) SEQUENCE DESCRIPTION: SEQ ID NO:25:

Val Tyr Val His Pro Phe
1               5

(2) INFORMATION FOR SEQ ID NO:26:

(i) SEQUENCE CHARACTERISTICS:
             (A) LENGTH: 6 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
             (A) ORGANISM: Bos taurus (xi) SEQUENCE DESCRIPTION: SEQ ID NO:26:

Lys Tyr Ile His Pro Ile
1               5

(2) INFORMATION FOR SEQ ID NO:27:

(i) SEQUENCE CHARACTERISTICS:
             (A) LENGTH: 5 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
             (A) ORGANISM: Bos taurus (xi) SEQUENCE DESCRIPTION: SEQ ID NO:27:

Val Tyr Ile His Pro
1               5

(2) INFORMATION FOR SEQ ID NO:28:

(i) SEQUENCE CHARACTERISTICS:
             (A) LENGTH: 7 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
             (A) ORGANISM: Bos taurus (xi) SEQUENCE DESCRIPTION: SEQ ID NO:28:

Val Tyr Ile His Pro Phe His
1               5

(2) INFORMATION FOR SEQ ID NO:29:

(i) SEQUENCE CHARACTERISTICS:
             (A) LENGTH: 8 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
             (A) ORGANISM: Bos taurus (xi) SEQUENCE DESCRIPTION: SEQ ID NO:29:

Val Tyr Ile His Pro Phe His Leu
1               5

(2) INFORMATION FOR SEQ ID NO:30:

(i) SEQUENCE CHARACTERISTICS:
             (A) LENGTH: 4 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
            (A) ORGANISM: Bos taurus (xi) SEQUENCE DESCRIPTION: SEQ ID NO:30:

Val Tyr Ile His
1

(2) INFORMATION FOR SEQ ID NO:31:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
            (A) ORGANISM: Bos taurus (ix) FEATURE:
            (A) NAME/KEY: Modified-site
            (B) LOCATION: Multiple
            (D) OTHER INFORMATION:
                /note= Includes variants from which deletions have been
                  made at the C-terminus by 1, 2, 3, 4, or 5 residues.

(xi) SEQUENCE DESCRIPTION: SEQ ID NO:31:

Asn Arg Val Tyr Ile His Pro Phe
1               5

(2) INFORMATION FOR SEQ ID NO:32:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide
            (A) DESCRIPTION: Bacitracin (iii) HYPOTHETICAL: NO (iv) ANTI-SENSE: NO (v) FRAGMENT TYPE: N-terminal (vi) ORIGINAL SOURCE:
            (A) ORGANISM: Bos taurus (ix) FEATURE:
            (A) NAME/KEY: Modified-site
            (B) LOCATION: Amino acid 7
            (D) OTHER INFORMATION:
                /note= Xaa is Orn (xi) SEQUENCE DESCRIPTION: SEQ ID NO:32:

Ile Cys Leu Glu Ile Lys Xaa Ile Phe His Asp Asp
1               5                   10

(2) INFORMATION FOR SEQ ID NO:33:

(i) SEQUENCE CHARACTERISTICS:
            (A) LENGTH: 5 amino acids (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
            (A) ORGANISM: Bos taurus (xi) SEQUENCE DESCRIPTION: SEQ ID NO:33:

Tyr Ile His Pro Phe
1               5

(2) INFORMATION FOR SEQ ID NO:34:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
            (A) ORGANISM: Bos taurus (xi) SEQUENCE DESCRIPTION: SEQ ID NO:34:

Asp Tyr Ile His Pro Phe
1               5

(2) INFORMATION FOR SEQ ID NO:35:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
            (A) ORGANISM: Bos taurus (ix) FEATURE:
            (A) NAME/KEY: Modified-site
            (B) LOCATION: Amino acid 1
            (D) OTHER INFORMATION:
                /note= Xaa is Nva (xi) SEQUENCE DESCRIPTION: SEQ ID NO:35:

Xaa Tyr Ile His Pro Phe
1               5

(2) INFORMATION FOR SEQ ID NO:36:

(i) SEQUENCE CHARACTERISTICS:

(A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        (A) ORGANISM: Bos taurus (xi) SEQUENCE DESCRIPTION: SEQ ID NO:36:

Val Pro Ile His Tyr Phe
1               5

(2) INFORMATION FOR SEQ ID NO:37:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        (A) ORGANISM: Bos taurus (xi) SEQUENCE DESCRIPTION: SEQ ID NO:37:

Val Tyr Ile His Pro Ile
1               5

(2) INFORMATION FOR SEQ ID NO:38:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        (A) ORGANISM: Bos taurus (ix) FEATURE:
        (A) NAME/KEY: Modified-site
        (B) LOCATION: Amino acid 1
        (D) OTHER INFORMATION:
            /note= Xaa/1 is Nle (xi) SEQUENCE DESCRIPTION: SEQ ID NO:38:

Xaa Tyr Ile His Pro Ile
1               5